United States Patent
Dacosta et al.

(10) Patent No.: US 11,883,038 B2
(45) Date of Patent: Jan. 30, 2024

(54) IMPLANTS, DEVICES, SYSTEMS, KITS AND METHODS OF IMPLANTING

(71) Applicant: Paragon 28, Inc., Englewood, CO (US)

(72) Inventors: Albert Dacosta, Lone Tree, CO (US); Benjamin Majors, Englewood, CO (US); Jens Cole, Golden, CO (US); Frank S. Bono, Castle Rock, CO (US)

(73) Assignee: Paragon 28, Inc., Englewood, CO (US)

( * ) Notice: Subject to any disclaimer, the term of this patent is extended or adjusted under 35 U.S.C. 154(b) by 138 days.

(21) Appl. No.: 17/248,454

(22) Filed: Jan. 25, 2021

(65) Prior Publication Data
US 2021/0145457 A1 May 20, 2021

Related U.S. Application Data

(60) Division of application No. 15/920,887, filed on Mar. 14, 2018, now Pat. No. 10,898,206, which is a
(Continued)

(51) Int. Cl.
| | |
|---|---|
| *A61B 17/17* | (2006.01) |
| *A61B 17/15* | (2006.01) |
| *A61F 2/28* | (2006.01) |
| *A61F 2/38* | (2006.01) |
| *A61F 5/00* | (2006.01) |
| *A61F 2/42* | (2006.01) |
| *A61B 17/80* | (2006.01) |

(Continued)

(52) U.S. Cl.
CPC ........ *A61B 17/152* (2013.01); *A61B 17/1775* (2016.11); *A61B 17/8095* (2013.01); *A61F 2/4225* (2013.01); *A61F 2/4606* (2013.01); *A61F 2/4603* (2013.01); *A61F 2002/30131* (2013.01); *A61F 2002/30281* (2013.01); *A61F 2002/4238* (2013.01); *A61F 2002/4681* (2013.01); *A61F 2002/4687* (2013.01)

(58) Field of Classification Search
None
See application file for complete search history.

(56) References Cited

U.S. PATENT DOCUMENTS 5,474,559 A * 12/1995 Bertin ................ A61B 17/17
606/88
5,766,251 A 6/1998 Koshino
(Continued)

FOREIGN PATENT DOCUMENTS

| EP | 1772108 | 4/2007 | | |
|---|---|---|---|---|
| WO | WO-9907312 A1 * | 2/1999 | ............... | A61F 2/44 |

(Continued)

OTHER PUBLICATIONS

Extended European Search Report issued in European Patent Application No. 18753856.6, dated Feb. 12, 2021, 10 pages.
(Continued)

*Primary Examiner* — Ann Schillinger
(74) *Attorney, Agent, or Firm* — Heslin Rothenberg Farley & Mesiti PC; Jacquelyn A. Graff, Esq.

(57) ABSTRACT

Implants, devices, instruments, kits and methods for correcting bone deformities in the foot are disclosed. Specifically, implants, devices, instruments, kits and methods used for lower extremity osteotomy procedures are disclosed.

18 Claims, 44 Drawing Sheets

Related U.S. Application Data continuation of application No. PCT/US2018/000076, filed on Feb. 16, 2018.

(60) Provisional application No. 62/459,772, filed on Feb. 16, 2017.

(51) Int. Cl.
*A61F 2/46* (2006.01)
*A61F 2/30* (2006.01)

(56) References Cited

U.S. PATENT DOCUMENTS

| | | | |
|---|---|---|---|
| 7,585,326 B2 | 9/2009 | de Villiers | |
| 7,704,253 B2* | 4/2010 | Bastian | A61B 17/154 606/88 |
| 7,935,119 B2* | 5/2011 | Ammann | A61B 17/1764 623/20.32 |
| 8,241,292 B2 | 8/2012 | Collazo | |
| 8,430,930 B2* | 4/2013 | Hunt | A61F 2/40 623/17.11 |
| 9,271,845 B2 | 3/2016 | Hunt | |
| 9,364,340 B2* | 6/2016 | Lawson | A61B 17/8042 |
| 9,421,108 B2 | 8/2016 | Hunt | |
| 9,545,317 B2 | 1/2017 | Hunt | |
| 9,572,669 B2 | 2/2017 | Hunt | |
| 9,622,805 B2* | 4/2017 | Santrock | A61B 17/152 |
| 9,636,226 B2* | 5/2017 | Hunt | A61F 2/4611 |
| D813,394 S | 3/2018 | DaCosta | |
| D814,037 S | 3/2018 | DaCosta | |
| D814,634 S | 4/2018 | DaCosta | |
| 9,936,994 B2 | 4/2018 | Smith et al. | |
| 9,999,516 B2 | 6/2018 | Hunt | |
| 10,045,807 B2 | 8/2018 | Santrock et al. | |
| D832,441 S | 10/2018 | DaCosta | |
| D841,168 S | 2/2019 | DaCosta | |
| D849,944 S | 5/2019 | DaCosta | |
| 10,278,742 B2* | 5/2019 | Pavlov | A61F 2/447 |
| 10,335,220 B2 | 7/2019 | Smith et al. | |
| 10,342,590 B2 | 7/2019 | Bays et al. | |
| 10,898,206 B2* | 1/2021 | Dacosta | A61F 2/4225 |
| 11,033,394 B2* | 6/2021 | Hamzey | A61F 2/4081 |
| 2001/0005796 A1* | 6/2001 | Zdeblick | A61F 2/4611 623/17.11 |
| 2002/0004683 A1* | 1/2002 | Michelson | A61F 2/4637 623/17.16 |
| 2003/0105526 A1* | 6/2003 | Bryant | A61F 2/28 623/16.11 |
| 2005/0075641 A1* | 4/2005 | Singhatat | A61B 17/15 606/86 R |
| 2005/0124995 A1* | 6/2005 | Reiley | A61F 2/4202 606/62 |
| 2005/0240267 A1* | 10/2005 | Randall | A61F 2/4611 623/17.11 |
| 2006/0030851 A1* | 2/2006 | Bray | A61B 17/7059 606/279 |
| 2008/0177307 A1* | 7/2008 | Moskowitz | A61B 17/809 606/301 |
| 2010/0168752 A1* | 7/2010 | Edwards | A61B 17/155 606/85 |
| 2010/0256687 A1* | 10/2010 | Neufeld | A61B 17/8061 606/280 |
| 2011/0313532 A1* | 12/2011 | Hunt | A61F 2/46 623/18.11 |
| 2012/0265301 A1 | 10/2012 | Demers et al. | |
| 2012/0271314 A1* | 10/2012 | Stemniski | A61B 17/1775 606/87 |
| 2013/0030540 A1* | 1/2013 | Leibinger | A61F 2/28 29/505 |
| 2013/0218282 A1* | 8/2013 | Hunt | A61F 2/447 623/23.42 |
| 2013/0325076 A1 | 12/2013 | Palmer | |
| 2014/0135775 A1 | 5/2014 | Maxson | |
| 2014/0228957 A1* | 8/2014 | Niemiec | A61F 2/4455 623/17.16 |
| 2015/0335367 A1* | 11/2015 | Austin | A61B 17/8095 606/86 R |
| 2016/0199113 A1* | 7/2016 | Penzimer | A61B 17/0642 606/301 |
| 2016/0228257 A1 | 8/2016 | Predick et al. | |
| 2018/0317992 A1 | 11/2018 | Santrock et al. | |
| 2019/0274745 A1 | 9/2019 | Smith et al. | |
| 2019/0328435 A1 | 10/2019 | Bays et al. | |
| 2019/0328436 A1 | 10/2019 | Bays et al. | |

FOREIGN PATENT DOCUMENTS

| | | |
|---|---|---|
| WO | 2017011656 | 1/2017 |
| WO | 2017031000 | 2/2017 |
| WO | 2017031020 | 2/2017 |

OTHER PUBLICATIONS

International Search Report and Written Opinion of the International Searching Authority for PCT/US2018/000076, dated Jun. 25, 2018, 16 pages.

* cited by examiner

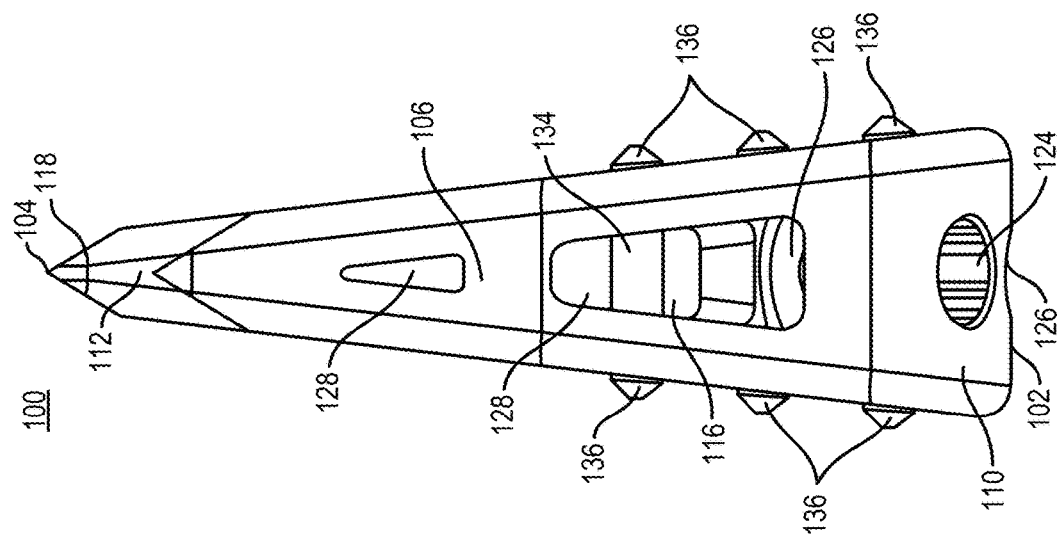
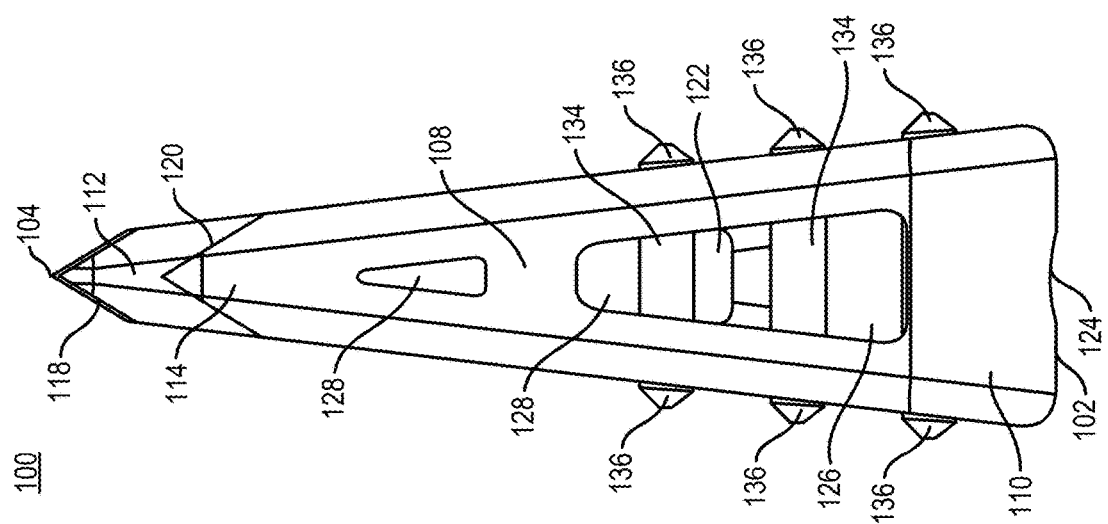

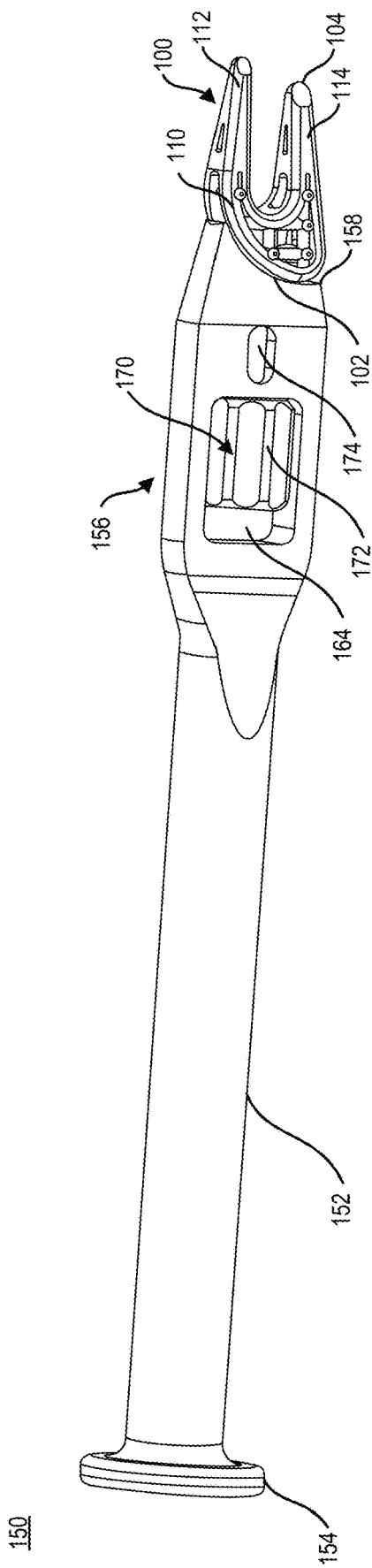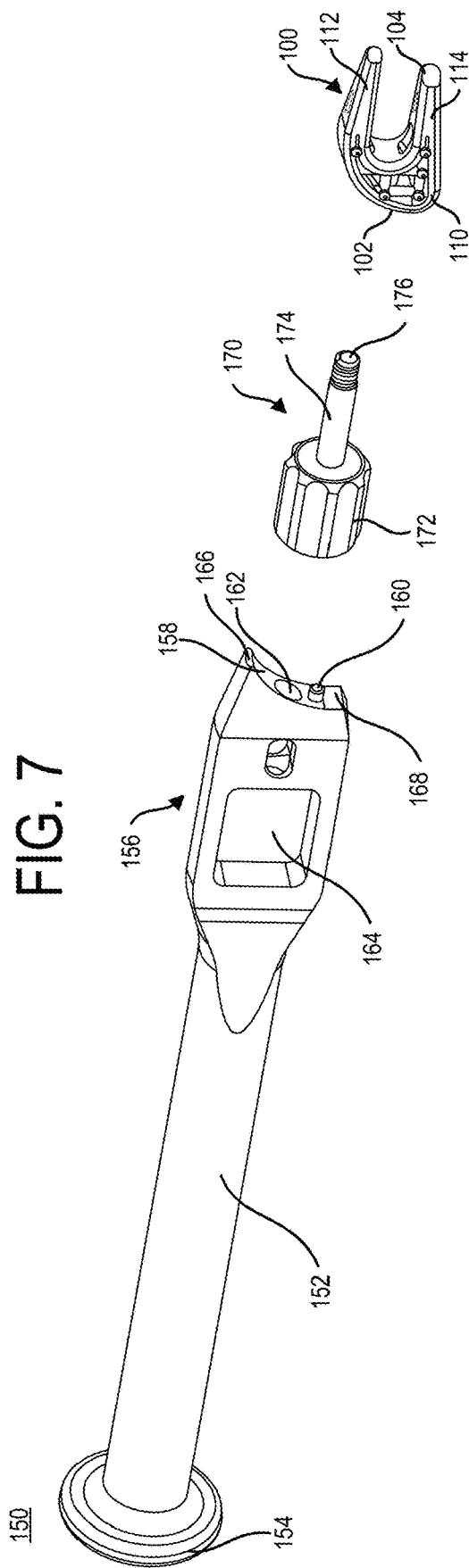
FIG. 7
FIG. 8

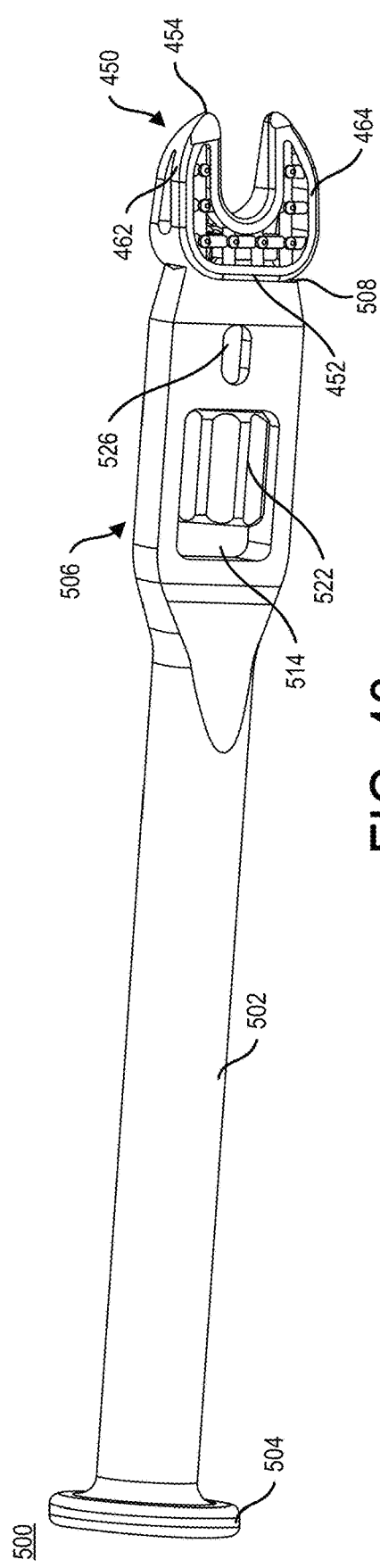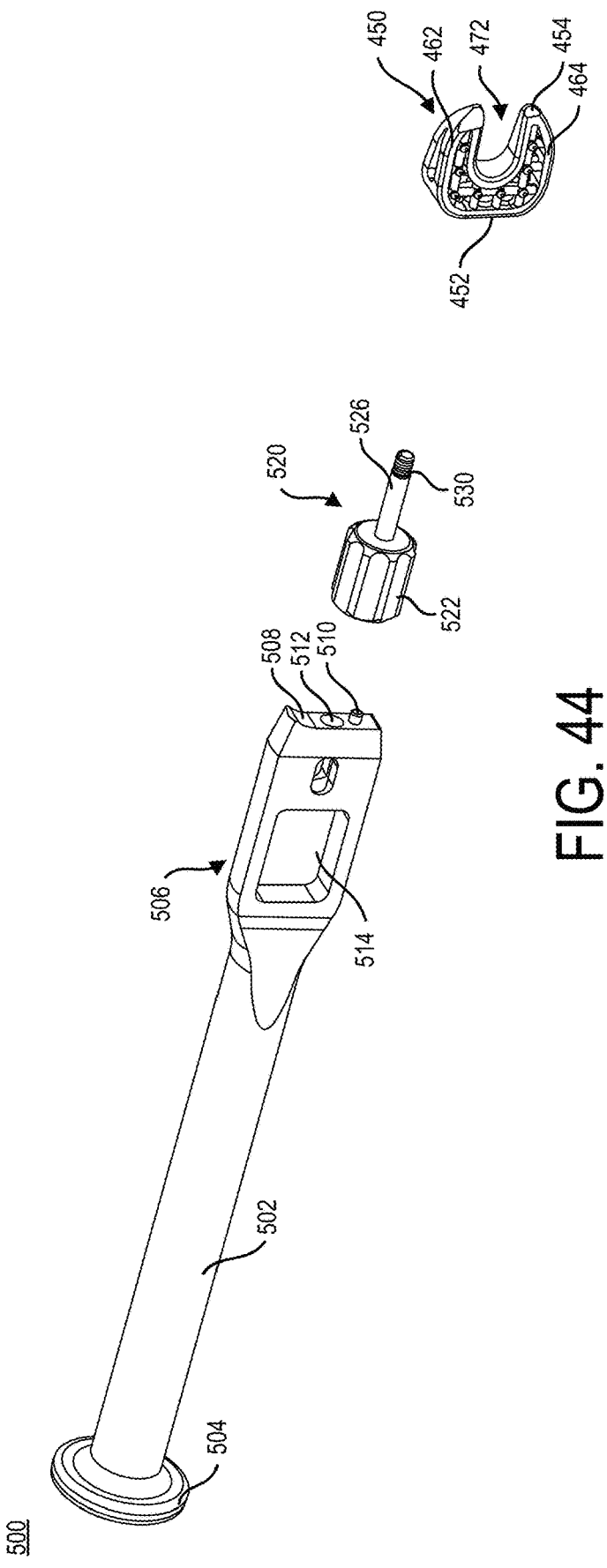
FIG. 43
FIG. 44

US 11,883,038 B2

IMPLANTS, DEVICES, SYSTEMS, KITS AND METHODS OF IMPLANTING

CROSS REFERENCE TO RELATED APPLICATION

This application is a divisional of U.S. application Ser. No. 15/920,887 filed on Mar. 14, 2018 and issuing as U.S. Pat. No. 10,898,206 on Jan. 26, 2021, which is a continuation of PCT Application No. PCT/US2018/000076 filed on Feb. 16, 2018, which claims priority benefit under 35 U.S.C. § 119(e) of U.S. provisional application No. 62/459,772 filed Feb. 16, 2017, which are incorporated herein by reference in their entireties.

FIELD OF THE INVENTION

The present invention relates generally to general surgery, orthopaedic implants used for correcting bone deformities. More specifically, but not exclusively, the present invention relates to implants, devices, systems, kits and methods for correcting bone deformities.

BACKGROUND OF THE INVENTION

Many currently available osteotomy procedures use implants made of allograft or autograft bone. When allograft or autograft bone is used it integrates into the patient's bone after implantation, if a revision procedure is needed it may be difficult to distinguish between the allograft/autograft bone and the patient's own bone. Thus, new methods, implants, and instruments are needed to provide implants made of non-allograft or non-autograft bone while still allowing for bone integration and that allow for easier removal during a revisions surgery.

SUMMARY OF THE INVENTION

Aspects of the present invention provide implants, devices and methods for correcting bone deformities in the foot.

In one aspect, provided herein is an osteotomy system or kit. The osteotomy system or kit includes, at least one implant, at least one insertion instrument, a fastener guide, and a resection guide.

In another aspect, provided herein is an implant. The implant includes, a body with an opening extending through the body from a top surface to a bottom surface. The opening includes a plurality of struts extending across the opening and coupled to the body and at least two spikes coupled to at least one of the plurality of struts and extending out from the body.

In yet another aspect, provided herein is an insertion instrument. The insertion instrument includes a body, a nose portion, and a securement member extending through the securement opening and projecting past the contact surface to couple to a securement opening in the implant. The nose portion includes a contact surface shaped to match a shape of a first end of the implant, an alignment pin extending from the contact surface to mate with an alignment opening in the implant, and a securement opening.

In another aspect, provided herein is a fastener guide. The fastener guide includes an alignment arm with a first end and a second end, an insertion guide removably coupled to the first end of the alignment arm, and a fixation member removably coupled to the second end of the alignment arm and extending through the alignment arm to engage the implant. The alignment arm includes a base member, a first arm coupled to the base member at the first end, wherein the first arm is angled relative to the base member, and a second arm coupled to the base member at the second end.

In a further aspect, provided herein is a resection guide. The resection guide includes a central portion with a first side opposite a second side and a first end opposite a second end, at least one first slot positioned on the first side of the central portion, at least one second slot positioned on the second side of the central portion, and at least one leg extending from the second end and angled with respect to the central portion. The at least one first slot and at least one second slot extend along the entire length of the central portion and into at least a portion of the at least one leg.

In yet another aspect, provided herein is a surgical method for correcting bone deformities in the foot. The method including performing an osteotomy procedure to form an opening in a bone and selecting an implant for insertion into the opening. The method also including coupling the implant to an insertion instrument and inserting the implant into the opening. The method further including removing the insertion instrument from the implant and completing the osteotomy procedure.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention. It is emphasized that, in accordance with the standard practice in the industry, various features are not drawn to scale. In fact, the dimensions of the various features may be arbitrarily increased or reduced for clarity of discussion. The foregoing and other objects, features and advantages of the invention are apparent from the following detailed description taken in conjunction with the accompanying drawings in which:

FIG. 3 is a first side view of the implant of FIG. 1, in accordance with an aspect of the present invention;

FIG. 4 is a second side view of the implant of FIG. 1, in accordance with an aspect of the present invention;

FIG. 7 is a side view of one embodiment of an inserter instrument coupled to the implant of FIG. 1, in accordance with an aspect of the present invention;

FIG. 8 is an exploded perspective view of the inserter instrument and implant of FIG. 7, in accordance with an aspect of the present invention;

FIG. 43 is a side view of another embodiment of an inserter instrument coupled to the implant of FIG. 37, in accordance with an aspect of the present invention;

FIG. 44 is an exploded perspective view of the inserter instrument and implant of FIG. 43, in accordance with an aspect of the present invention;

DETAILED DESCRIPTION FOR CARRYING OUT THE INVENTION

Figure 1:
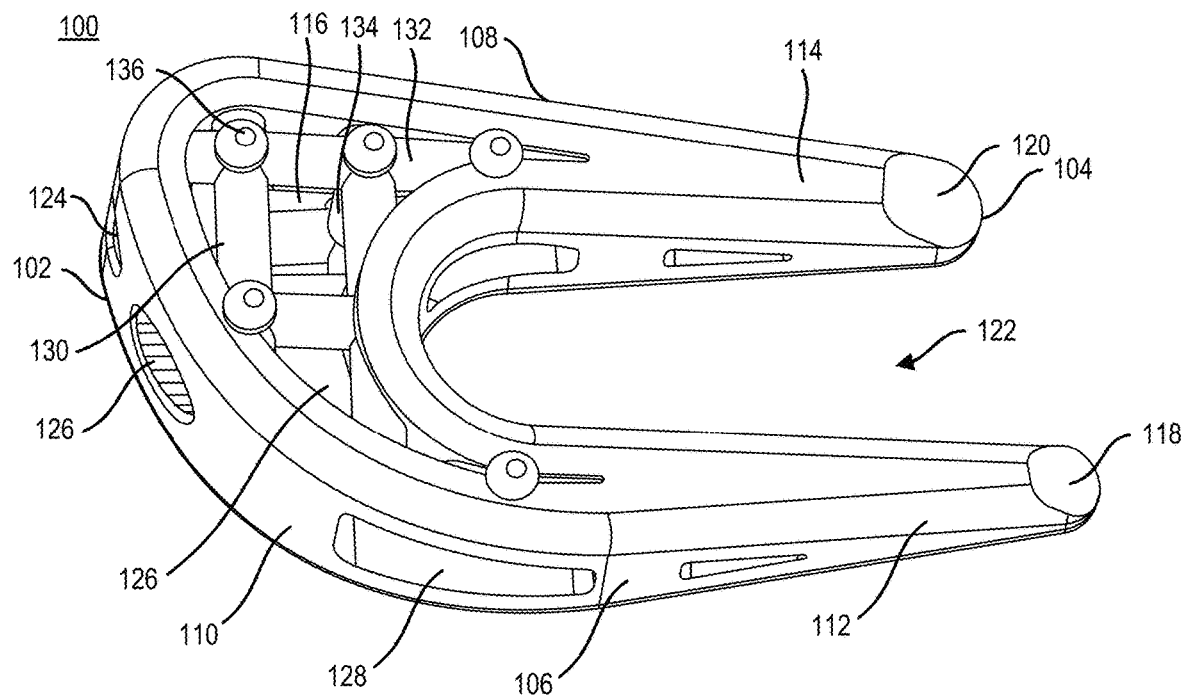
FIG. 1 is a perspective view of one embodiment of an implant, in accordance with an aspect of the present invention.

Generally stated, disclosed herein are implants, guides, instruments, systems, and kits for correcting bone deformities. Further, surgical methods for correcting bone deformities using the implants, guides, instruments and systems are discussed.

In this detailed description and the following claims, the words proximal, distal, anterior or plantar, posterior or dorsal, medial, lateral, superior and inferior are defined by their standard usage for indicating a particular part or portion of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers the bottom of the foot.

Similarly, positions or directions may be used herein with reference to anatomical structures or surfaces. For example, as the current implants, devices, instrumentation and methods are described herein with reference to use with the bones of the foot, the bones of the foot, ankle and lower leg may be used to describe the surfaces, positions, directions or orientations of the implants, devices, instrumentation and methods. Further, the implants, devices, instrumentation and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the implants, devices, instrumentation and methods, and the aspects, components, features and the like thereof, described and/or illustrated herein may be changed, varied, modified, reconfigured or otherwise altered for use or association with another side of the body for a same or similar purpose without departing from the spirit and scope of the invention. For example, the implants, devices, instrumentation and methods, and the aspects, components, features and the like thereof, described herein with respect to the right foot may be mirrored so that they likewise function with the left foot. Further, the implants, devices, instrumentation and methods, and the aspects, components, features and the like thereof, disclosed herein are described with respect to the foot for brevity purposes, but it should be understood that the implants, devices, instrumentation and methods may be used with other bones of the body having similar structures.

Referring to the drawings, wherein like reference numerals are used to indicate like or analogous components throughout the several views, and with particular reference to FIGS. 1-29, there is illustrated one embodiment of an implant kit or system including an implant 100, an inserter instrument 150, a fastener guide system 200, and a resection guide system 300. As shown in FIGS. 1-6, the implant 100 may include a first end 102, a second end 104, a first side 106 and a second side 108. The implant 100 may include a body or frame 110 with a first leg or projection 112, a second leg or projection 114, and an opening 116 extending through the body 110. The first leg 112 may be positioned on the first side 106 and the second leg 114 may be positioned on the second side 108. In the depicted embodiment, the first leg 112 is longer than the second leg 114. The ends or tips 118, 120 of the legs 112, 114 may be, for example, tapered or otherwise shaped to aide in insertion into an opening within a patient's bone. The legs 112, 114 may be spaced apart to define a channel 122 between the legs 112, 114. As discussed in greater detail below, the channel 122 may be sized and shaped to allow for a fastener, for example, a bone screw, to pass through the channel 122 and across the osteotomy site.

Figure 2:
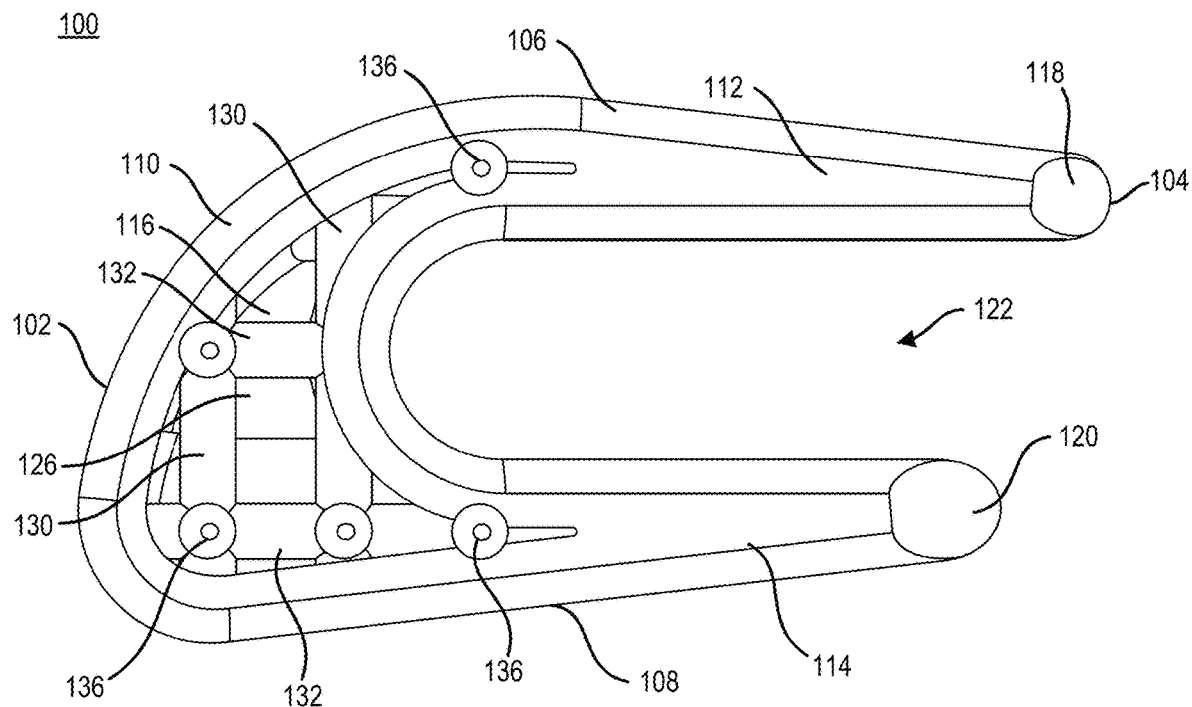
FIG. 2 is a front view of the implant of FIG. 1, in accordance with an aspect of the present invention.
Figure 5:
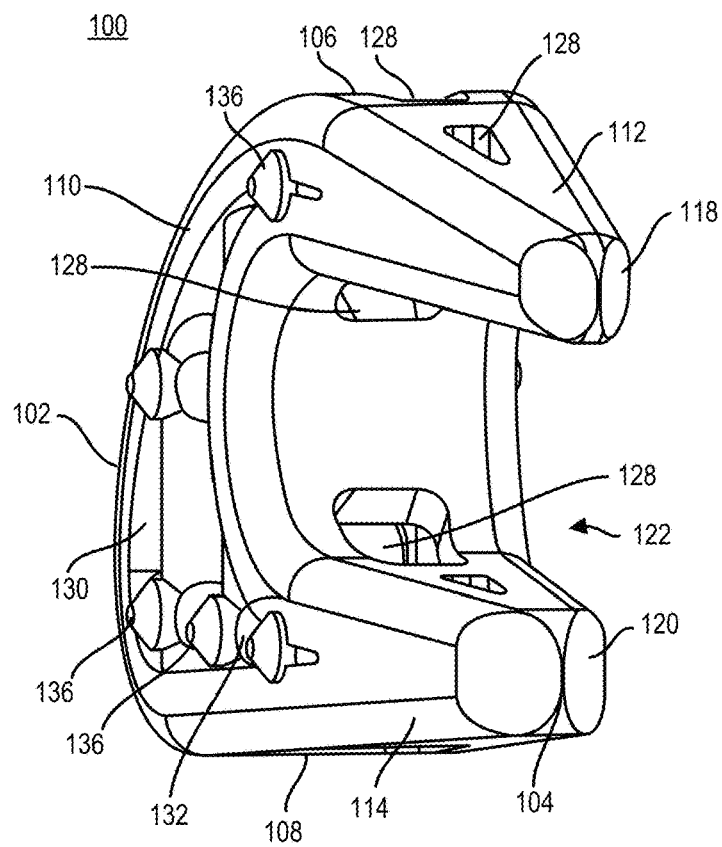
FIG. 5 is a bottom view of the implant of FIG. 1, in accordance with an aspect of the present invention.
Figure 15:
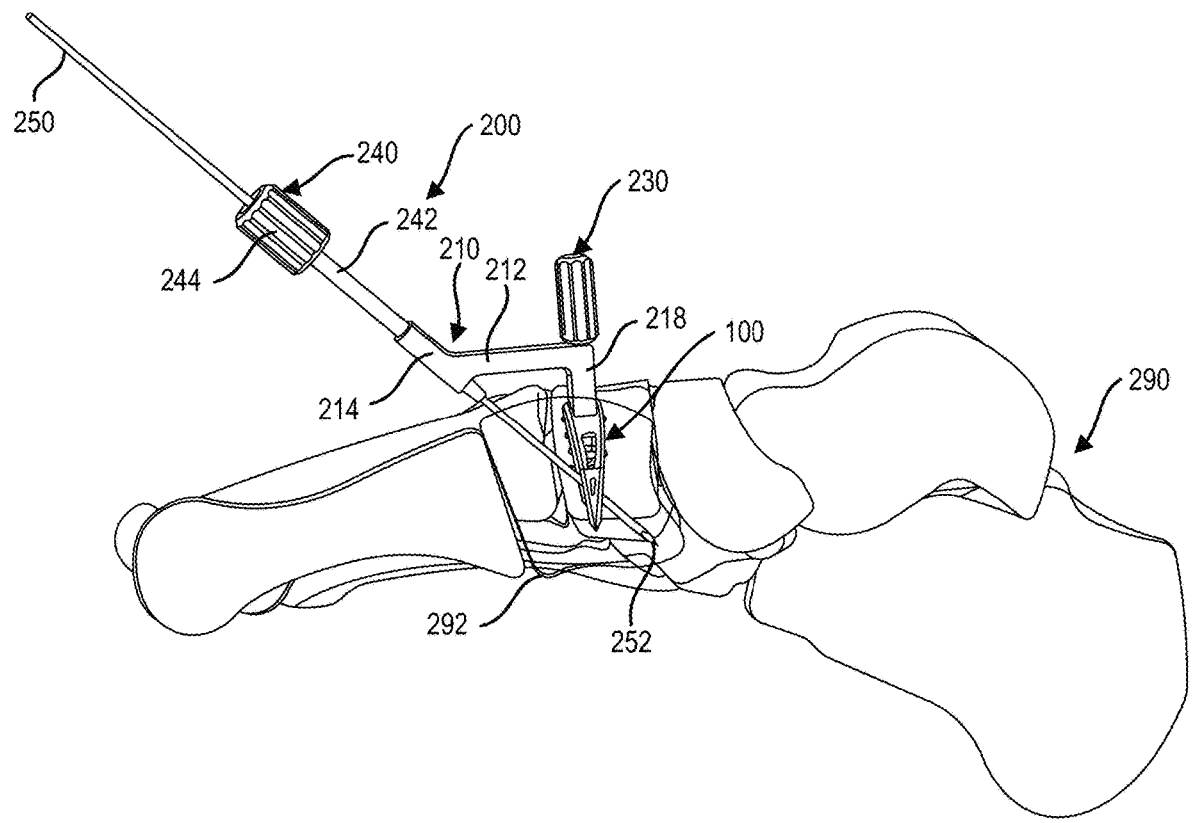
FIG. 15 is a side view of the fastener guide and implant of FIG. 11 positioned with respect to a portion of a foot, in accordance with an aspect of the present invention.
Figure 16:
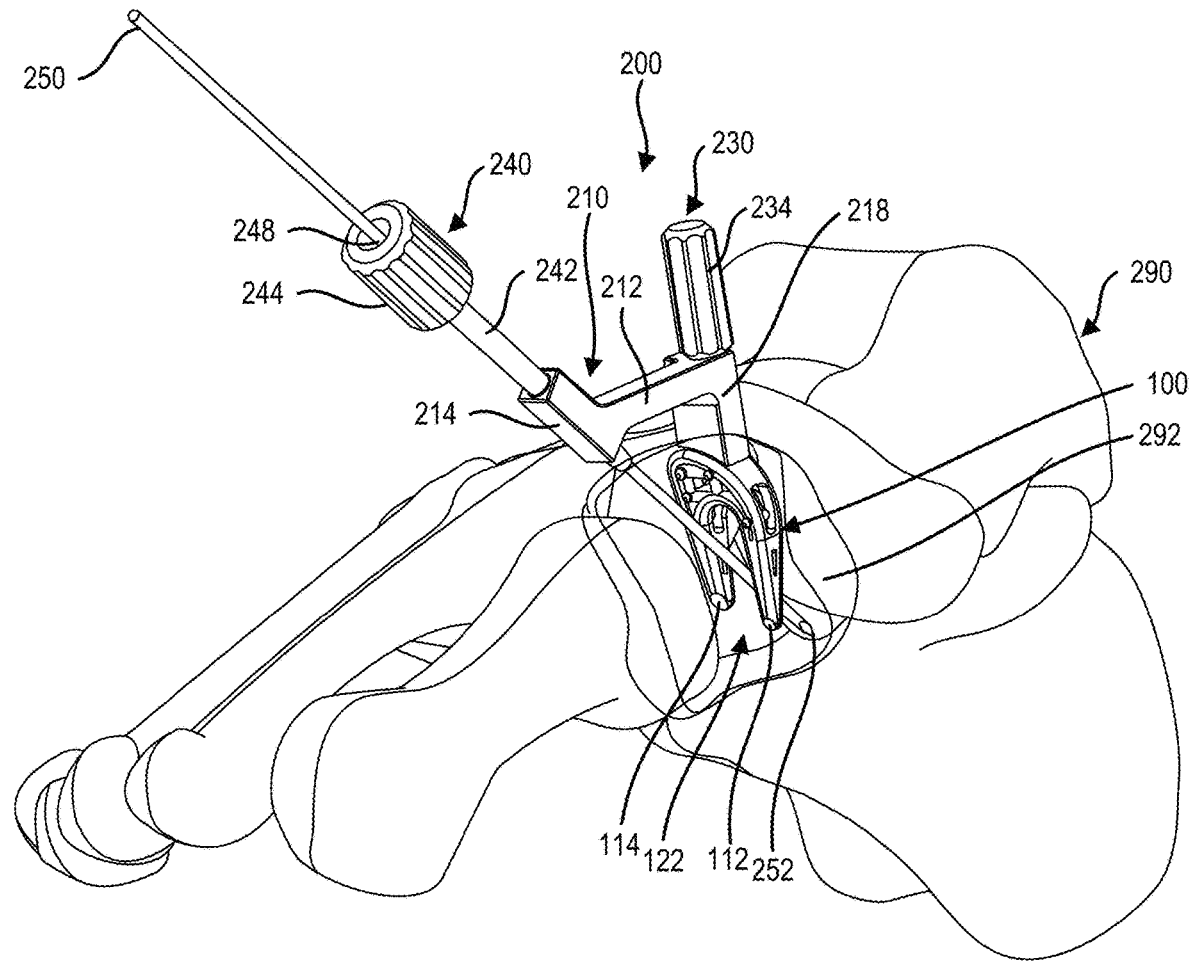
FIG. 16 is a front perspective view of the fastener guide and implant of FIG. 11, in accordance with an aspect of the present invention.
Figure 17:
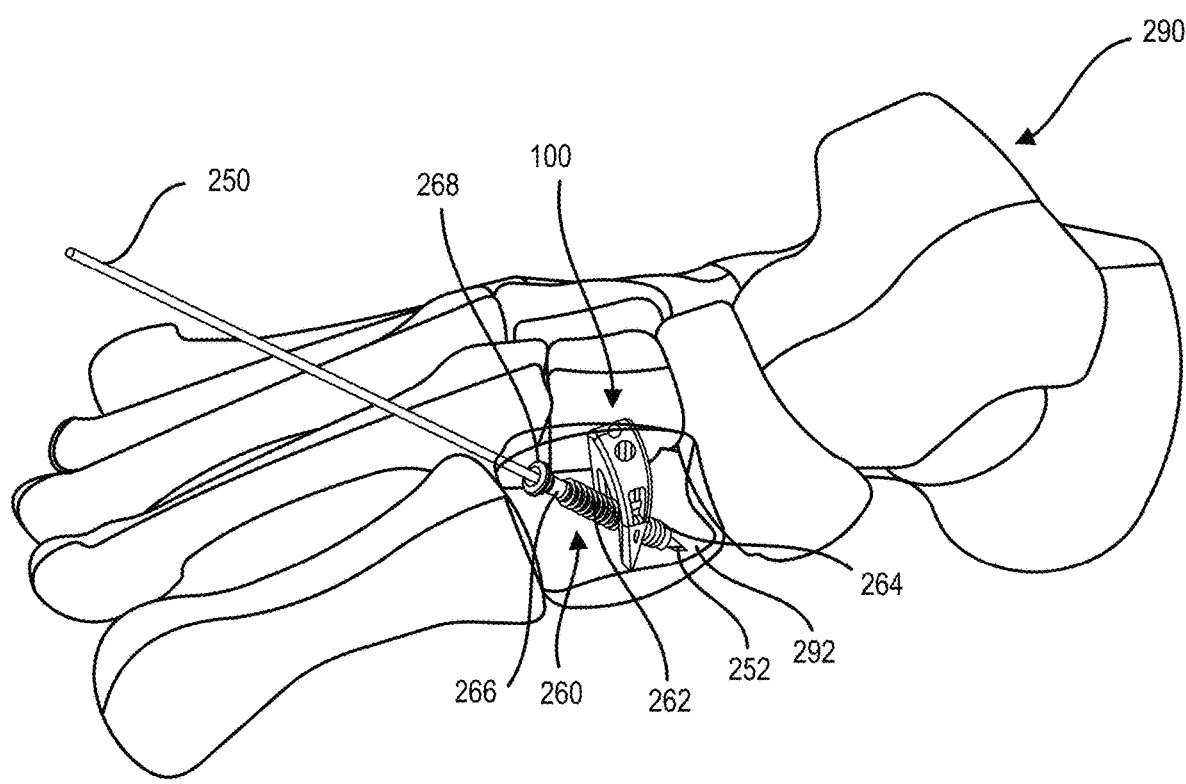
FIG. 17 is a top perspective view of the foot of FIG. 16 showing the implant, k-wire, and fastener inserted into the portion of the foot, in accordance with an aspect of the present invention.

The first end 102 of the body 110 may be, for example, arched or curved such that the curved end 102 on the second side 108 extends beyond the curved end 102 on the first side 106, as shown in FIGS. 1 and 2. The exterior surface of the arched or curved first end 102 of the body 110 may have a shape corresponding to a patient's medial cuneiform bone 292, as shown in FIGS. 15-17. The surface of the first end 102 may be, for example, smooth. The first end 102 of the body 110 may have a height extending from the proximal surface to the distal surface. The implants 100 may have body heights at the first end 102 ranging from, for example, approximately 5 mm to approximately 8 mm. The height of the implant 100 may be selected based on the desired correction. The body 110 may also have a dorsal to plantar taper, for example, a taper from the first end 102 to the second end 104, as shown in FIGS. 3 and 4. The ends 118, 120 of the implant 100 may be, for example, further tapered to form a point at each end 118, 120. In addition, the body 110 may have a medial to lateral taper, for example, a taper from the second side 108 to the first side 106, as shown in FIGS. 5 and 6.

Figure 6:
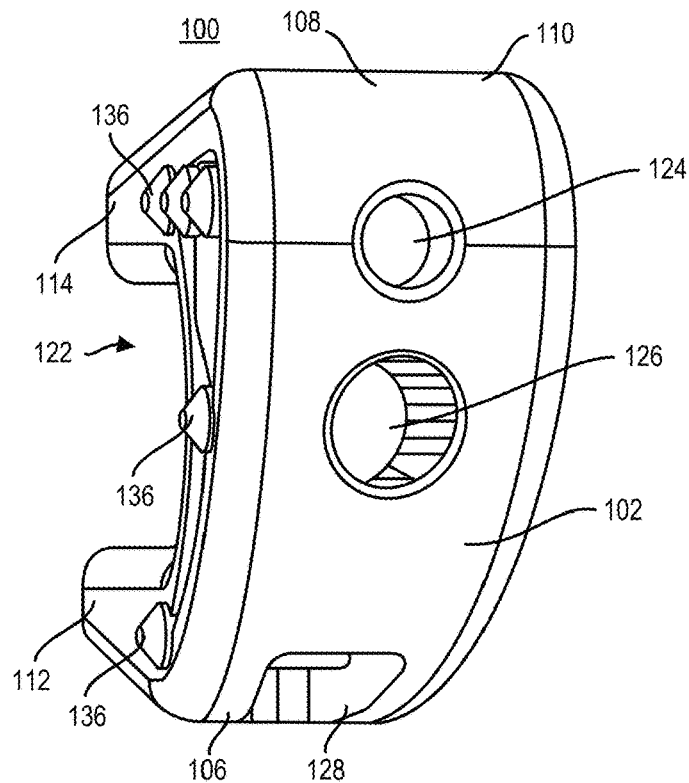
FIG. 6 is a top view of the implant of FIG. 1, in accordance with an aspect of the present invention.

As shown in FIGS. 1 and 6, the first end 102 of the body 110 may also include an alignment opening 124 and a securement opening 126. The alignment opening 124 may be positioned adjacent to the securement opening 126 on the first end 102 of the implant 100. The alignment opening 124 may be, for example, sized and shaped to receive an alignment pin from an insertion instrument 150, guide system 200 and/or resection guide 300, as described in greater detail below. The alignment opening 124 may, for example, extend into the body 110 at the first end 102 and terminate before the opening 116. The securement opening 126 may be, for example, threaded to receive a fastener to couple the implant 100 to an insertion instrument 150, guide system 200 and/or resection guide 300, as described in greater detail below. The securement opening 126 may be, for example, threaded to engage threads on a fastener. The securement opening 126 may, for example, extend into the first end 102 of the body 110, through the opening 116, and into at least a portion of the body 110 at the bottom of the channel 122. The securement opening 126 may extend into the implant 100 farther than the alignment opening 124. The body 110 may also include at least one window or opening 128 on the first side 106 and the second side 108 of the implant 100, as shown in FIGS. 3-6. The windows 128 may be, for example, sized and shaped to allow for bone growth and cross-communication of blood within the osteotomy site.

As shown in FIGS. 1 and 2, the opening 116 may include, a plurality of struts or linear members 130, 132, 134 extending across the opening 116 and coupled to the body 110. The plurality of struts 130, 132, 134 may include, for example, a first set of struts 130, a second set of struts 132, and a third set of struts 134. The first set of struts 130 may extend, for example, in a medial-lateral direction, as shown in FIGS. 1 and 2. The second set of struts 132 may extend, for example, in a dorsal-plantar direction, as shown in FIGS. 1 and 2. The third set of struts 134 may extend, for example, in a proximal-distal direction, as shown in FIGS. 3 and 4. A first group of struts 130, 132 may be, for example, positioned inset into the opening 116 on the front surface of the implant 100, as shown in FIG. 1. A second group of struts 130, 132 may be, for example, positioned inset into the opening 116 on the back surface of the implant 100, as shown in FIG. 2. The third set of struts 134 may extend between the first group of struts 130, 132 and the second group of struts 130, 132, as shown in FIGS. 3 and 4, forming a three dimensional matrix within the opening 116. The third set of struts 134 may be positioned perpendicular to the first set of struts 130 and the second set of struts 132. In addition to the strut embodiment shown, alternative strut arrangements are also contemplated in the opening 116 which provide the necessary support structure for the implant 100 and allow for bone through-growth, incorporation of biologic products, and/or allow for cross-communication of blood.

The implant 100 may also include a plurality of protrusions or spikes 136, as shown in FIGS. 1-6. The spikes 136 may be, for example, coupled to at least one of the struts 130, 132, 134. Although, five spikes 136 are shown on each side of the implant 100 in the depicted embodiment, alternative numbers of spikes 136 are also contemplated to secure the implant 100 within the osteotomy opening in the bone, for example, at least two spikes are contemplated. The spikes 136 may, for example, extend beyond the proximal and distal surfaces of the implant 100 to engage the surrounding bone and prevent expulsion from the osteotomy site. The spikes 136 may extend, for example, approximately 0.25 mm to approximately 1 mm and, more specifically, approximately 0.5 mm above the proximal surface or distal surface of the implant 100. Although shown as circular protrusions 136, it is also contemplated that other shapes that could assist with securing the implant 100 within the osteotomy site may be used.

Figure 9:
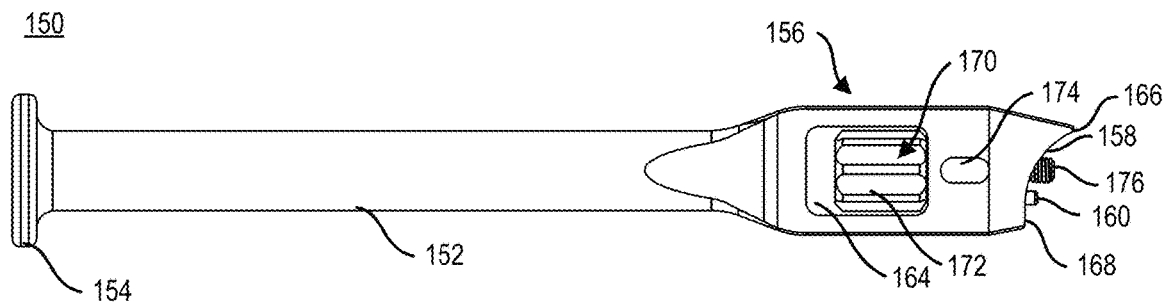
FIG. 9 is a side view of the insertion instrument of FIG. 7, in accordance with an aspect of the present invention.
Figure 10:
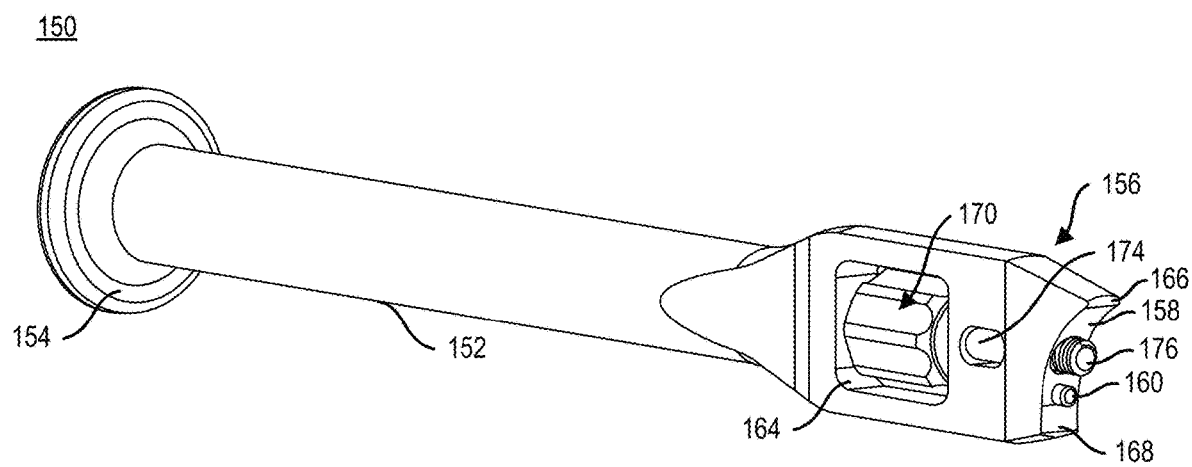
FIG. 10 is a perspective view of the insertion instrument of FIG. 7, in accordance with an aspect of the present invention.

Referring now to FIGS. 7-10, an inserter instrument 150 is shown. The inserter instrument 150 includes a body 152 with a strike plate or impact portion 154 at a first end and a nose portion 156 at a second end. The strike plate 154 provides a surface wider than the body 152 for contacting to force the implant 100 into the correct position between two bone portions. The nose portion 156 includes a contact surface 158 for mating with the implant 100. The contact surface 158 may be, for example, sized and shaped to correspond to the size and shape of the first end 102 of the body 110 of the implant 100. As shown in FIGS. 8-10, the contact surface 158 may be, for example, curved or arced such that the top surface 166 of the nose portion 156 extends past the bottom surface 168 of the nose portion 156. The body 152 may have a width that is larger than the nose portion 156. To provide the variation in width, the second end of the inserter instrument 150 may be, for example, tapered from the body 152 to the nose portion 156.

Referring now to FIG. 8, the nose portion 156 may also include an alignment pin 160, a securement opening 162 and a window 164. The securement opening 162 may extend in a first direction, for example, from the window 164 through the nose portion 156 and out through the contact surface 158. The window 164 may extending through the nose portion 156 in a second direction. The second direction may be relatively perpendicular to the first direction. The alignment pin 160 may be, for example, coupled to and extending out from the contact surface 158 of the nose portion 156. The alignment pin 160 may be positioned below the securement opening 162.

The inserter instrument 150 also includes a securement member 170, as shown in FIGS. 7-10. The securement member 170 includes a shaft 174 with a knob 172 at a first end and a threaded portion 176 at a second end. The securement member 170 is positioned within the body 152, specifically, the shaft 174 passes through the securement opening 162, the threaded portion 176 may extend out beyond the contact surface 158, and the knob 172 may be positioned within the window 164. The threaded portion 176 may couple to corresponding threads in the securement opening 126 of the implant 100.

As shown in FIG. 7, the implant 100 may be secured to the inserter instrument 150 for insertion into a patient. The implant 100 may be coupled by aligning the alignment pin 160 of the inserter instrument 150 with the alignment opening 124, as shown in FIGS. 1 and 6, of the implant 100. Then, the knob 172 of the securement member 170 may be rotated to thread the threaded portion 176 of the securement member 170 into the securement opening 126 of the implant 100. As the knob 172 is rotated, the threaded portion 176 draws the implant 100 towards and into contact with the surface 158. Once the implant 100 is secured to the inserter instrument 150, the implant 100 may be inserted into the patient.

A fastener guide system 200 is depicted in FIGS. 11-17. Once the implant 100 is inserted into a patient's bone, the fastener guide system 200 may be used to insert a fastener 260 across the osteotomy site to strengthen the in vivo construct. The fastener guide system 200 includes an alignment arm 210, a fixation member 230, an insertion guide 240, a temporary fixator 250, and a fastener 260. The alignment arm 210 may include a body 212 with a first arm 214 at a first end and a second arm 218 at a second end. The first arm 214 may be coupled to the first end of the body 212 at an angle with respect to the body 212. The angle may be selected, for example, to allow for insertion of the fastener 260 between the two legs 112, 114 of the implant 100 and to prevent the fastener 260 from contacting the implant 100 during insertion. The second arm 218 may be coupled relatively perpendicular to the second end of the body 212.

In an alternative embodiment, the body 212 may include an opening (not shown) through the body 212 in place of the first arm 214. The opening (not shown) may be, for example, angled to the trajectory desired for inserting the fastener 260 between the two legs 112, 114.

Figure 13:
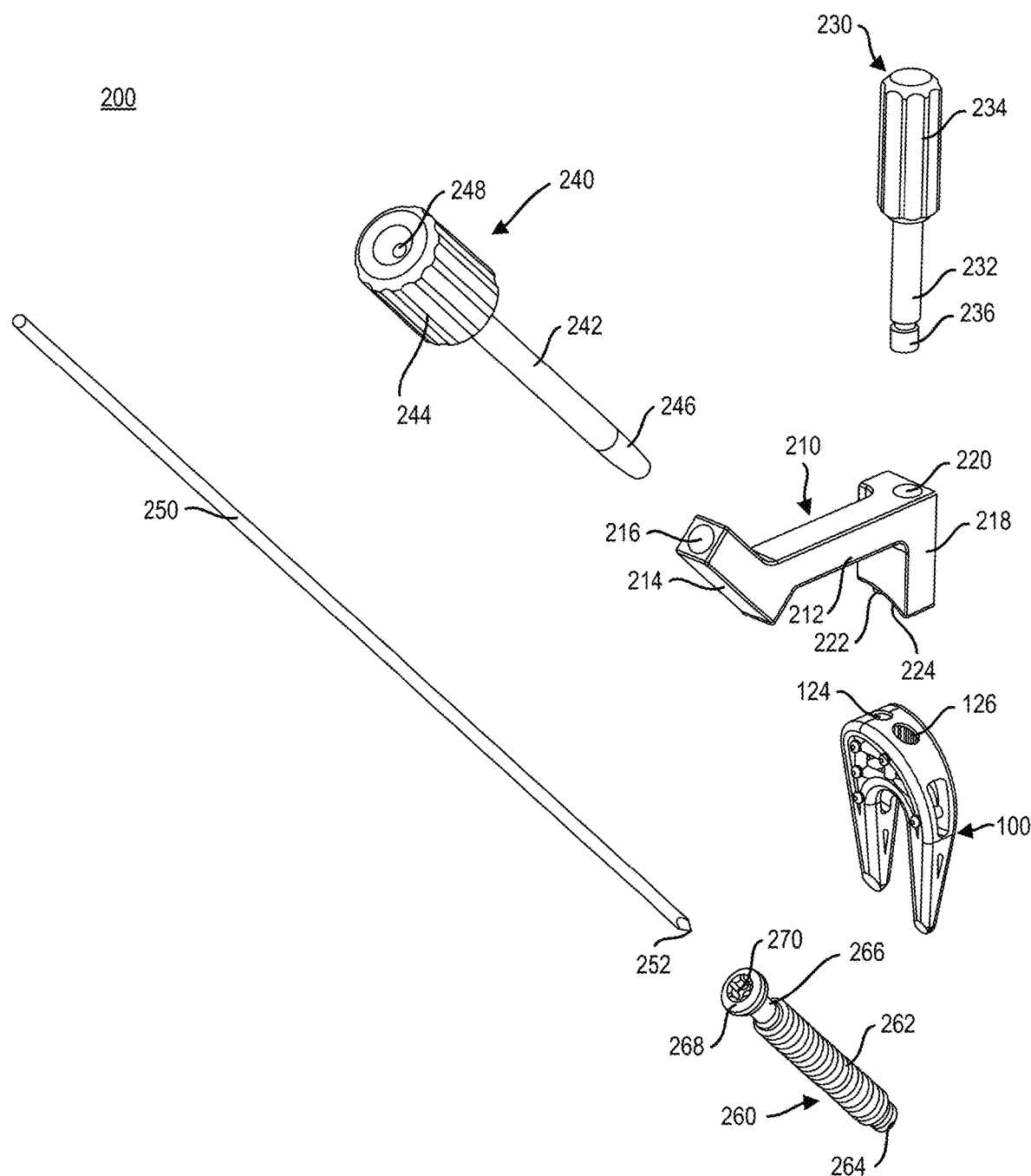
FIG. 13 is an exploded top perspective view of the fastener guide, fastener, and implant of FIG. 11, in accordance with an aspect of the present invention.
Figure 14:
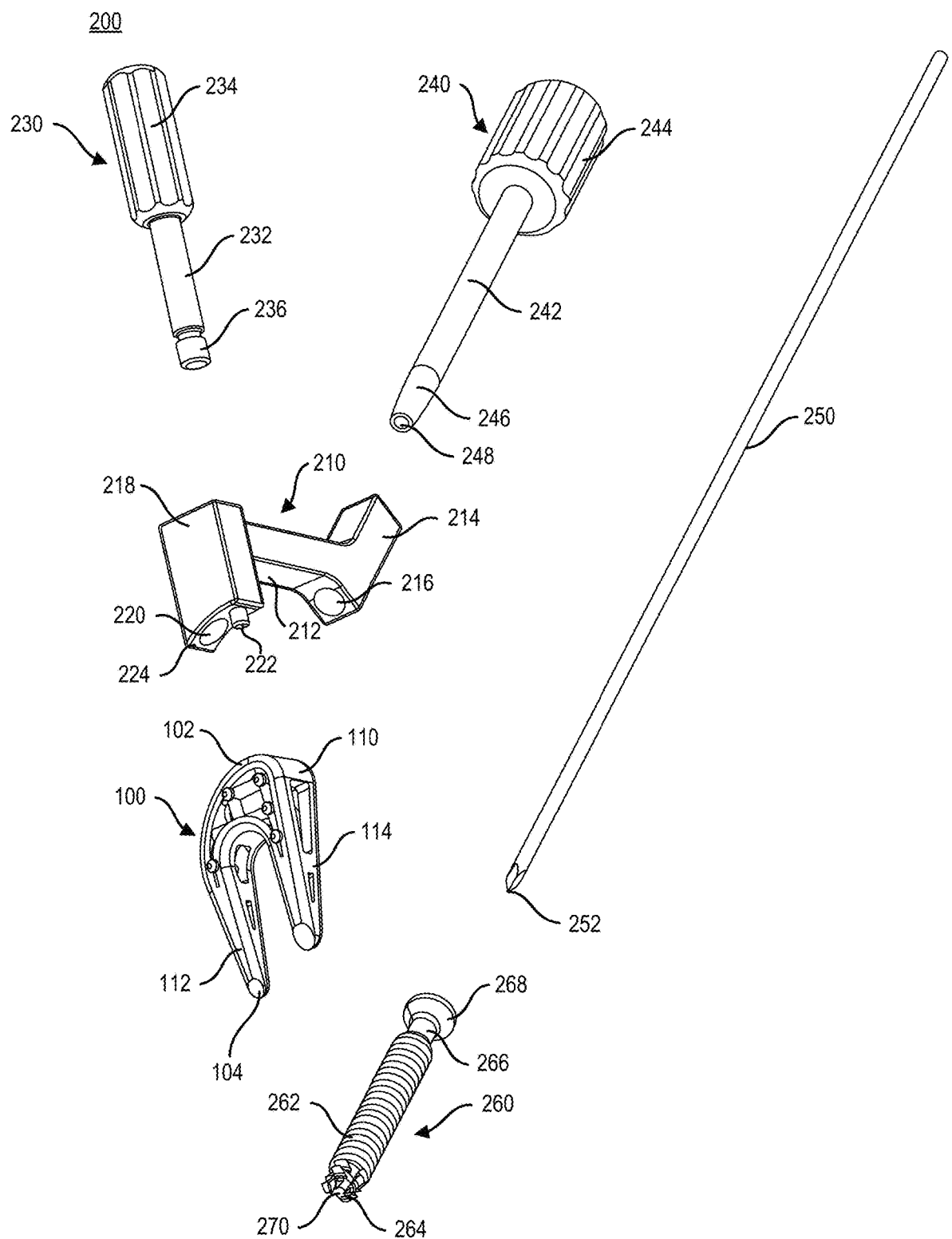
FIG. 14 is an exploded bottom perspective view of the fastener guide, fastener, and implant of FIG. 11, in accordance with an aspect of the present invention.

The first arm 214 may include a temporary fixator guide opening or k-wire guide opening 216 for receiving the insertion guide 240, as shown in FIGS. 13-14. Although not shown, the first arm 214 may include multiple openings 216 positioned at varying angles to provide different trajectory options for the fastener 260. It is also contemplated that the fastener guide system 200 may include multiple alignment arms 210 and each alignment arm 210 may include a first arm 214 positioned at a different angle with respect to body 212 to provide different trajectories for inserting the fastener 260. The insertion guide or k-wire guide 240 may include a base member 242 with a handle portion 244 at a first end and an insertion portion 246 at a second end. The guide 240 may also include an opening 248 extending from the first end to the second end. The opening 248 may be sized and shaped to receive a temporary fixator 250, for example, a k-wire or guide wire. The k-wire 250 may have, for example, a pointed or sharp end 252 to assist with being inserted into and/or through a patient's bone or bones.

The second arm 218 may include an opening 220, an alignment pin 222 positioned adjacent to the opening 220, and an engagement surface 224, as shown in FIGS. 13 and 14. The opening 220 may extend from a top surface of the second arm 218 through to the engagement surface 224 or bottom surface of the second arm 218, as shown in FIGS. 13 and 14. The alignment pin 222, as shown in FIG. 14, is coupled to and extends from the engagement surface 224 of the second arm 218. The alignment pin 222 may be sized and shaped to fit into the alignment opening 124 of the implant 100. The engagement surface 224 may be, for example, sized and shaped or configured to correspond to the size and shape of the first end 102 of the body 110 of the implant 100. As shown in FIGS. 13 and 14, the engagement surface 224 may be, for example, curved or arced. With reference to FIG. 14, the left side of the engagement surface 224 extends further than the right side of the engagement surface 224.

Figure 11:
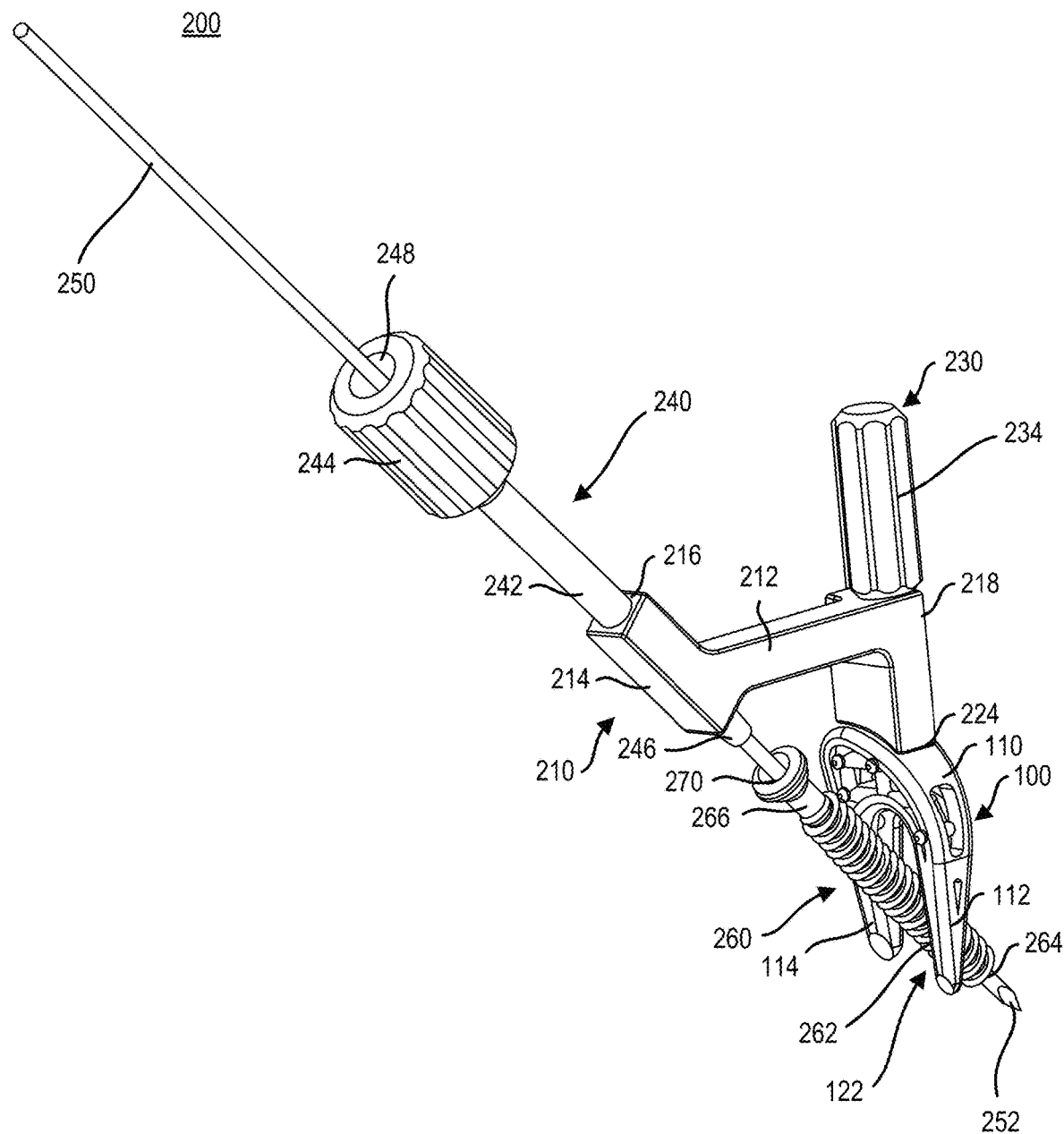
FIG. 11 is a perspective view of one embodiment of a fastener guide, a fastener, and the implant of FIG. 1, in accordance with an aspect of the present invention.
Figure 12:
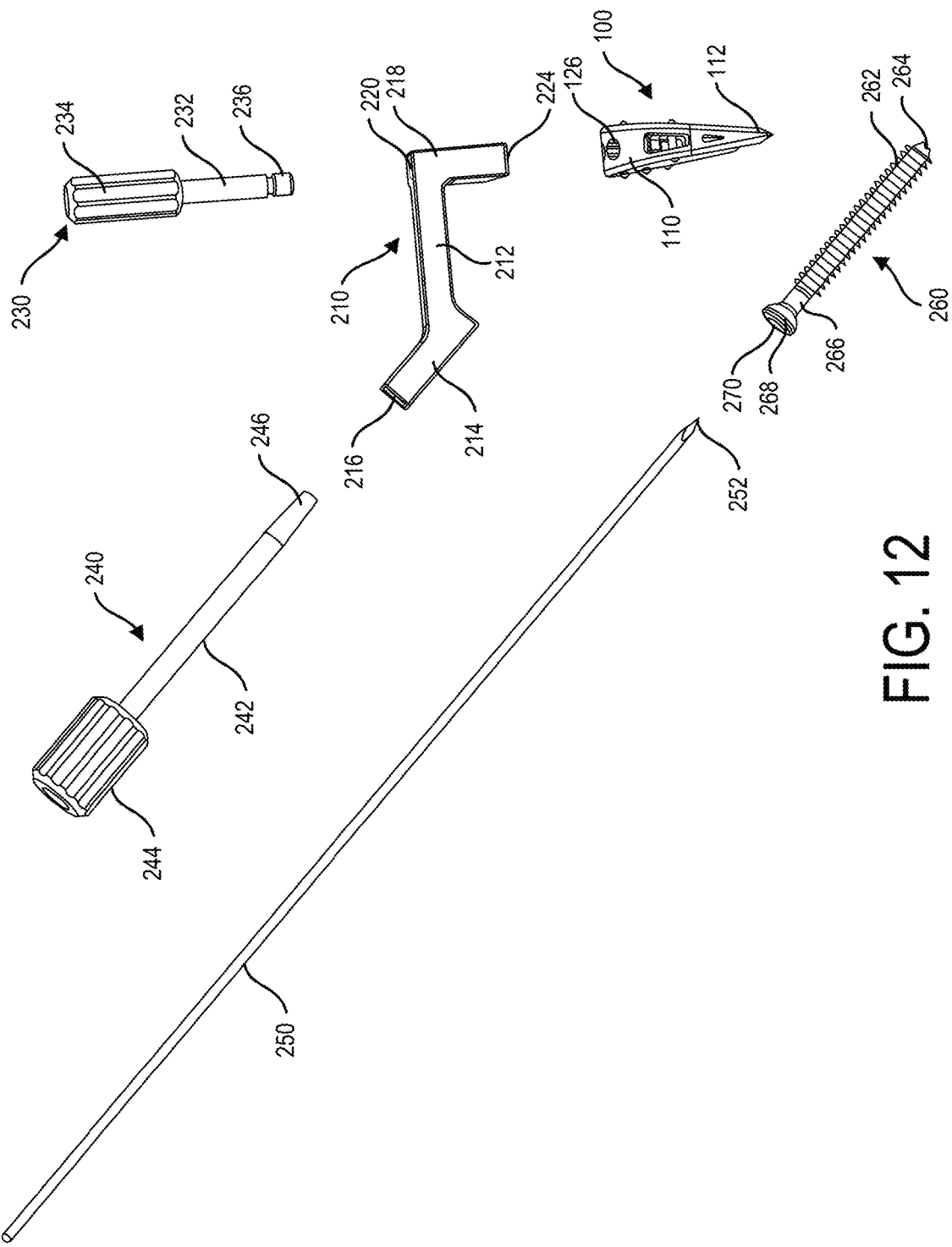
FIG. 12 is an exploded side view of the fastener guide, fastener, and implant of FIG. 11, in accordance with an aspect of the present invention.

The opening 220 of the second arm 218 is sized and shaped or configured to receive the fixation member 230, as shown in FIG. 11. The fixation member 230 includes a shaft 232 with a handle 234 at a first end and a threaded member 236 at a second end. The shaft 232 may be positioned within the opening 220 with the threaded member 236 extending out the bottom of the opening 220 to couple to the implant 100. The threaded member 236 includes threads (not shown) to couple to corresponding threads in the securement opening 126, as shown in FIGS. 12 and 13, of the implant 100 during insertion of the k-wire 250 across the osteotomy site.

Referring now to FIGS. 15-17, an embodiment of the fastener guide system 200 is shown with respect to a portion of a patient's foot 290. The implant 100 has been inserted within the osteotomy site in the patient's medial cuneiform 292, as shown in FIGS. 15 and 16. The alignment arm 210 of the fastener guide system 200 is coupled to the implant 100 by the fixation member 230. The insertion guide 240 is inserted through the first arm 214 of the alignment arm 210 and contacts the patient's foot 290. Next, the temporary fixator 250 is inserted through the opening 248 in the insertion guide 240 and into the bone 292, as shown in FIGS. 15 and 16. The temporary fixator 250 passes through the osteotomy site and implant 100 between the legs 112, 114 of the implant 100. After the k-wire 250 is positioned in the desired orientation in the patient's foot 290, the fixation member 230 may be removed from the implant 100 and the alignment arm 210. Then the insertion guide 240 and alignment arm 210 may be removed and a fastener 260, such as, a cannulated screw or cannulated bone screw, may be inserted over the k-wire 250 and into the patient's foot 290, as shown in FIG. 17. The fastener 260 will be inserted through the channel 122 of the implant 100 between the legs 112, 114 and across the osteotomy site in the medial cuneiform 292.

Figure 18:
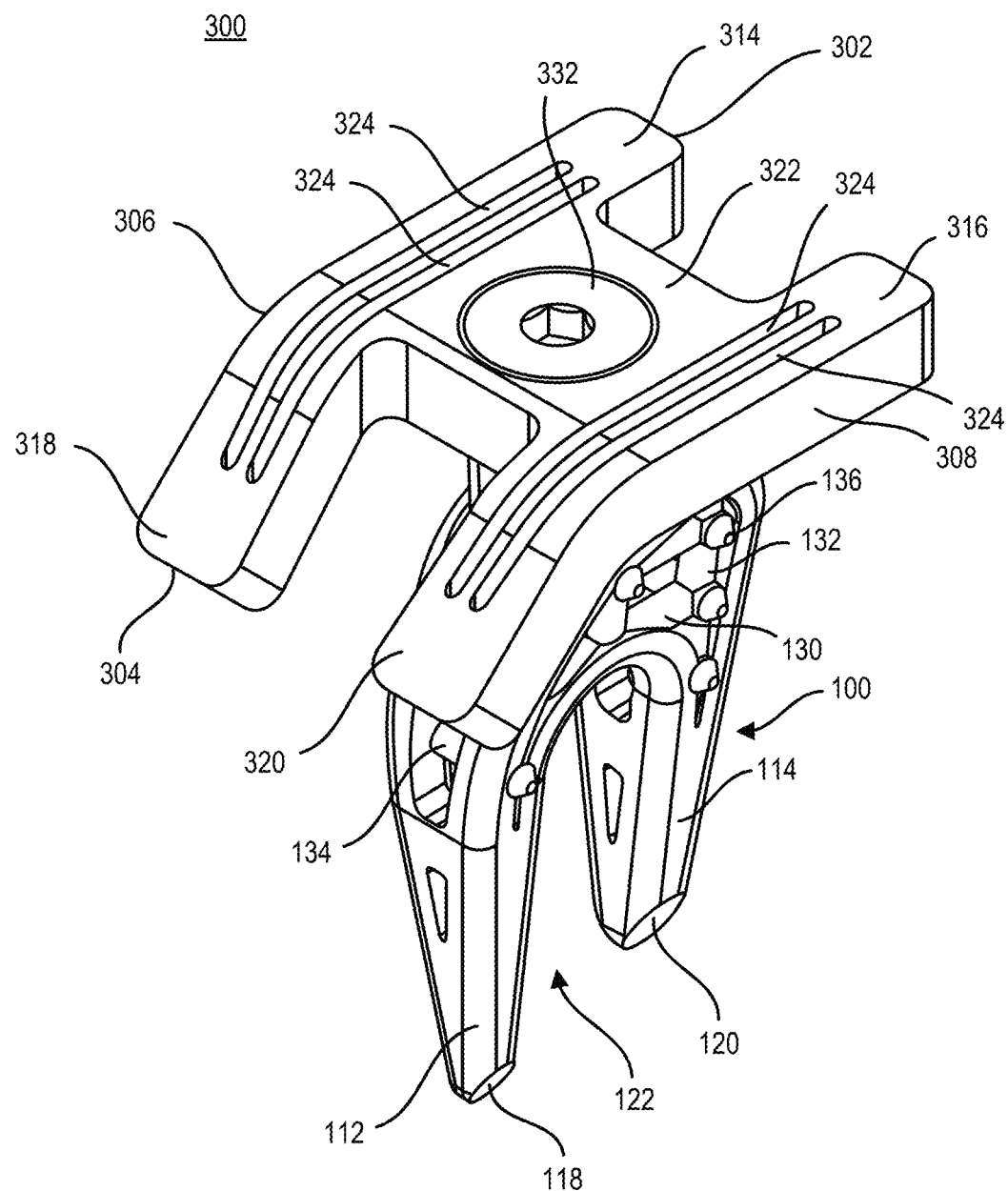
FIG. 18 is a perspective view of one embodiment of a resection guide and the implant of FIG. 1, in accordance with an aspect of the present invention.
Figure 19:
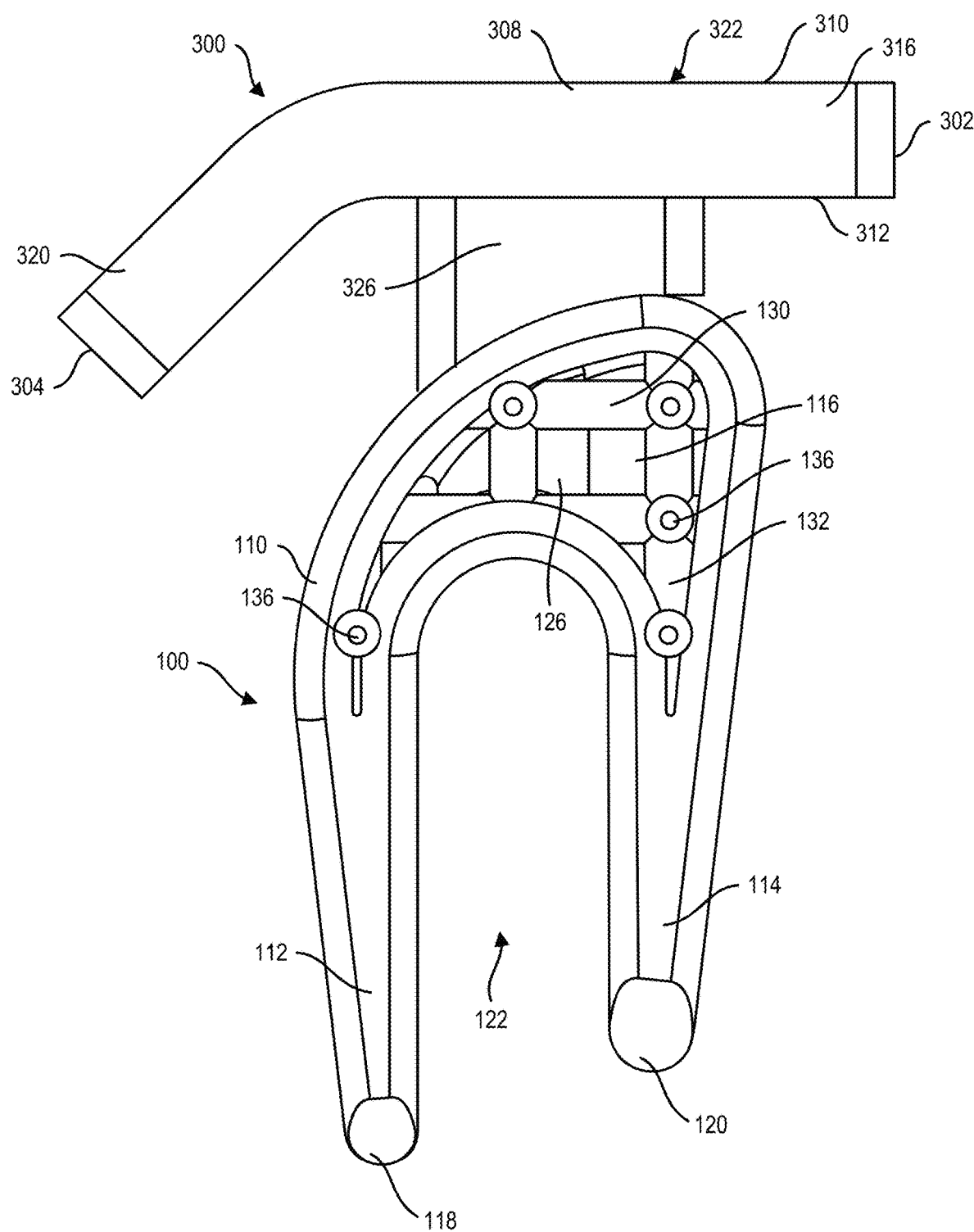
FIG. 19 is a distal view of the resection guide and implant of FIG. 18, in accordance with an aspect of the present invention.
Figure 20:
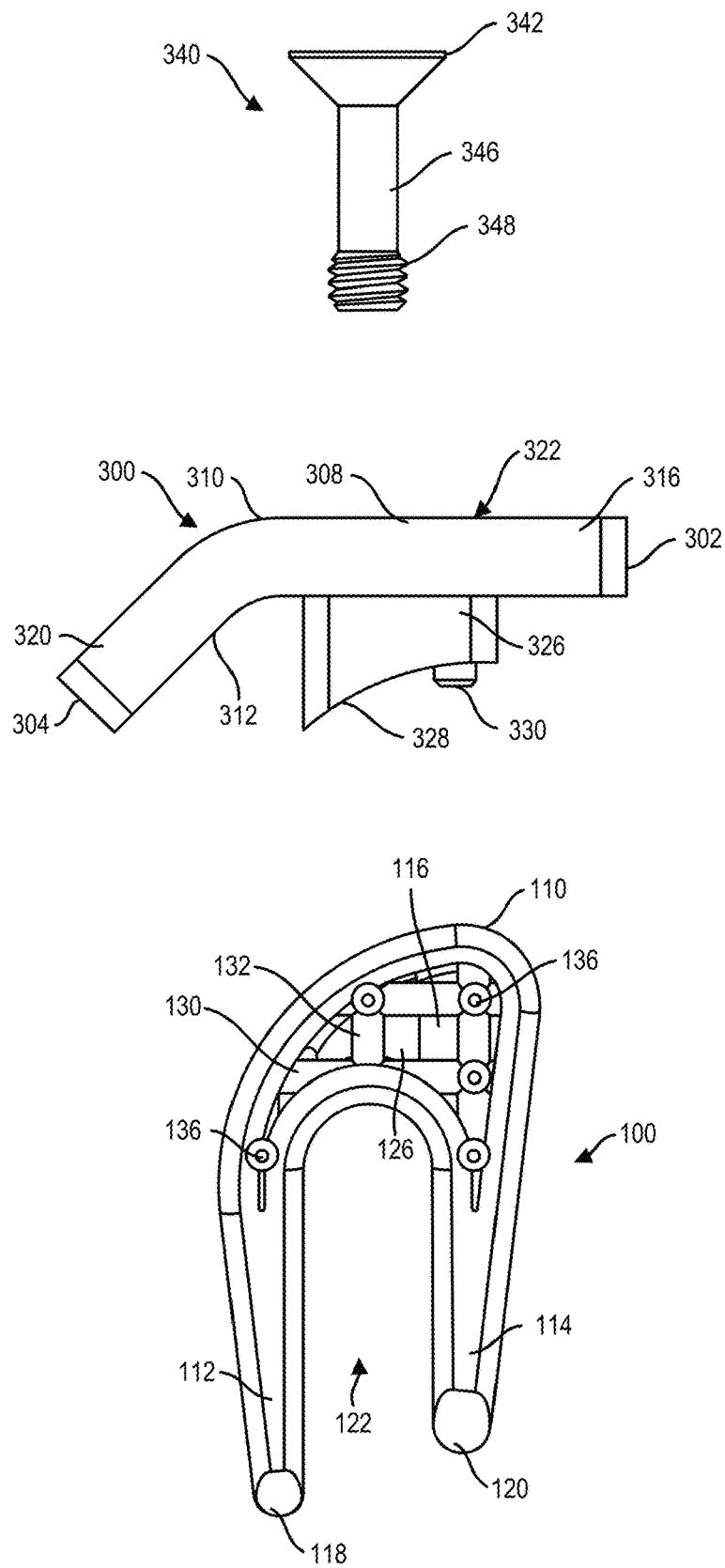
FIG. 20 is an exploded distal view of the resection guide and implant of FIG. 18, in accordance with an aspect of the present invention.
Figure 25:
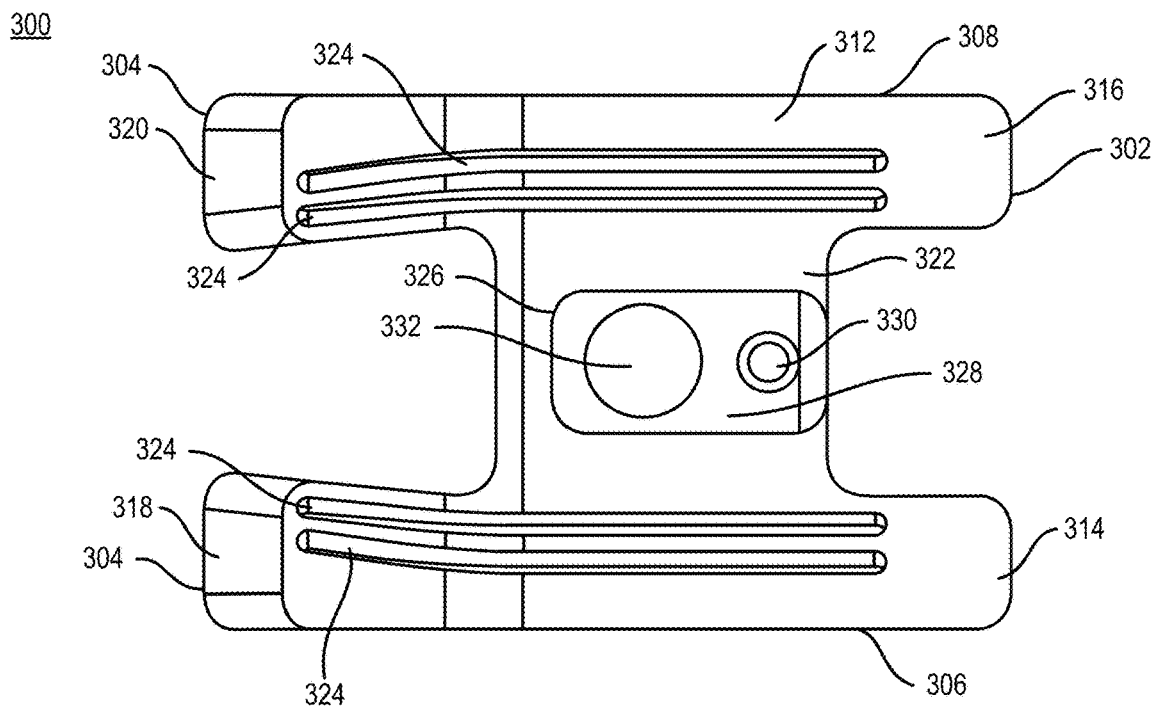
FIG. 25 is a bottom view of the resection guide of FIG. 21, in accordance with an aspect of the present invention.
Figure 26:
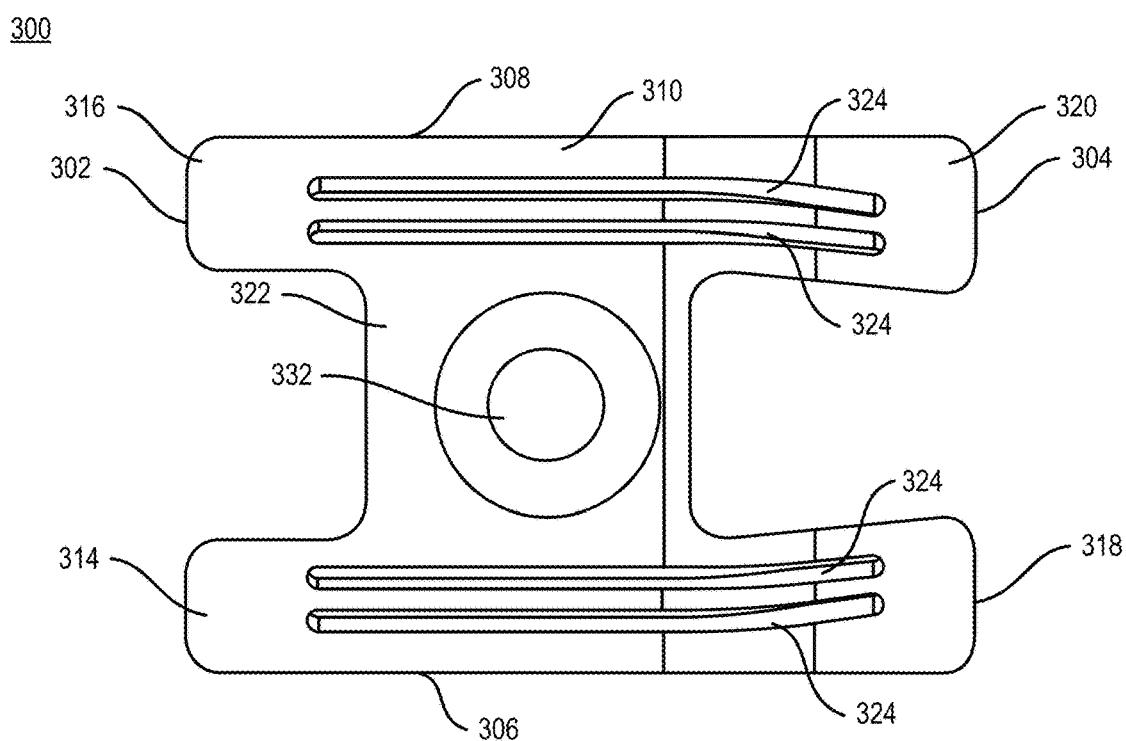
FIG. 26 is a top view of the resection guide of FIG. 21, in accordance with an aspect of the present invention.
Figure 29:
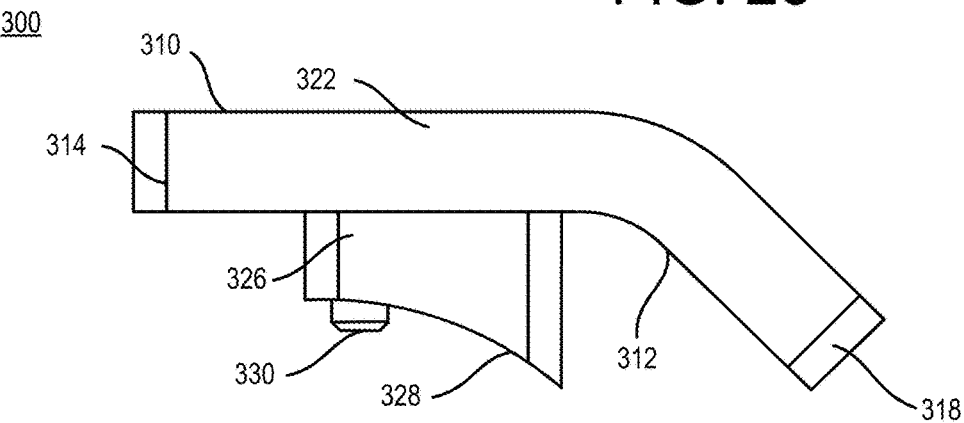
FIG. 29 is a front view of the resection guide of FIG. 21, in accordance with an aspect of the present invention.

Referring now to FIGS. 18-29, a resection guide 300 is shown. The resection guide 300 may have a first end 302 opposite a second end 304, a first side 306 opposite a second side 308, and a top surface 310 opposite a bottom surface 312. The resection guide 300 may also have a first arm 314, a second arm 316, a first leg 318 and a second leg 320. The arms 314, 316 may extend out from the first end 302 of the resection guide 300. The first arm 314 is positioned on the first side 306 of the resection guide 300 and the second arm 316 is positioned on the second side 308 of the resection guide 300. The first and second arms 314, 316 are spaced apart to form a passage between the arms 314, 316. As shown in FIGS. 25-26, the arms 314, 316 are positioned generally perpendicular to each other. As shown in FIGS. 19, 20 and 29, the arms 314, 316 are aligned with the central portion 322 of the resection guide 300.

Figure 27:
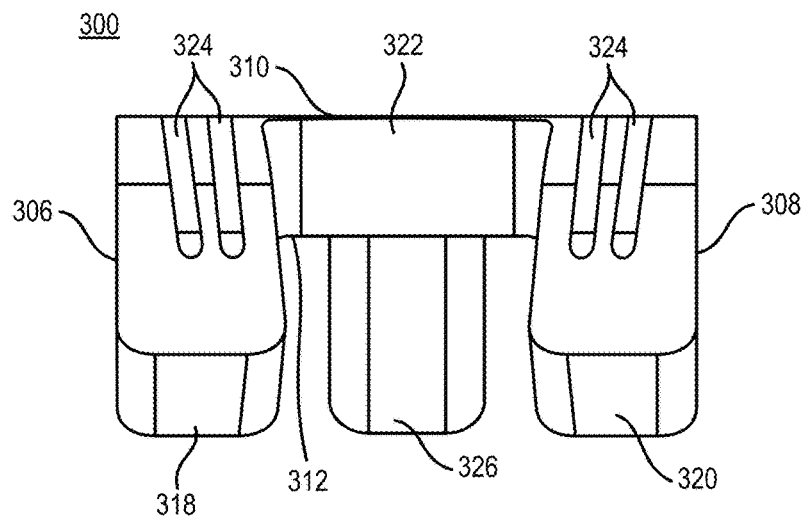
FIG. 27 is a first side view of the resection guide of FIG. 21, in accordance with an aspect of the present invention.
Figure 28:
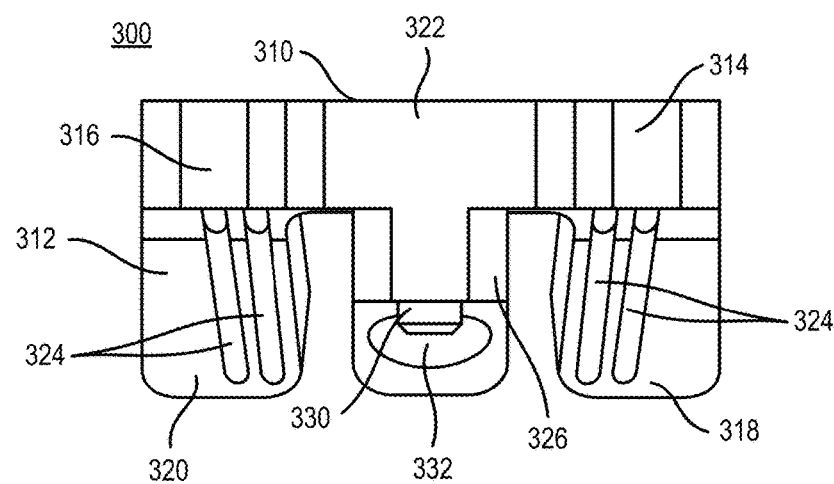
FIG. 28 is a second side view of the resection guide of FIG. 21, in accordance with an aspect of the present invention.

As shown in FIGS. 18-29, the legs 318, 320 may extend out from the second end 304 of the resection guide 300. The first leg 318 is positioned on the first side 306 of the resection guide 300 and the second leg 320 is positioned on the second side 308 of the resection guide 300. The first and second legs 318, 320 are spaced apart to form a passage between the legs 318, 320. As shown in FIGS. 25-27, the interior surfaces of the legs 318, 320 are angled with respect to each other and converge towards a center or the longitudinal axis of the resection guide 300. The legs 318, 320 are also angled with respect to the central portion 322 of the resection guide 300 in dorsal-plantar direction, as shown in FIGS. 19, 20, and 29. The legs 318, 320 are angled away from the top surface 310 of the central portion 322 as they extend from the central portion 322.

The resection guide 300 may also include at least two slots 324, as shown in FIGS. 18 and 21-28. The slots 324 may be sized and shaped to receive a saw blade (not shown), for example, a sagittal saw blade, to cut the patient's bone 292 and remove the implant 100. At least one first slot 324 may extend along the first side 306 and through at least a portion of the first arm 314, the central portion 322 and at least a portion of the first leg 318. In the depicted embodiment, the at least one first slot 324 is two slots 324. At least one second slot 324 may extend along the second side 308 and through at least a portion of the second arm 316, the central portion 322 and at least a portion of the second leg 320. In the depicted embodiment, the at least one second slot 324 is two slots 324. The slots 324 may be angled as they extend from the top surface 310 to the bottom surface 312. The slots 324 may be angled toward the center or a longitudinal axis of the resection guide 300. The angle of the slots 324 may correspond to the angle of the proximal and distal sides of the implant 100.

Figure 21:
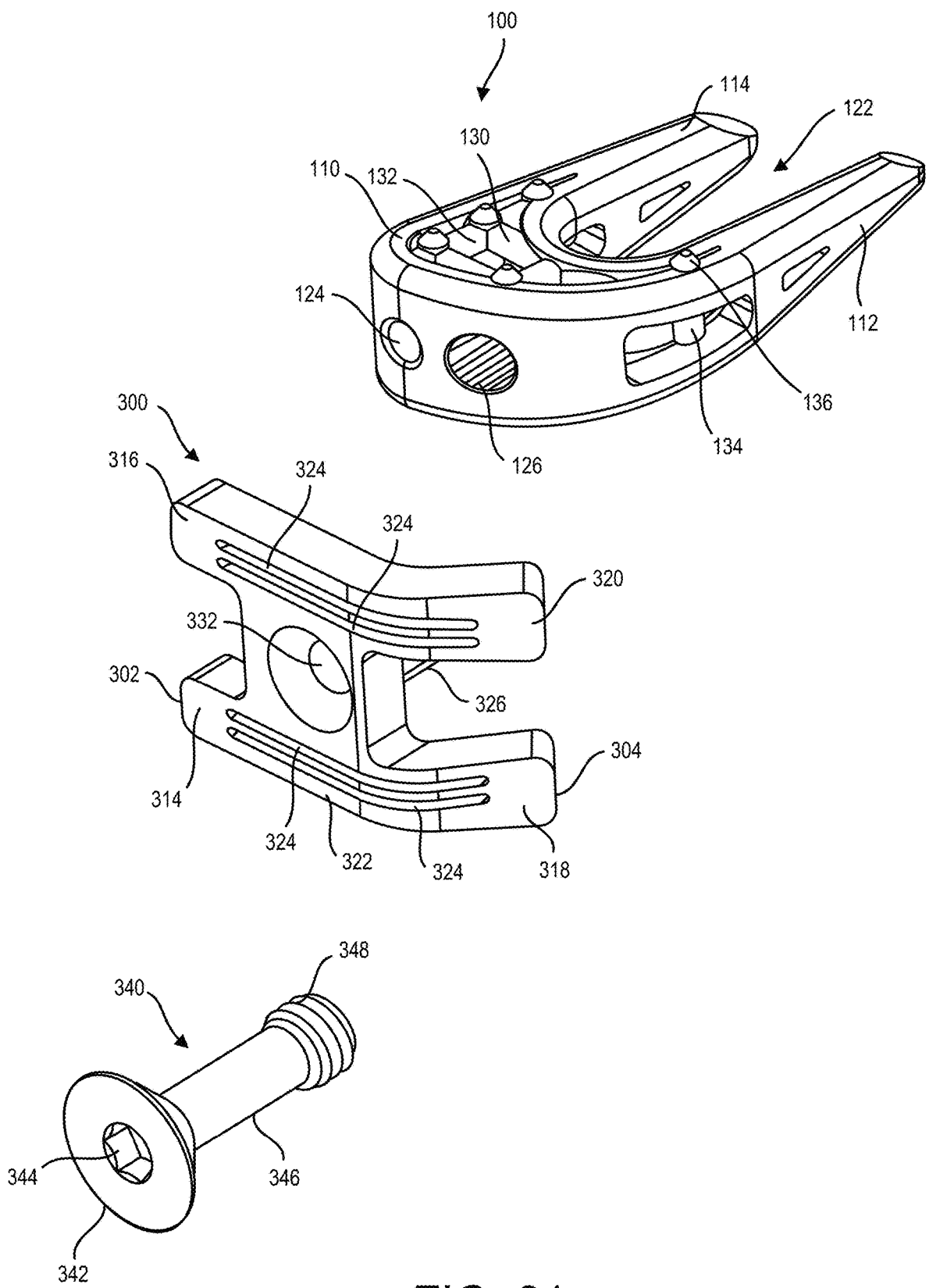
FIG. 21 is an exploded top perspective view of the resection guide and implant of FIG. 18, in accordance with an aspect of the present invention.
Figure 22:
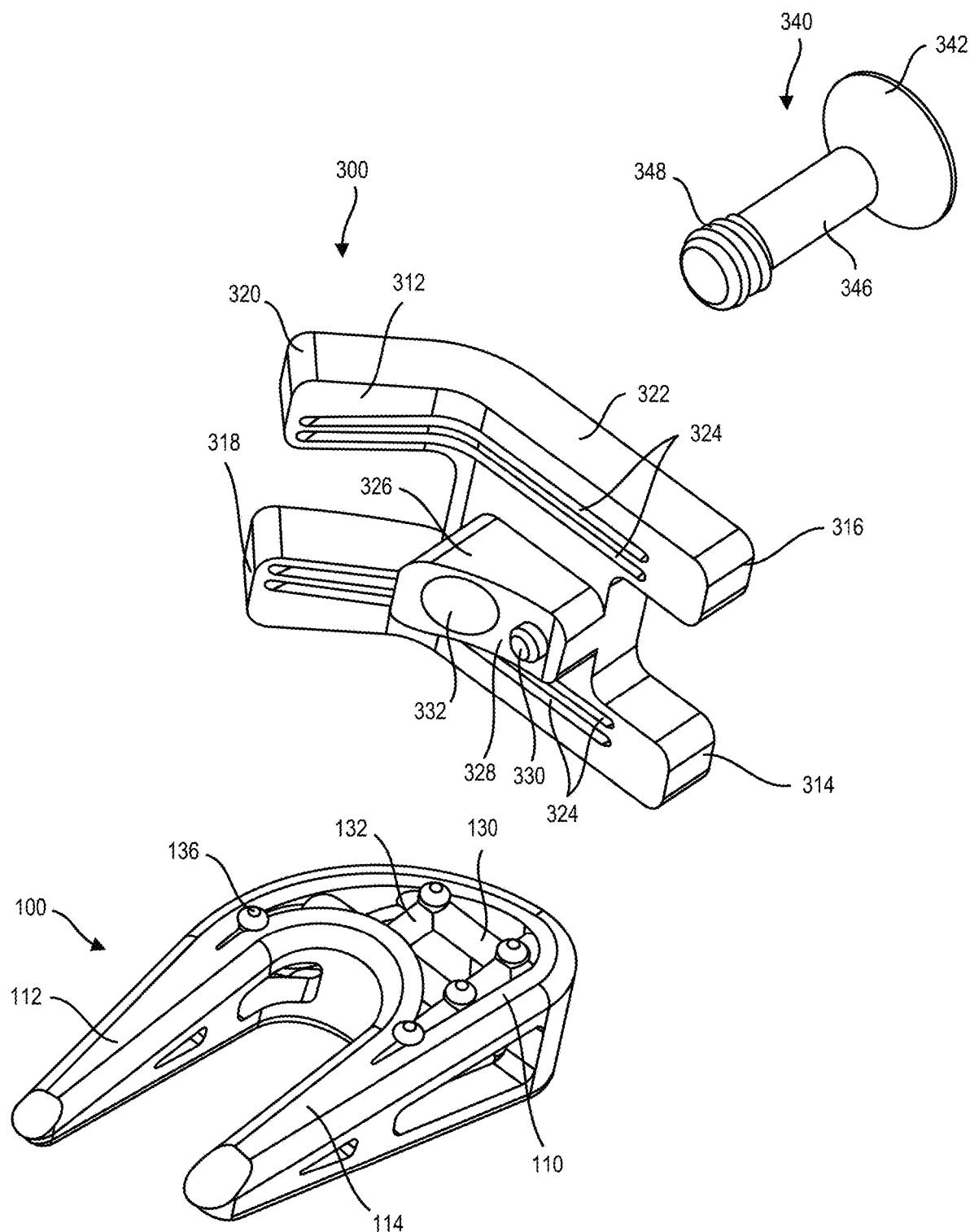
FIG. 22 is an exploded bottom perspective view of the resection guide and implant of FIG. 18, in accordance with an aspect of the present invention.
Figure 23:
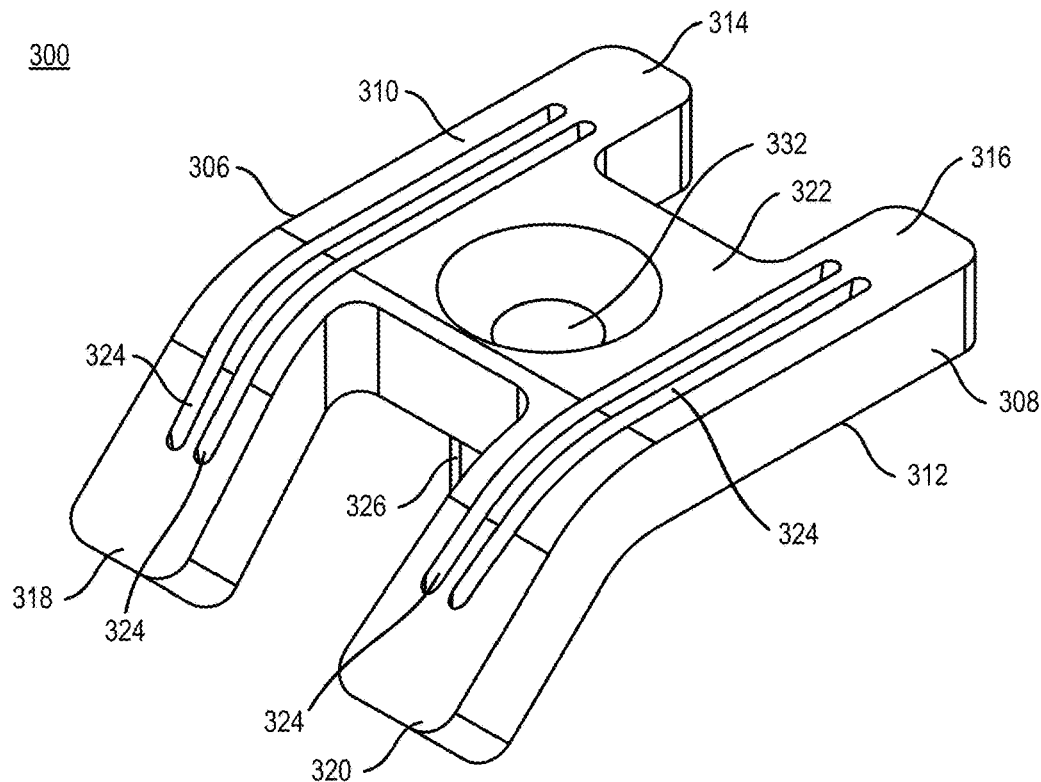
FIG. 23 is a top perspective view of the resection guide of FIG. 21, in accordance with an aspect of the present invention.
Figure 24:
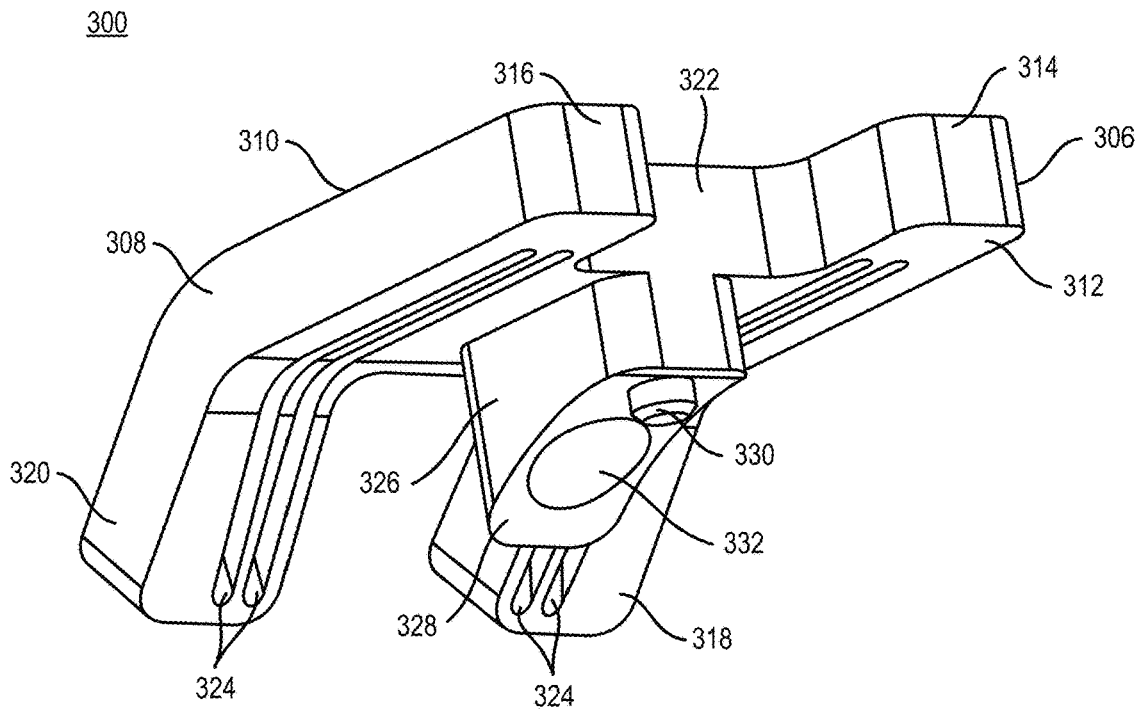
FIG. 24 is a bottom perspective view of the resection guide of FIG. 21, in accordance with an aspect of the present invention.

As shown in FIGS. 20-22, the resection guide 300 may also include a fastener 340 for securing the resection guide 300 to the implant 100. The fastener 340 may include a head portion 342 at a first end and a shaft 346 at a second end. The head portion 342 may include, for example, a driver opening 344 for receiving a tool to rotate the fastener 340 to engage the securement opening 126 of the implant 100. The shaft 346 may include a threaded end 348 with threads that correspond to the threads in the securement opening 126. As the fastener 340 is inserted through the opening 332 in the resection guide 300, the threaded end 348 may engage the securement opening 126 in the implant 100. The opening 332 may include a retaining member or mechanism (not shown). The retaining member allows the threaded end 348 of the fastener 340 to pass through the opening 332 for coupling to the implant 100, but prevents the fastener 340 from accidentally disengaging from the opening 332 in the resection guide 300. The retaining member may be, for example, an internal thread (not shown) to allow for the threaded end 348 to be threaded through the opening 332 for engagement with the implant 100. A threaded retaining member would also allow for the fastener 340 to be removed and replaced if, for example, the threads on the threaded end 348 started wear away. Once the fastener 340 is completely tightened into the implant 100, the head portion 342 of the fastener 340 will be, for example, flush with a top surface 310 of the resection guide 300 or recessed into the center portion 322 of the resection guide 300, as shown in FIG. 18.

Figure 30:
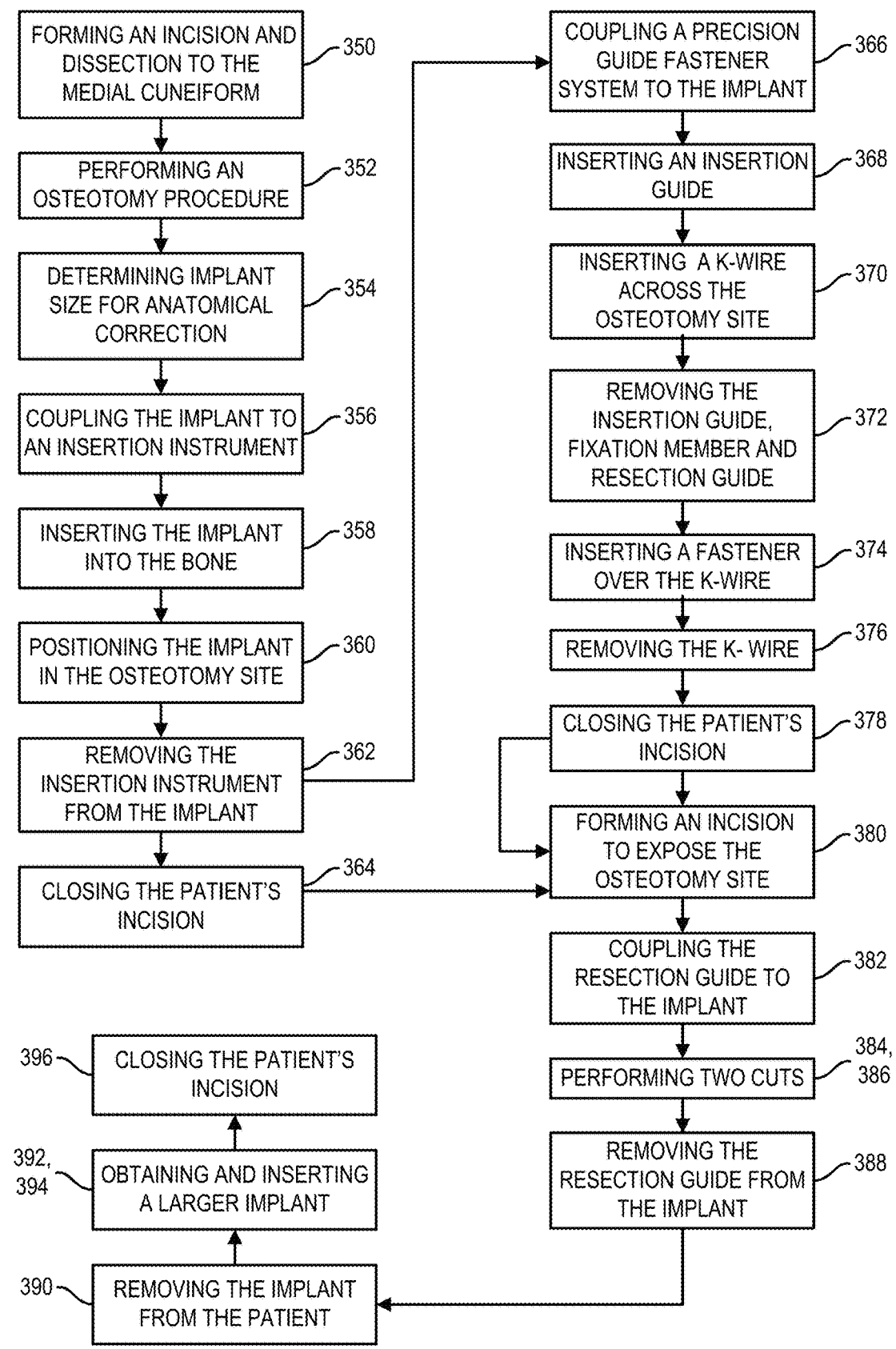
FIG. 30 depicts one embodiment of a surgical method for performing a Cotton osteotomy, in accordance with an aspect of the present invention.

A surgical method of correcting bone deformities is shown in FIG. 30. The method includes, for example, performing a Cotton osteotomy on the dorsal and medial aspects of the foot 290, as shown in FIGS. 15-17. A Cotton osteotomy is performed for planovalgus deformity correction to correct forefoot varus and to reestablish arch height in a patient's flatfoot deformity. The Cotton osteotomy is performed by creating a cut in the medial cuneiform 292 to allow for a graft or implant to be inserted, forming an opening wedge to reestablish the foot arch. Once the osteotomy is made, an implant 100 with a dorsal to plantar taper is inserted into the medial cuneiform 292 to reestablish the patient's arch.

In an embodiment, the method may include making a skin incision and dissection down to the medial cuneiform with a dorsomedial approach 350. Next, the method may include locating the osteotomy site and using a saw to cut through the bone 352. The cut may be made parallel to the first metatarsal cuneiform joint. Once the cut is made, trial sizers may be inserted into the cut to determine the appropriate sized implant for the desired anatomical correction 354. The trial sizers may match the geometry of the available implants to allow for selection of the implant that provides the required correction. After the implant size is selected, the implant is coupled to the insertion instrument 356. The implant may be coupled to the insertion instrument as described in greater detail above with reference to FIGS. 7-10. The implant 100 may then be inserted into the medial cuneiform 358, and if necessary, the end of the insertion instrument is impacted to correctly position the implant into the osteotomy site 360. Once the implant is inserted, the inserter instrument is removed from the implant 362, and if no additional procedures are to be performed, the patient's incision may be closed 364.

Optionally, the method may also include inserting a fastener across the osteotomy site and through the implant to strengthen the construct. The fastener may be inserted by first coupling a guide fastener system to the implant using a fixation member 366, as described in greater detail above with reference to FIGS. 11-14. Next, an insertion guide is inserted through the guide fastener system at the desired fastener trajectory 368. A k-wire is then inserted through the insertion guide and advanced across the osteotomy site 370. After the k-wire is inserted, the insertion guide, fixation member, and the guide fastener system are removed 372. Then, a fastener, such as a cannulated bone screw, is inserted over the k-wire and advanced across the osteotomy site through the implant 374. Once the fastener reaches the desired position, the k-wire is removed 376. Finally, the patient's incision may be closed 378.

The method may also optionally include a resection procedure, if the implant needs to be removed for a revision surgery. The removal method may include exposing the osteotomy site via a normal skin incision and soft tissue dissection 380. If a cannulated screw was inserted across the osteotomy site, the screw will be removed prior to making the cuts to remove the implant. The removal method may also include, obtaining a resection guide and attaching the resection guide to the implant 382, as described above with reference to FIGS. 18-22. Next, a saw blade, for example, a sagittal saw blade, is inserted through the selected first slot based on the size of the implant and the bone surrounding the implant is cut 384. The resection guide includes leg portions that are bent to position the slots in the leg portions to allow for the cutting of the medial side of the medial cuneiform and for access to cut around the entire implant. After the first cut is made, the saw blade is inserted through the selected second slot corresponding to the selected first slot 386. After the two cuts are made, the resection guide may be detached from the implant 388 and the implant is removed from the osteotomy site in the patient's foot 390. Alternatively, the coupled implant and resection guide may be removed from the osteotomy site in the patient's foot, then the implant may be detached from the resection guide. Once the old implant is removed, a larger implant, for example, an implant two sizes larger than the original implant, may be selected 392 and the new implant inserted into the osteotomy site 394. After the osteotomy procedure is complete, the incision may be closed 396.

Referring now to FIGS. 31-65, another embodiment of an implant kit is illustrated. In one embodiment, the implant kit may include a first implant 400 (See FIGS. 31-36), a second implant 450 (See FIGS. 37-42), an insertion instrument 500, a fastener guide system 600, and a resection guide system 700. As shown in FIGS. 31-36, the first implant 400 may include a first end 402, a second end 404, a top side 406 and a bottom side 408. The first implant 400 may include a body or frame 410 with a first leg or projection 412, a second leg or projections 414, and an opening 416. The opening 416 extends through the body 410 from a proximal side to a distal side of the implant 400. The first leg 412 may be positioned on the top 406 and the second leg 414 may be positioned on the bottom 408. In the depicted embodiment, the first leg 412 may have, for example, a curved exterior surface as the first leg 412 extends from the first end 402 to the second end 404. The second leg 414 may have, for example, an angled exterior surface as the second leg 414 extends from the first end 402 to the second end 404. The ends or tips 418, 420 of the legs 412, 414, respectively, may be, for example, tapered or otherwise shaped (See FIG. 34) to aide in the insertion into a patient's bone. The legs 412, 414 may be spaced apart to form a channel 422 between the legs 412, 414. As discussed in greater detail below, the channel 422 may be configured or sized and shaped to allow for a fastener, for example, a bone screw to pass through the channel 422 and across the osteotomy site.

Figure 31:
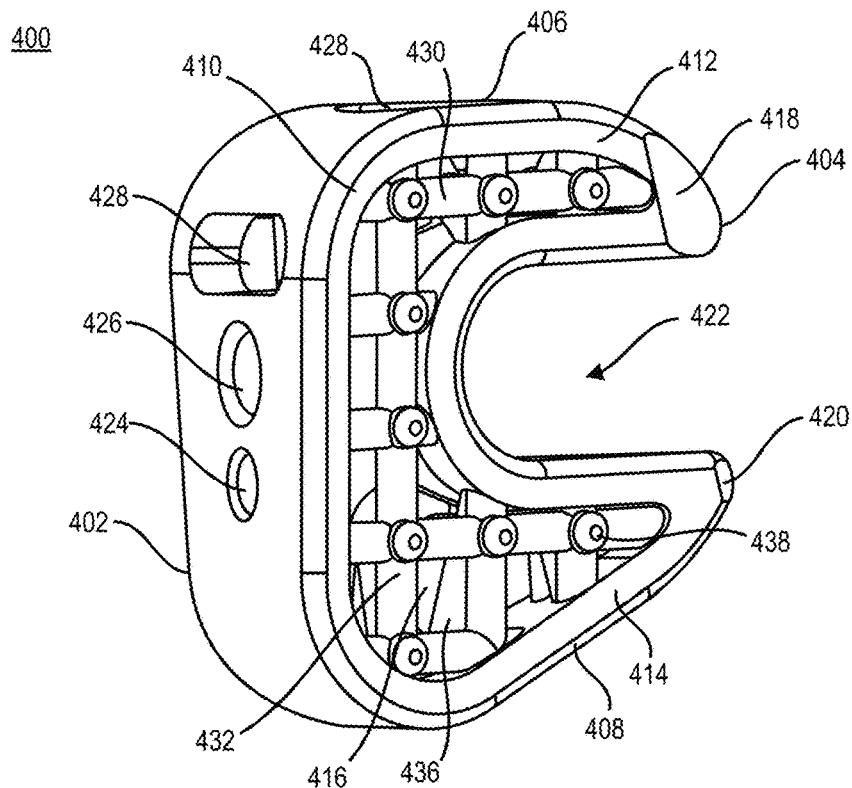
FIG. 31 is a perspective view of another embodiment of an implant, in accordance with an aspect of the present invention.

The first end 402 of the body 410 may be, for example, planar with curved or angled edges positioned between the first end 402 and each of the legs 412, 414, as shown in FIGS. 31 and 32. The exterior surface of the planar with curved or angled edges first end 402 of the body 410 may have a shape corresponding to a patient's calcaneus bone 692. The surface of the first end 402 may be, for example, smooth. The first end 402 of the body 410 may also have a width extending from the proximal surface to the distal surface. The implant 400 may have body widths of, for example, approximately 6 mm to approximately 12 mm. The width of the implant 400 may be selected based on the desired correction. The body 410 may also have a dorsal to plantar taper, for example, a taper from the top 406 to the bottom 408 of the implant 400 (See FIG. 34). The dorsal to plantar taper may allow for a reduction in plantar ligament stress. In addition, the body 410 may have a medial to lateral taper, for example, a taper from the first end 402 to the second end 404 (See FIG. 35). The medial to lateral taper may allow for lateral column lengthening. The dorsal to plantar taper and the medial to lateral taper form an implant 400 with bi-planar bone contacting surfaces. Each leg 412, 414 may have an end 418, 420, respectively. The ends 418, 420 of the implant 400 may be, for example, further tapered to form a sharp angle or point at each end 418, 420.

Figure 33:
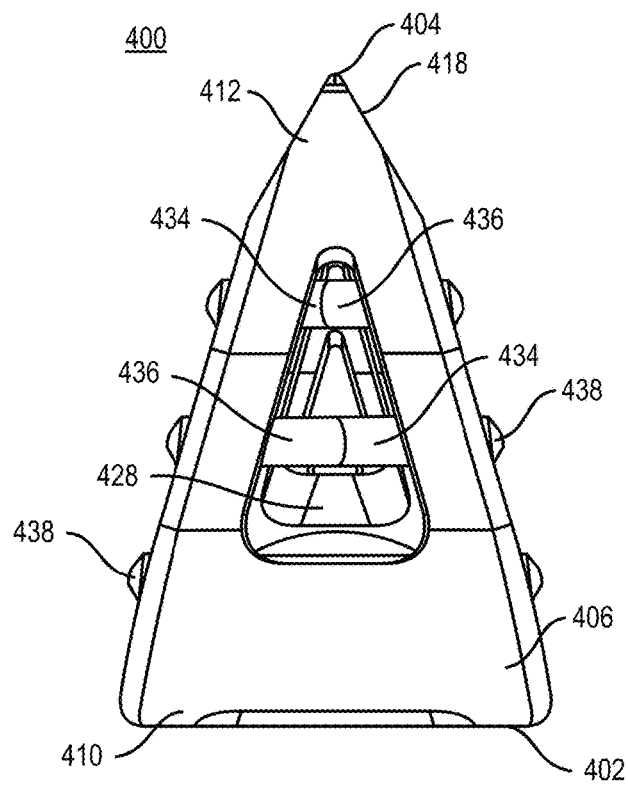
FIG. 33 is a top view of the implant of FIG. 31, in accordance with an aspect of the present invention.
Figure 34:
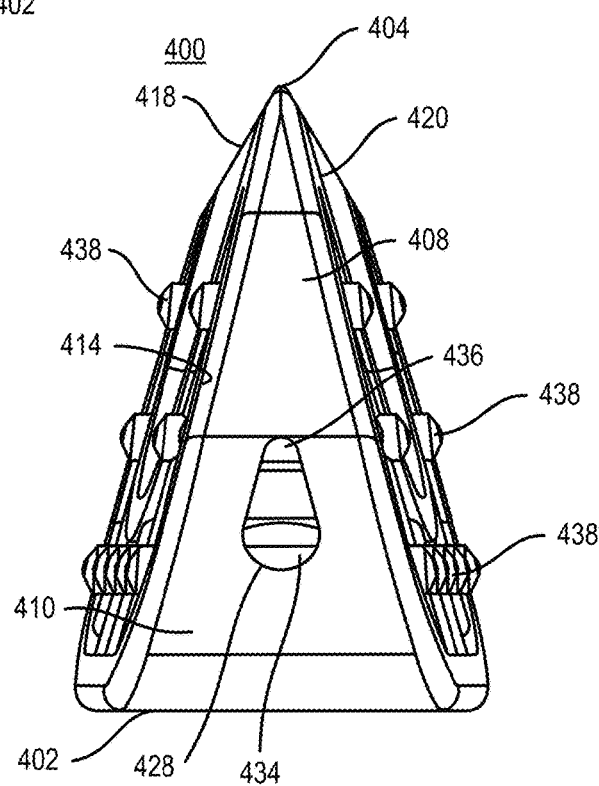
FIG. 34 is a bottom view of the implant of FIG. 31, in accordance with an aspect of the present invention.
Figure 35:
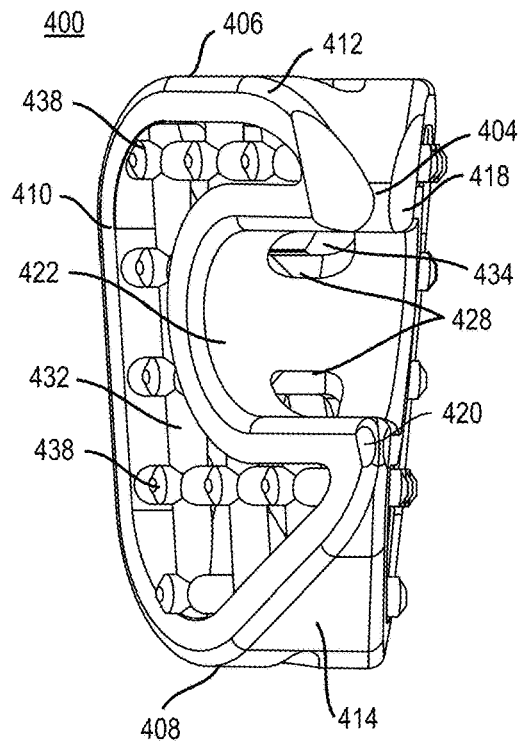
FIG. 35 is a first side view of the implant of FIG. 31, in accordance with an aspect of the present invention.
Figure 36:
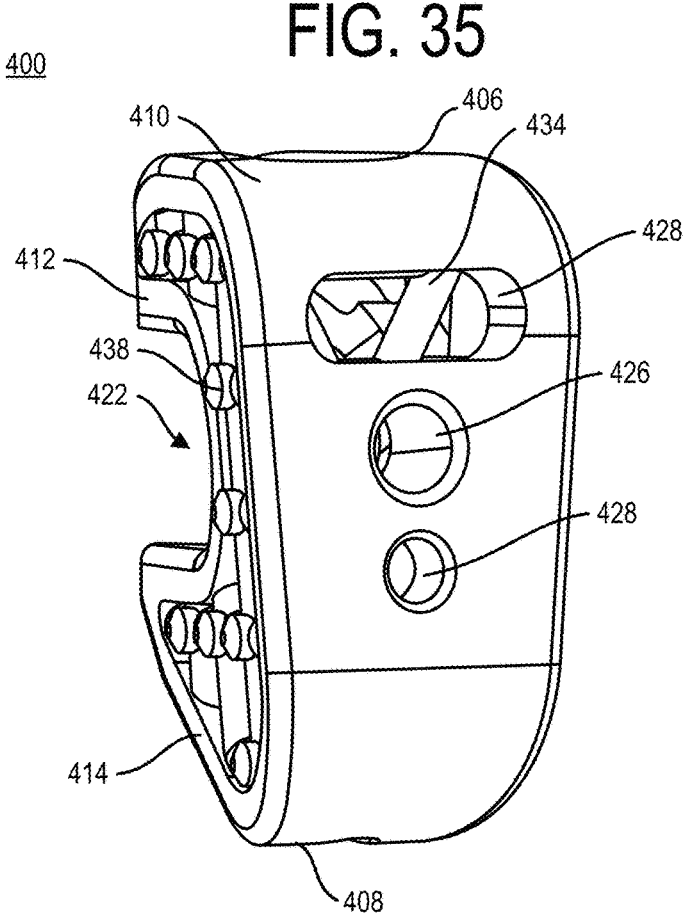
FIG. 36 is a second side view of the implant of FIG. 31, in accordance with an aspect of the present invention.

As shown in FIGS. 31 and 36, the first end 402 of the body 410 may also include an alignment opening 424 and a securement opening 426. The alignment opening 424 may be positioned adjacent to the securement opening 426 on the first end 402 of the implant 400. The alignment opening 424 may be, for example, configured or sized and shaped to receive an alignment pin from the insertion instrument 500, a guide system 600 and/or a resection guide system 700, as described in greater detail below. The alignment opening 424 may, for example, extend into a portion of the opening 416 in the body 410 at the first end 402 of the implant 400. The securement opening 426 may be, for example, threaded to receive a fastener to couple the implant 400 to an insertion instrument 500, a guide system 600 and/or a resection guide system 700, as described in greater detail below. The securement opening 426 may be, for example, threaded to engage the threads on a fastener. The securement opening 426 may, for example, extend into the first end 402 of the body 410, through the opening 416, and into at least a portion of the body 410 at the bottom of the channel 422. The securement opening 426 extends farther into the implant 400 than the alignment opening 424. The body 410 may also include at least one window or opening 428 on the first end 402, as shown in FIGS. 31 and 36, the top surface 406, as shown in FIG. 33, the bottom surface 408, as shown in FIG. 34, and the surface at the bottom of channel 422, as shown in FIG. 35. The windows 428 may extend from an exterior surface of the implant 400, through the body wall 410, and into the opening 416. The windows 428 may be, for example, sized and shaped or configured to allow for bone growth and cross-communication of blood within the osteotomy site.

Figure 32A:
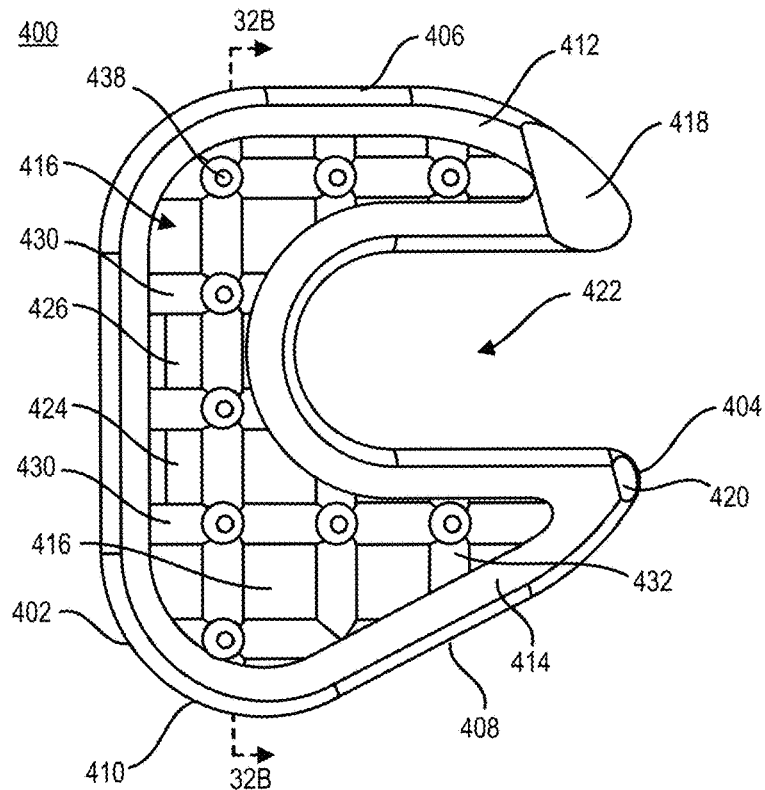
FIG. 32A is a front view of the implant of FIG. 31, in accordance with an aspect of the present invention.
Figure 32B:
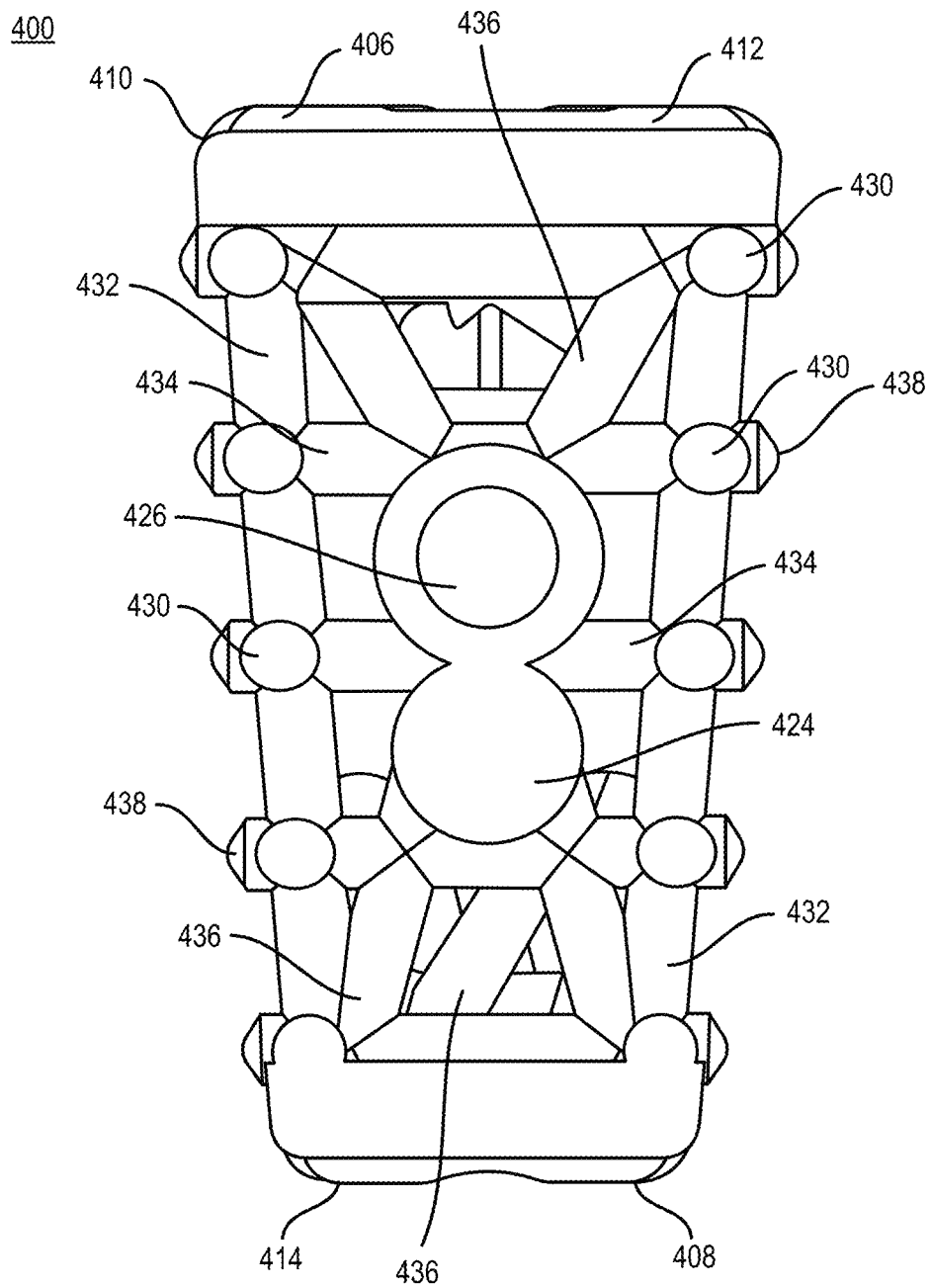
FIG. 32B is a cross-sectional view taken along line 32B-32B in FIG. 32A, in accordance with an aspect of the present invention.

As shown in FIGS. 31, 32A and 32B, the opening 416 may include, a plurality of struts or linear members, 430, 432, 434, 436 extending across the opening 416 and coupled to the body 410. The plurality of struts 430, 432, 434, 436 may include, for example, a first set of struts 430, a second set of struts 432, a third set of struts 434, and a fourth set of struts 436. The first set of struts 430 may extend, for example, in a medial-lateral direction, as shown in FIGS. 31 and 32A. The second set of struts 432 may extend, for example, in a dorsal-plantar direction, as also shown in FIGS. 31, 32A and 32B. The third set of struts 434 may extend, for example, in a proximal-distal direction, as shown in FIGS. 32B, 33 and 34, forming a three dimensional matrix within the opening 416. The third set of struts 434 may be positioned perpendicular to the first set of struts 430 and the second set of struts 432. The opening 416 may also include a fourth set of struts 436 extending between the third set of struts 434 and the body 410 of the implant 400, as shown in FIG. 32B. The fourth set of struts 436 may be, for example, angled as they extend between the third set of struts 434 and the body 410 and may form a "V" shape or an "X" shape. In addition to the strut embodiments shown, alternative strut arrangements are also contemplated in the opening 416 that provide the necessary support structure for the implant 400 and allow for bone through-growth, incorporation of biologic products, and/or allow for cross-communication of blood.

The implant 400 may also include a plurality of protrusions or spikes 438, as shown in FIGS. 31-36. The spikes 438 may be, for example, coupled to at least one of the struts 430, 432, 434. Although, nine spikes 438 are shown on each side of the implant 400 in the depicted embodiment, alternative numbers of spikes 438 are also contemplated to secure the implant 400 within the osteotomy opening in the bone, for example, at least two spikes are contemplated. The spikes 438 may, for example, extend beyond the proximal and distal surfaces of the implant 400 to engage the surrounding bone and prevent expulsion from the osteotomy site. The spikes 438 may extend, for example, approximately 0.25 mm to approximately 1 mm and, more specifically, approximately 0.5 mm above the proximal surface or distal surface of the implant 400. Although shown as circular protrusions 438, it is also contemplated that other shapes that could assist with securing the implant 400 within the osteotomy site may be used.

Figure 37:
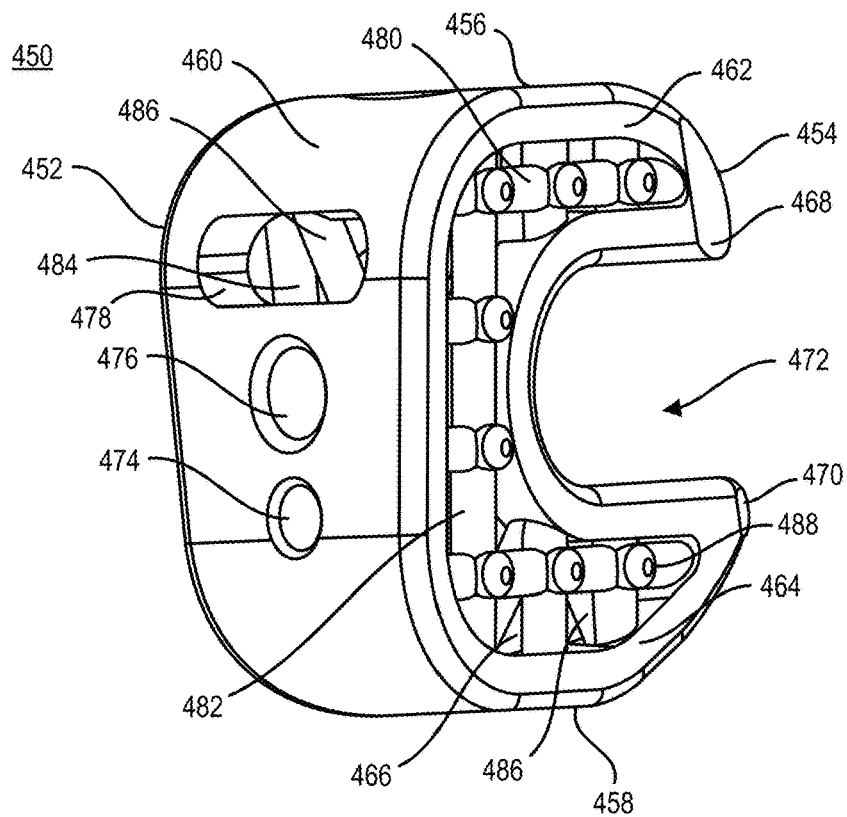
FIG. 37 is a perspective view of yet another embodiment of an implant, in accordance with an aspect of the present invention.
Figure 38:
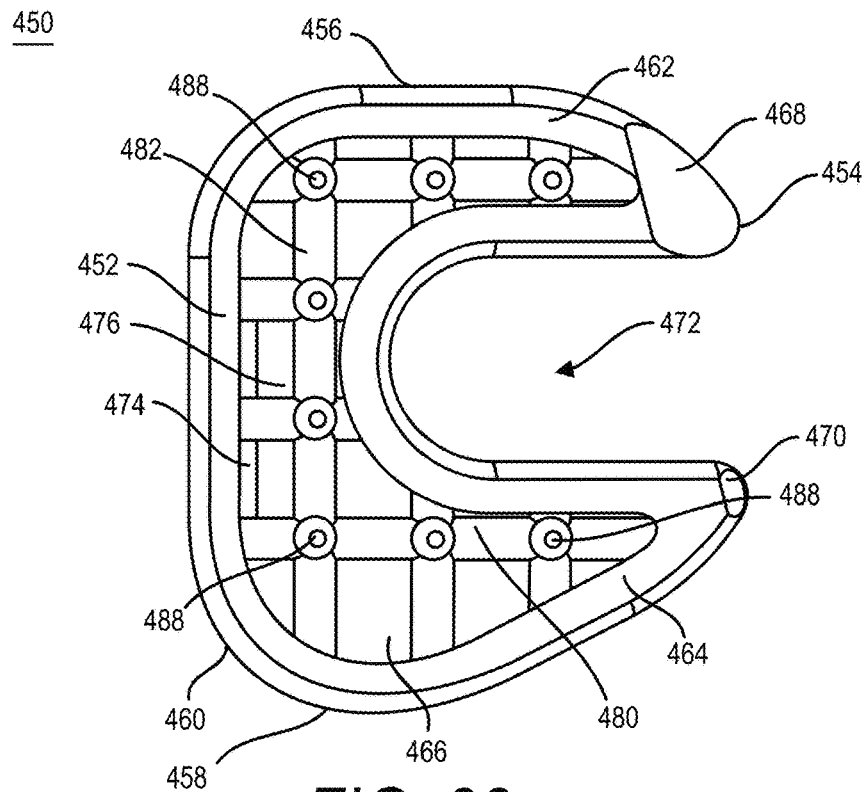
FIG. 38 is a front view of the implant of FIG. 37, in accordance with an aspect of the present invention.
Figure 39:
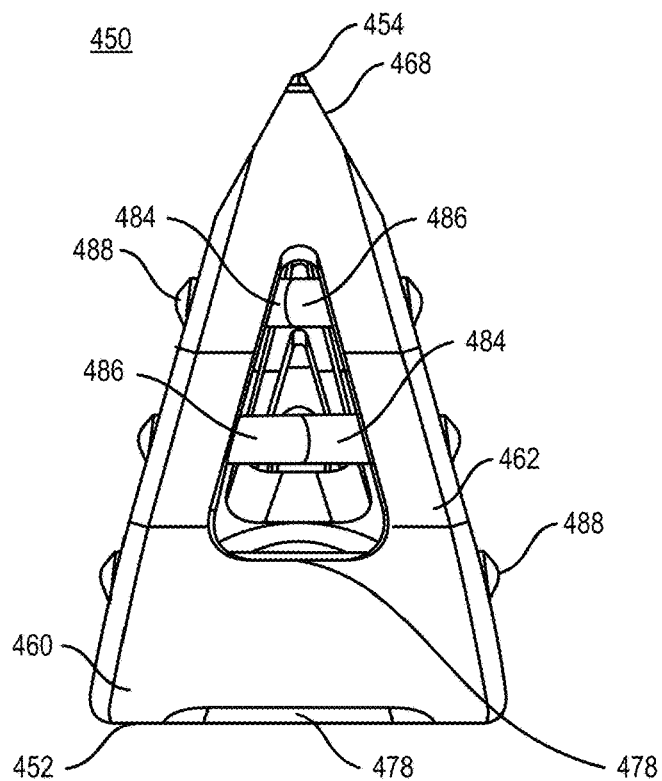
FIG. 39 is a top view of the implant of FIG. 37, in accordance with an aspect of the present invention.
Figure 40:
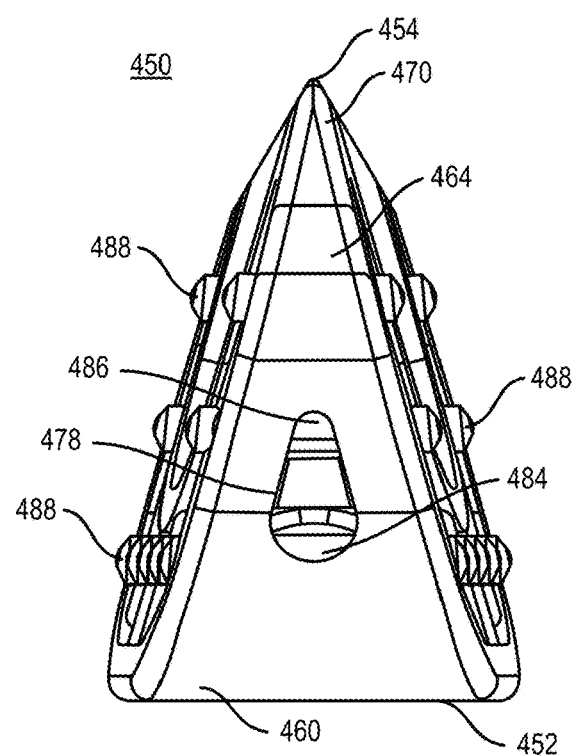
FIG. 40 is a bottom view of the implant of FIG. 37, in accordance with an aspect of the present invention.
Figure 41:
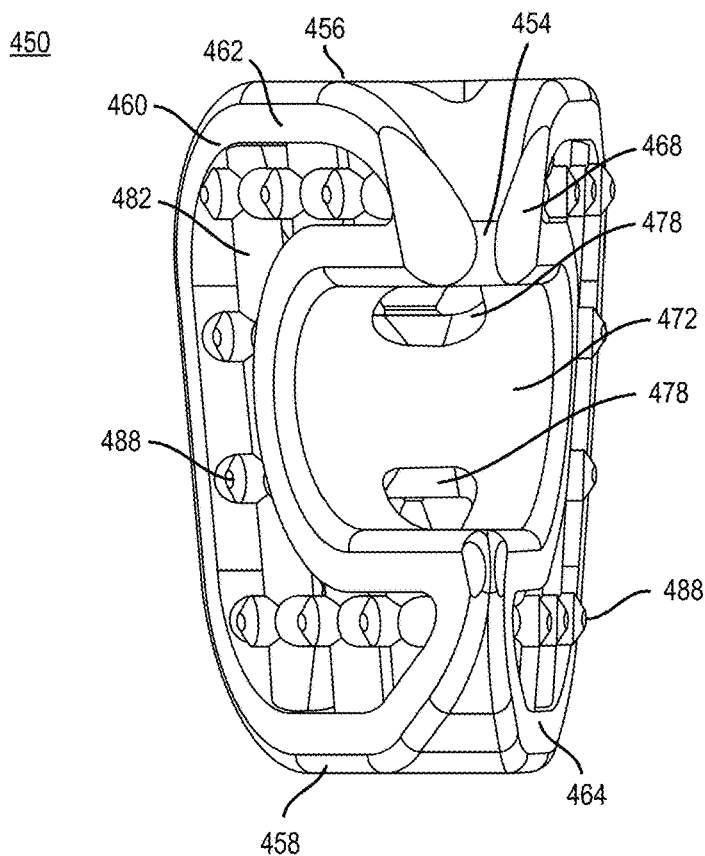
FIG. 41 is a first side view of the implant of FIG. 37, in accordance with an aspect of the present invention.

Referring now to FIGS. 37-42, the second implant 450 is shown. The second implant 450 may include a first end 452, a second end 454, a top side 456 and a bottom side 458. The second implant 450 may include a body or frame 460 with a first leg or projection 462, a second leg or projections 464, and an opening 466. The opening 466 extends through the body 460 from a proximal side to a distal side of the implant 450. The first leg 462 may be positioned on the top 456 and the second leg 464 may be positioned on the bottom 458. As shown in FIGS. 38 and 41, the second leg 464 may have a larger maximum height in the dorsal-plantar direction than the first leg 462 where the legs 462, 464 couple to the body 460. In the depicted embodiment, the first leg 462 and the second leg 464 may have, for example, curved exterior surfaces as the legs 462, 464 extend from the first end 452 to the second end 454. The ends or tips 468, 470 of the legs 462, 464, respectively, may be, for example, tapered or otherwise shaped to aide in the insertion into a patient's bone. The legs 462, 464 may be spaced apart to define a channel 472 between the legs 462, 464. As discussed in greater detail below, the channel 472 may be sized and shaped or configured to allow for a fastener, for example, a bone screw to pass through the channel 472 and across the osteotomy site.

Figure 51:
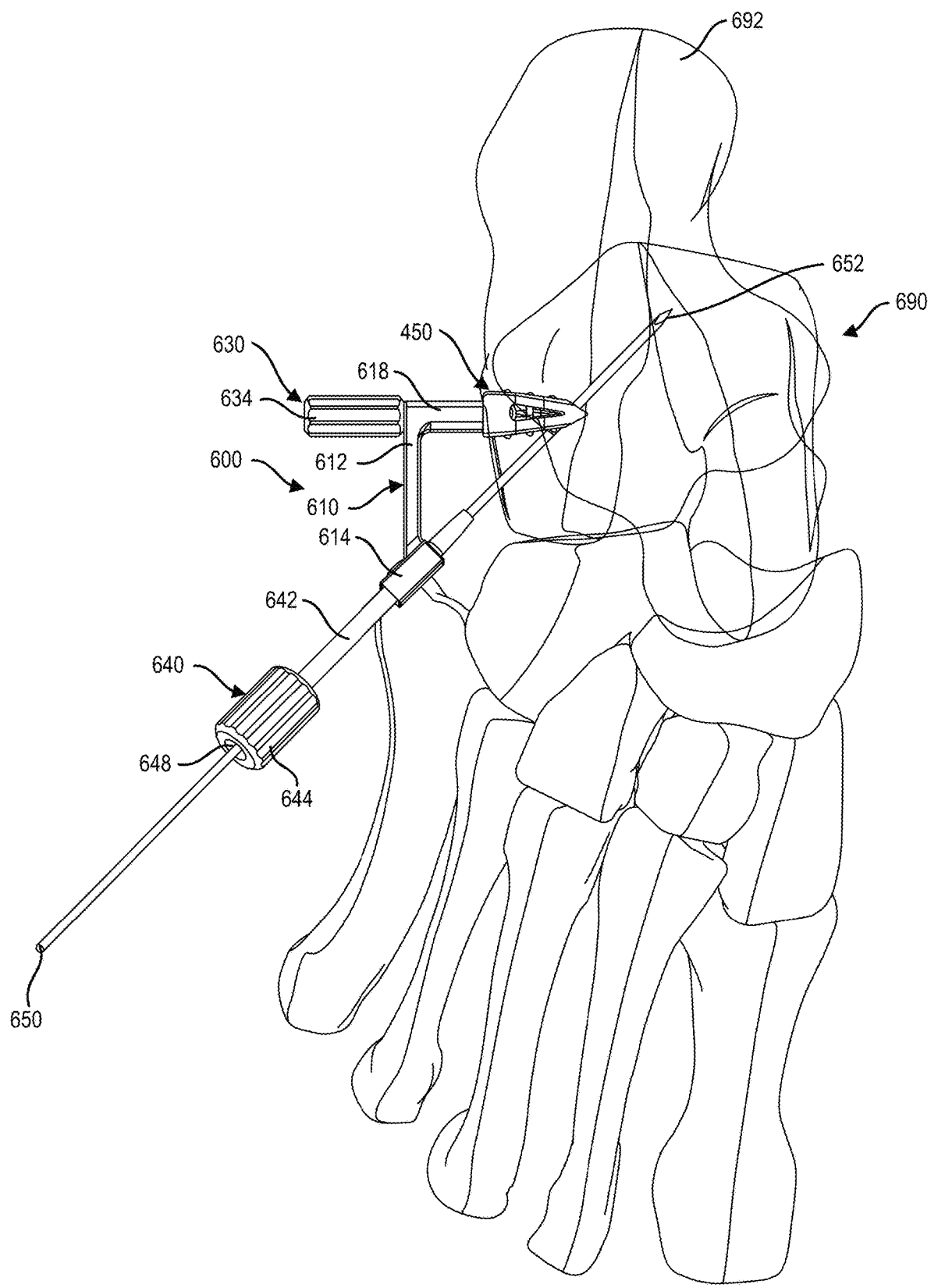
FIG. 51 is a top view of the fastener guide and implant of FIG. 47 positioned with respect to a portion of a foot, in accordance with an aspect of the present invention.
Figure 52:
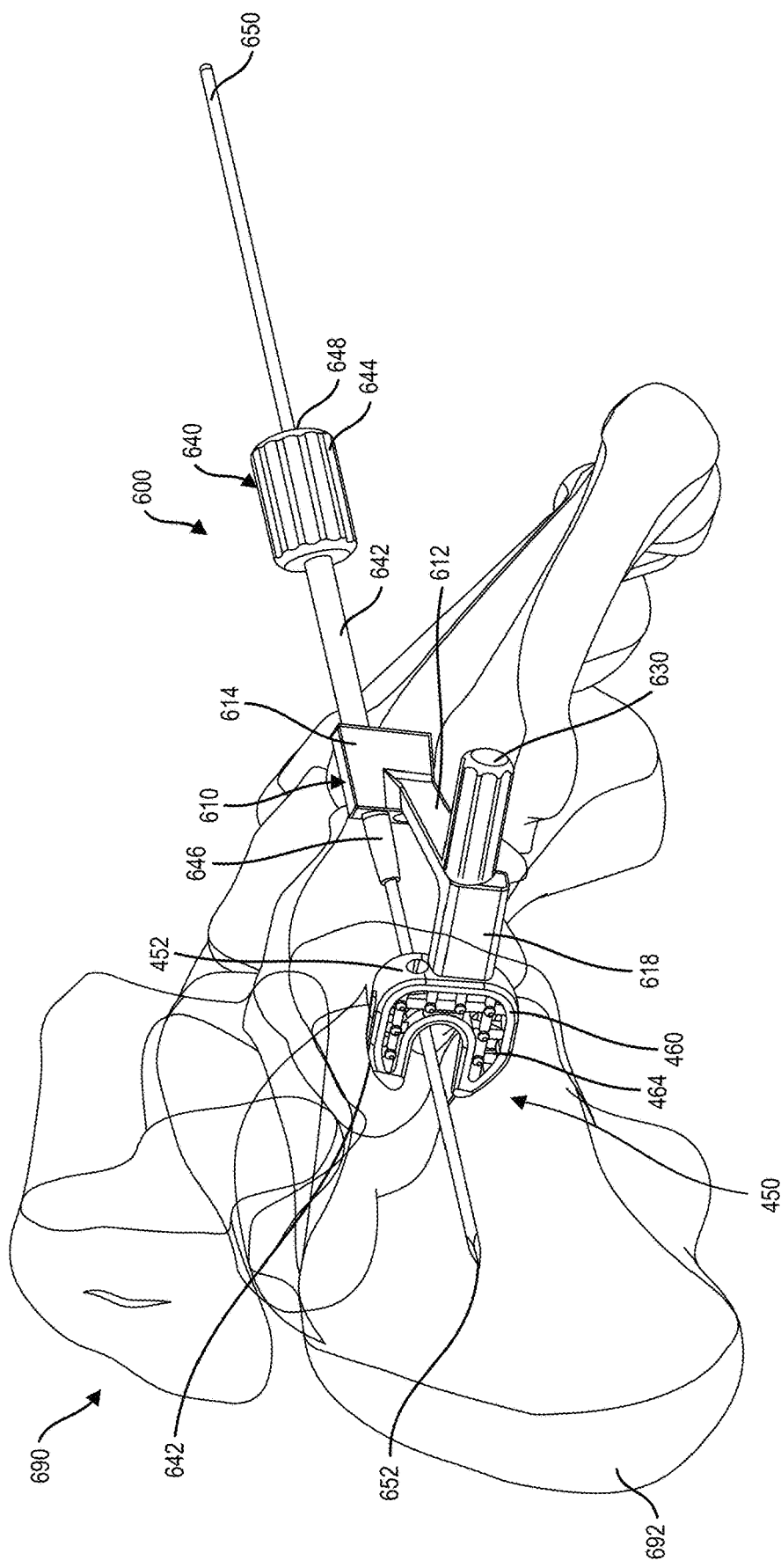
FIG. 52 is a side perspective view of the fastener guide and the implant of FIG. 51, in accordance with an aspect of the present invention.
Figure 53:
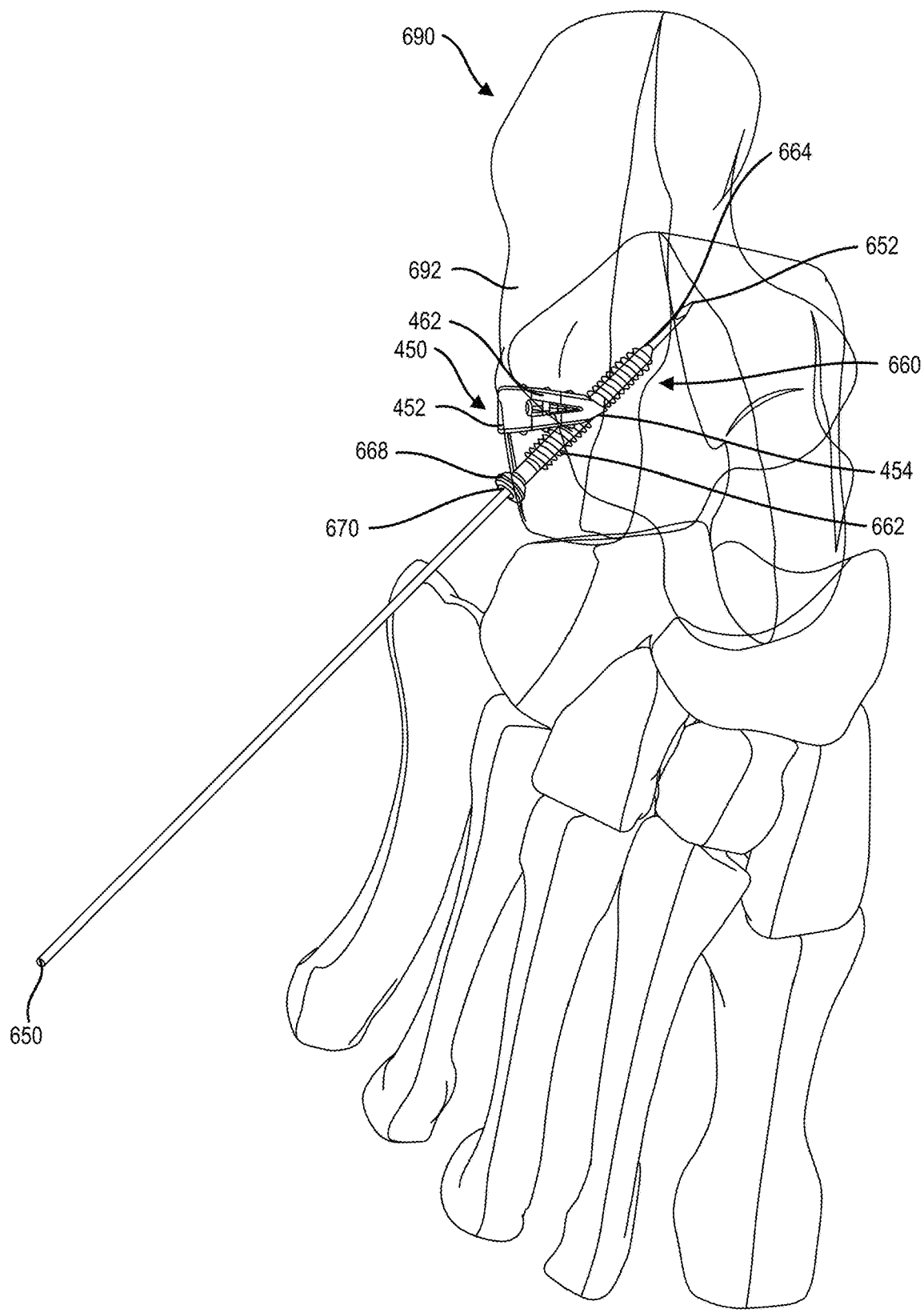
FIG. 53 is a top view of the foot, implant and the k-wire of the fastener guide system of FIG. 52 and a fastener, in accordance with an aspect of the present invention.

The first end 452 of the body 460 may be, for example, planar with curved or angled edges positioned between the first end 452 and each of the legs 462, 464, as shown in FIGS. 37 and 38. The exterior surface of the planar with curved or angled edges first end 452 of the body 460 may have a shape corresponding to a patient's calcaneus bone 692, as shown in FIGS. 51-53. The surface of the first end 452 may be, for example, smooth. The first end 452 of the body 460 may also have a width extending from the proximal surface to the distal surface. The implant 450 may have body widths of, for example, approximately 6 mm to approximately 12 mm. The width of the implant 450 may be selected based on the desired correction. The body 460 may also have a dorsal to plantar taper, for example, a taper from the top 456 to the bottom 458 of the implant 450 (See FIG. 40). The dorsal to plantar taper may allow for a reduction in plantar ligament stress. In addition, the body 460 may have a medial to lateral taper, for example, a taper from the first end 452 to the second end 454 (See FIG. 39). The medial to lateral taper may allow for lateral column lengthening. The dorsal to plantar taper and the medial to lateral taper form an implant 450 with bi-planar bone contacting surfaces. Each leg 462, 464 may have an end 468, 470, respectively. The ends 468, 470 of the implant 450 may be, for example, further tapered to form a sharp angle or point at each end 468, 470.

Figure 42:
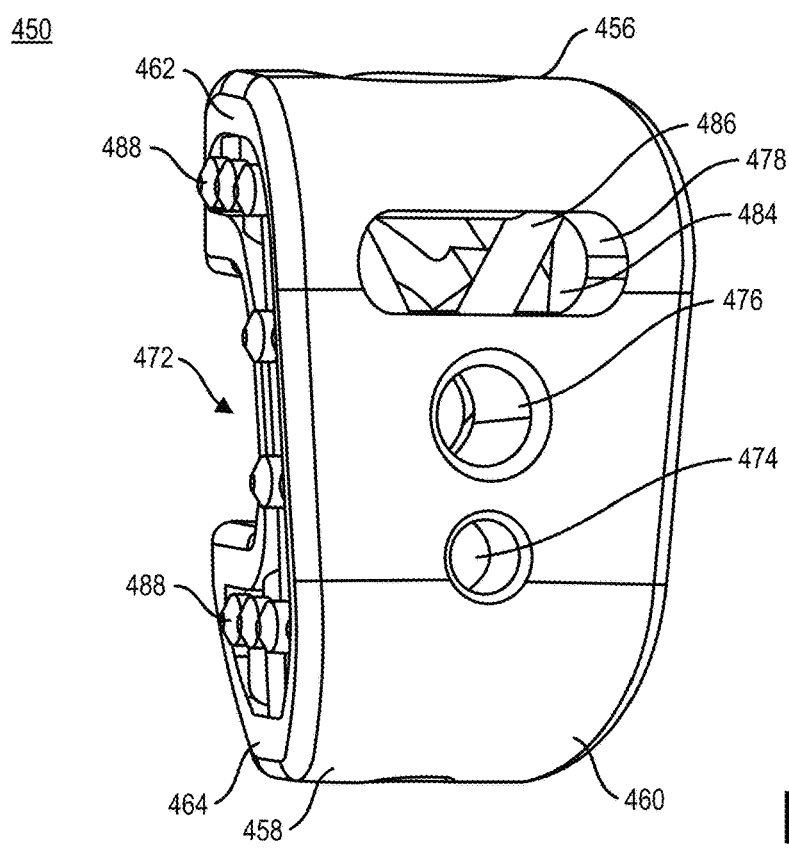
FIG. 42 is a second side view of the implant of FIG. 37, in accordance with an aspect of the present invention.

As shown in FIGS. 37 and 42, the first end 452 of the body 460 may also include an alignment opening 474 and a securement opening 476. The alignment opening 474 may be positioned adjacent to the securement opening 476 on the first end 452 of the implant 450. The alignment opening 474 may be, for example, configured or sized and shaped to receive an alignment pin from the insertion instrument 500, a guide system 600 and/or a resection guide system 700, as described in greater detail below. The alignment opening 474 may, for example, extend into a portion of the opening 466 in the body 460 at the first end 452 of the implant 450. The securement opening 476 may, for example, extend into the first end 452 of the body 460, through the opening 466, and into at least a portion of the body 460 at the bottom of the channel 472. The securement opening 476 may extend into the implant 450 father than the alignment opening 474. The securement opening 476 may be, for example, threaded to receive a fastener to couple the implant 450 to an insertion instrument 500, a guide system 600 and/or a resection guide system 700, as described in greater detail below. The threads in the securement opening 476 may be, for example, sized to engage the threads on a fastener. The body 460 may also include at least one window or opening 478 on the first end 452, as shown in FIGS. 37 and 42, the top surface 456, as shown in FIG. 39, the bottom surface 458, as shown in FIG. 40, and the surface at the bottom of channel 472, as shown in FIG. 41. The windows 478 may extend from an exterior surface of the implant 450, through the body wall 460, and into the opening 466, as shown in FIGS. 37, 41 and 42. The windows 478 may be, for example, configured or sized and shaped to allow for bone growth and cross-communication of blood within the osteotomy site.

As shown in FIGS. 37 and 38, the opening 466 may include, a plurality of struts or linear members, 480, 482, 484, 486 extending across the opening 466 and coupled to the body 460. The plurality of struts 480, 482, 484, 486 may include, for example, a first set of struts 480, a second set of struts 482, a third set of struts 484, and a fourth set of struts 486. The first set of struts 480 may extend, for example, in a medial-lateral direction, as shown in FIGS. 37 and 38. The second set of struts 482 may extend, for example, in a dorsal-plantar direction, as also shown in FIGS. 37 and 38. The third set of struts 484 may extend, for example, in a proximal-distal direction, as shown in FIGS. 39 and 40. The third set of struts 484 may be positioned perpendicular to the first set of struts 480 and the second set of struts 482 to form a three dimensional matrix within the opening 466. The opening 466 may also include a fourth set of struts 486 extending between the third set of struts 484 and the body 460 of the implant 450. The fourth set of struts 486 may be, for example, angled as they extend between the third set of struts 484 and the body 460 and may form a "V" shape or an "X" shape. In addition to the strut embodiments shown, alternative strut arrangements are also contemplated in the opening 466 that provide the necessary support structure for the implant 450 and allow for bone through-growth, incorporation of biologic products, and/or allow for cross-communication of blood.

The implant 400 may also include a plurality of protrusions or spikes 488, as shown in FIGS. 37-42. The spikes 488 may be, for example, coupled to at least one of the struts 480, 482, 484. Although, eight spikes 488 are shown on each side of the implant 450 in the depicted embodiment, alternative numbers of spikes 488 are also contemplated to secure the implant 450 within the osteotomy opening in the bone, for example, at least two spikes is contemplated. The spikes 488 may, for example, extend beyond the proximal and distal surfaces of the implant 450 to engage the surrounding bone and prevent expulsion from the osteotomy site. The spikes 488 may extend, for example, approximately 0.25 mm to approximately 1 mm and, more specifically, approximately 0.5 mm above the proximal surface or distal surface of the implant 450. Although shown as circular protrusions 488, it is also contemplated that other shapes that could assist with securing the implant 450 within the osteotomy site may be used.

Figure 45:
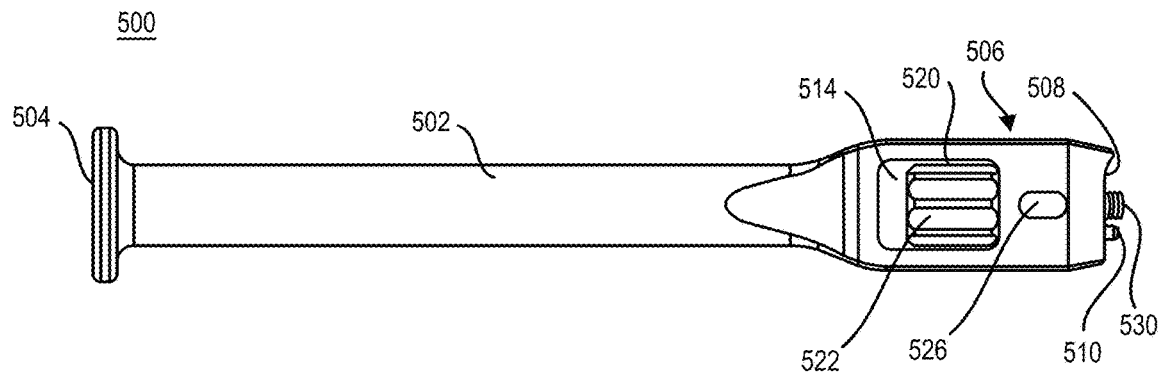
FIG. 45 is a side view of the insertion instrument of FIG. 43, in accordance with an aspect of the present invention.
Figure 46:
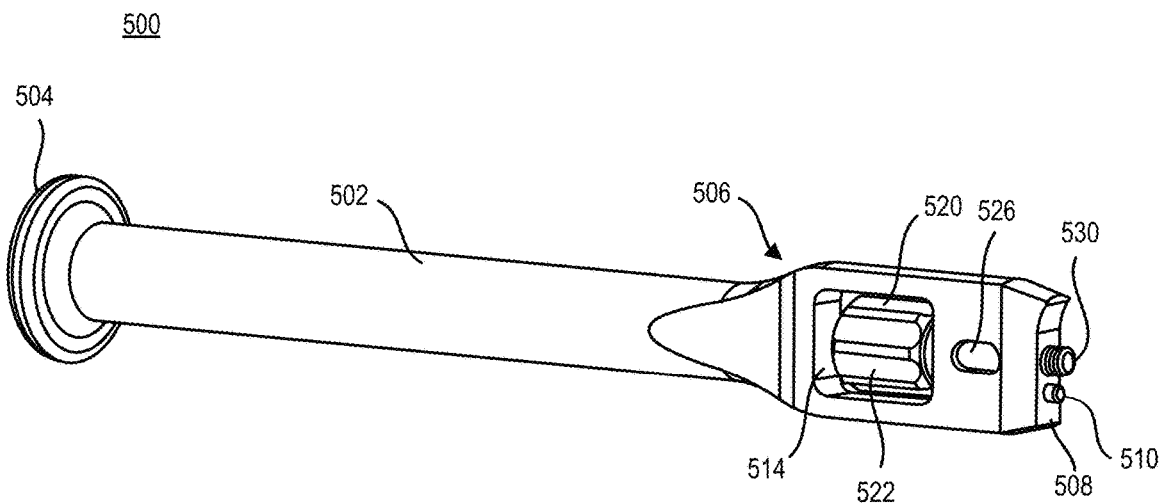
FIG. 46 is a perspective view of the insertion instrument of FIG. 43, in accordance with an aspect of the present invention.

Referring now to FIGS. 43-46, an inserter instrument 500 is shown. Although the inserter instrument 500 is shown only with respect to implant 450, the inserter instrument 500 may also be used with implant 400 as described in greater detail below. The inserter instrument 500 includes a body 502 with a strike plate or impact portion 504 at a first end and a nose portion 506 at a second end. The strike plate 504 provides a surface wider than the body 502 for hitting to force an implant 400, 450 into the correct position between two bone portions. The nose portion 506 includes a contact surface 508 for mating with the implant 400, 450. The contact surface 508 may be, for example, configured or sized and shaped to correspond to the size and shape of the first end 402, 452 of the body 410, 460 of the implant 400, 450, respectively. As shown in FIGS. 44-46, the contact surface 508 may be, for example, curved, arced, or angled such that the top surface of the nose portion 506 extends out past the end of the bottom surface of the nose portion 506. The body 502 may have a width that is larger than the second end and the nose portion 506. To provide the variation in width, the second end of the inserter instrument 500 may be, for example, tapered from the body 502 to the nose portion 506.

Referring now to FIG. 44, the nose portion 506 may also include an alignment pin 510, a securement opening 512 and a window 514. The securement opening 512 may extend in a first direction, for example, from the window 514 through the nose portion 506 and out through the contact surface 508. The window 514 may extending through the nose portion 506 in a second direction. The second direction may be relatively perpendicular to the first direction. The alignment pin 510 may be, for example, coupled to and extending out from the contact surface 508 of the nose portion 506. The alignment pin 510 may be positioned below the securement opening 512.

The inserter instrument 500 also includes a securement member 520, as shown in FIGS. 44-46. The securement member 520 includes a knob 522 and a shaft 526. The shaft 526 may be coupled to the knob 522 at a first end and include an engagement portion 530 at a second end, as shown in FIG. 44. The securement member 520 is positioned within the body 502, specifically, the shaft 526 passes through the securement opening 512, the engagement portion 530 and extends out beyond the contact surface 508, and the knob 522 may be positioned within the window 514. The engagement portion 530 may be coupled to corresponding threads in the securement opening 426, 476, shown in FIGS. 31, 36, 37, and 42, of the implant 400, 450.

As shown in FIG. 43, the implant 450 may be coupled to the inserter instrument 500 for insertion into a patient. The implant 450 may be coupled by aligning the alignment pin 510 of the inserter instrument 500 with the alignment opening 424, 474, as shown in FIGS. 31, 36, 37, and 42, of the implant 400, 450. Then, the knob 522 of the securement member 520 may be rotated to thread the engagement portion 530 of the securement member 520 into the securement opening 426, 476, as shown in FIGS. 31, 36, 37, and 42, of the implant 400, 450. As the knob 522 is rotated, the engagement portion 530 moves the implant 400, 450 to come in contact with the surface 508. Once the implant 400, 450 is secured to the inserter instrument 500, the implant 400, 450 may be inserted into the patient.

A fastener guide system 600 is depicted in FIGS. 47-53. Once the implant 400, 450 is inserted into a patient's bone, the fastener guide system 600 may be used to insert a fastener 660 across the osteotomy site to strengthen the bone construct. The fastener guide system 600 includes an alignment arm 610, a fixation member 630, an insertion guide 640, a temporary fixator 650, and a fastener 660. The alignment arm 610 may include a body 612 with a first arm 614 at a first end and a second arm 618 at a second end. The first arm 614 may be coupled to the first end of the body 612 at an angle with respect to the body 612. The angle may be selected, for example, to allow for insertion of the fastener 660 between the two legs 412, 462, 414, 464 of the implant 400, 450, respectively, and to prevent the fastener 660 from contacting the implant 400, 450 during insertion. The second arm 618 may be coupled relatively perpendicular to the second end of the body 612. In an alternative embodiment, the body 612 may include an opening (not shown) through the body 612 in place of the first arm 614. The opening (not shown) may be, for example, angled to the trajectory desired for inserting the fastener 660 between the two legs 462, 464.

Figure 48:
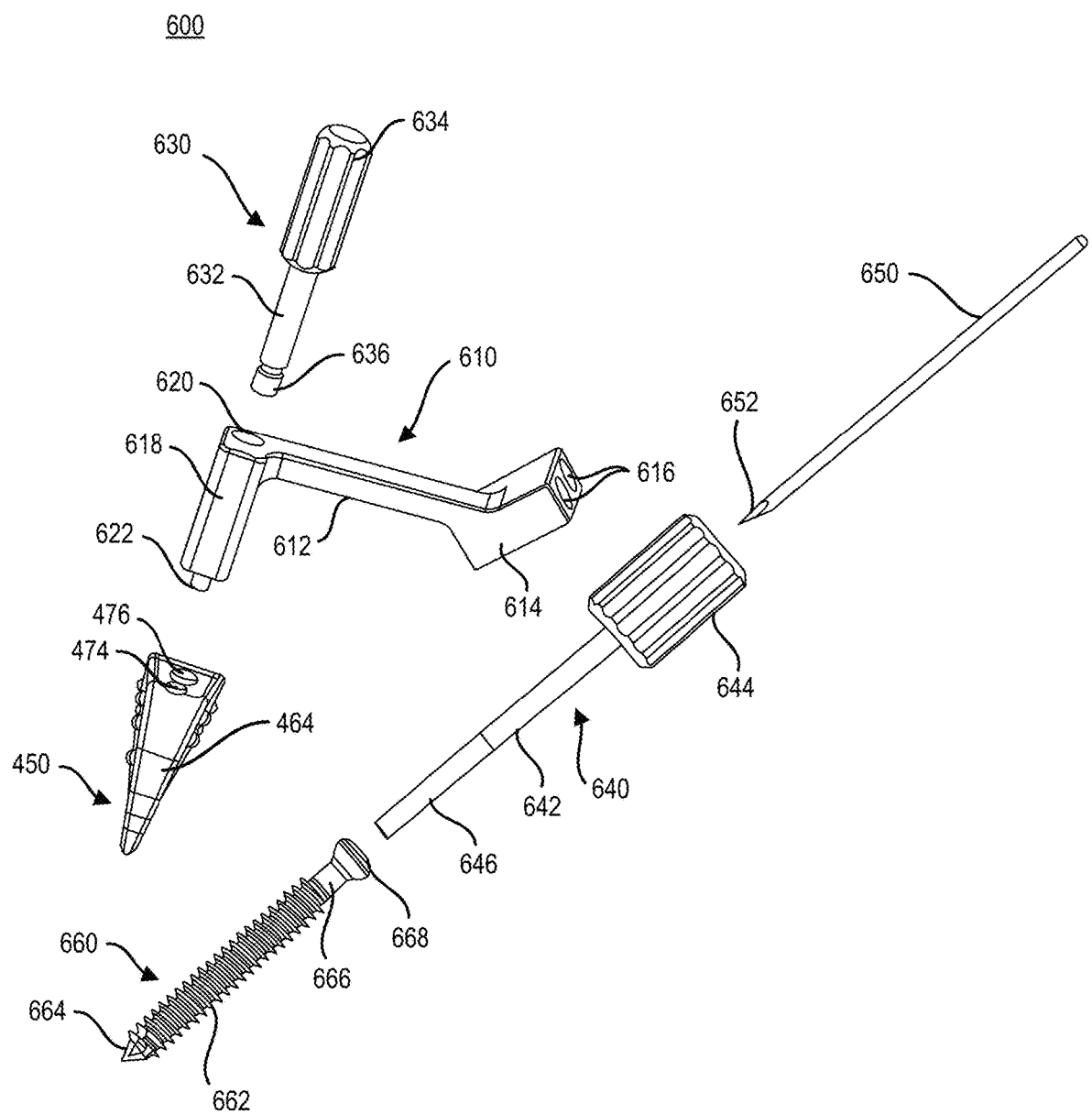
FIG. 48 is an exploded side view of the fastener guide, fastener, and implant of FIG. 47, in accordance with an aspect of the present invention.
Figure 49:
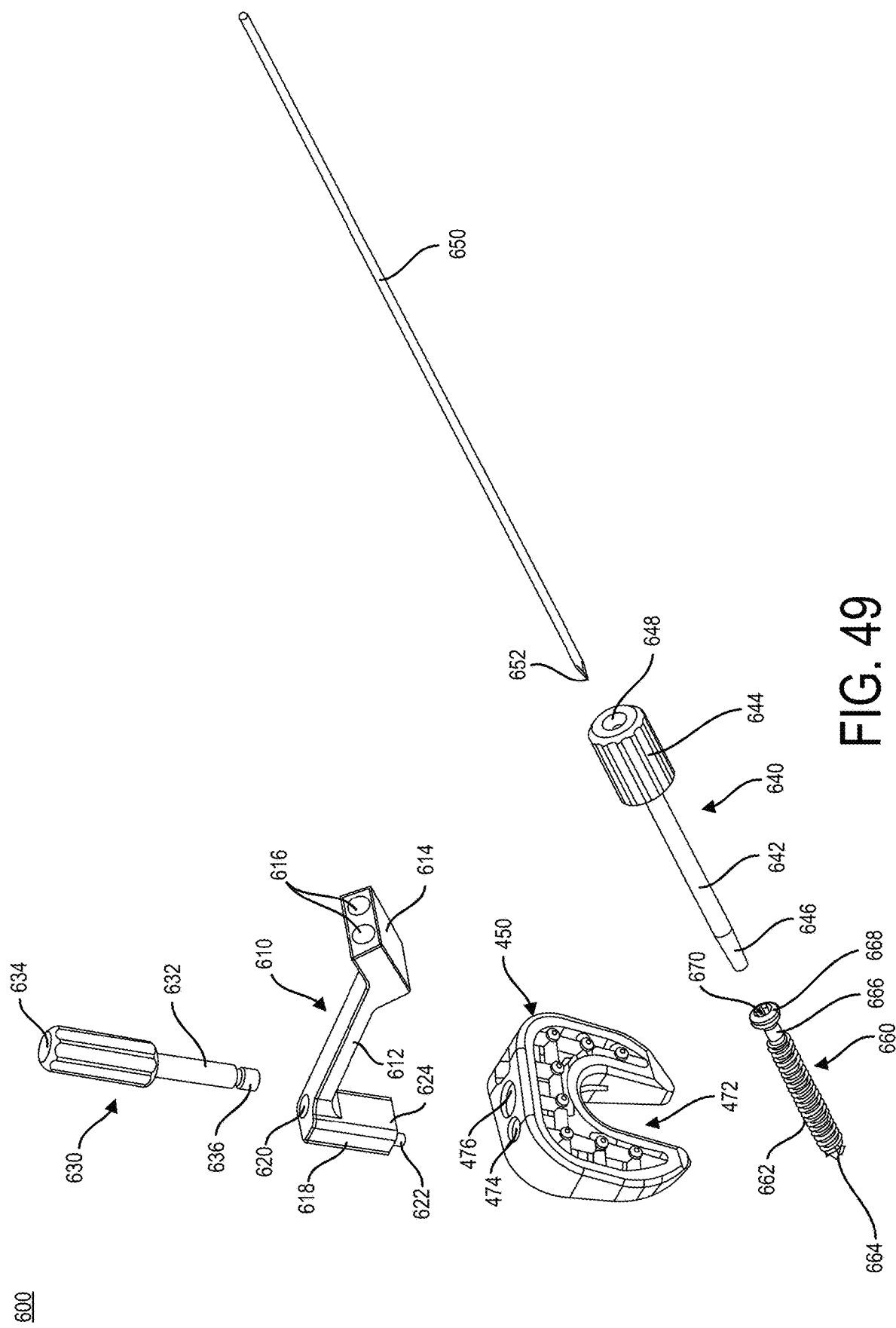
FIG. 49 is an exploded top perspective view of the fastener guide, fastener, and implant of FIG. 47, in accordance with an aspect of the present invention.
Figure 50:
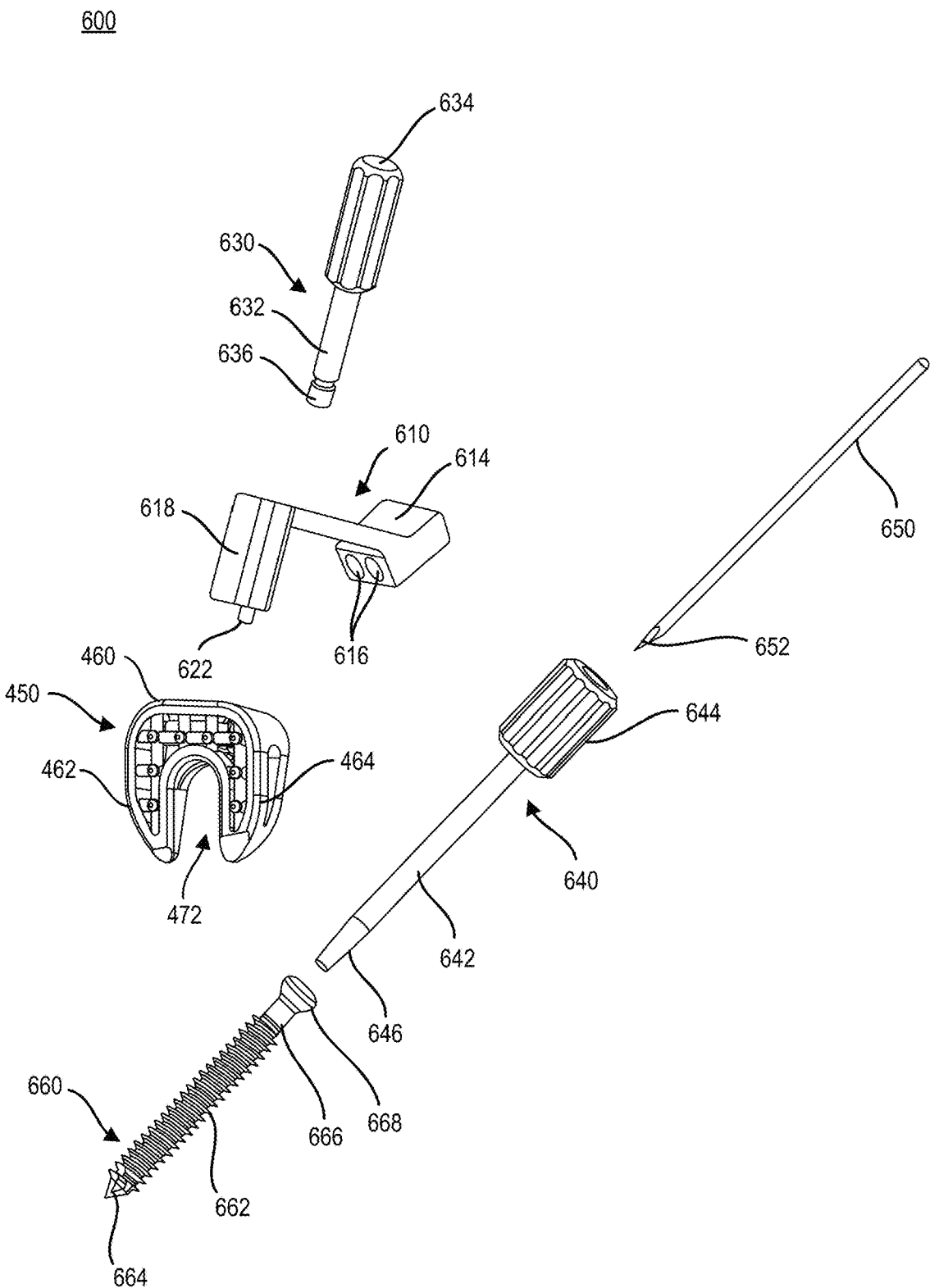
FIG. 50 is an exploded bottom perspective view of the fastener guide, fastener, and implant of FIG. 47, in accordance with an aspect of the present invention.

The first arm 614 may include at least one temporary fixator guide opening or k-wire guide opening 616 for receiving the insertion guide 640, as shown in FIGS. 48-50. Although not shown, the first arm 614 may include multiple openings 616 positioned at varying angles to provide different trajectory options for the fastener 660. In another embodiment, the first arm 614 may include one opening 616 positioned at a specific angle. It is also contemplated that the fastener guide system 600 may include multiple alignment arms 610 and each alignment arm 610 may include a first arm 614 with the opening 616 positioned at a different angle with respect to body 612 to provide different trajectories for inserting the fastener 660. The insertion guide or k-wire guide 640 may include a base member 642 with a handle portion 644 at a first end and an insertion portion 646 at a second end. The guide 640 may also include an opening 648 extending from the first end to the second end. The opening 648 may be sized and shaped to receive a temporary fixator 650, for example, a k-wire or guide wire. The k-wire 650 may have, for example, a pointed or sharp end 652 to assist with insertion into and/or through a patient's bone or bones.

The second arm 618 may include an opening 620, an alignment pin 622 positioned adjacent to the opening 620, and an engagement surface 624, as shown in FIGS. 48-50. The opening 620 may extend from a top surface of the second arm 618 through to the engagement surface 624 or bottom surface of the second arm 618. The alignment pin 622 is coupled to and extends from the engagement surface 624 of the second arm 618. The alignment pin 622 may be sized and shaped or configured to fit into the alignment opening 424, 474 of the implant 400, 450. The engagement surface 424, 474 may be, for example, configured or sized and shaped to correspond to the size and shape of the first end 402, 452 of the body 410, 460 of the implant 400, 450. As shown in FIG. 49, the engagement surface 624 may be, for example, generally planar.

Figure 47:
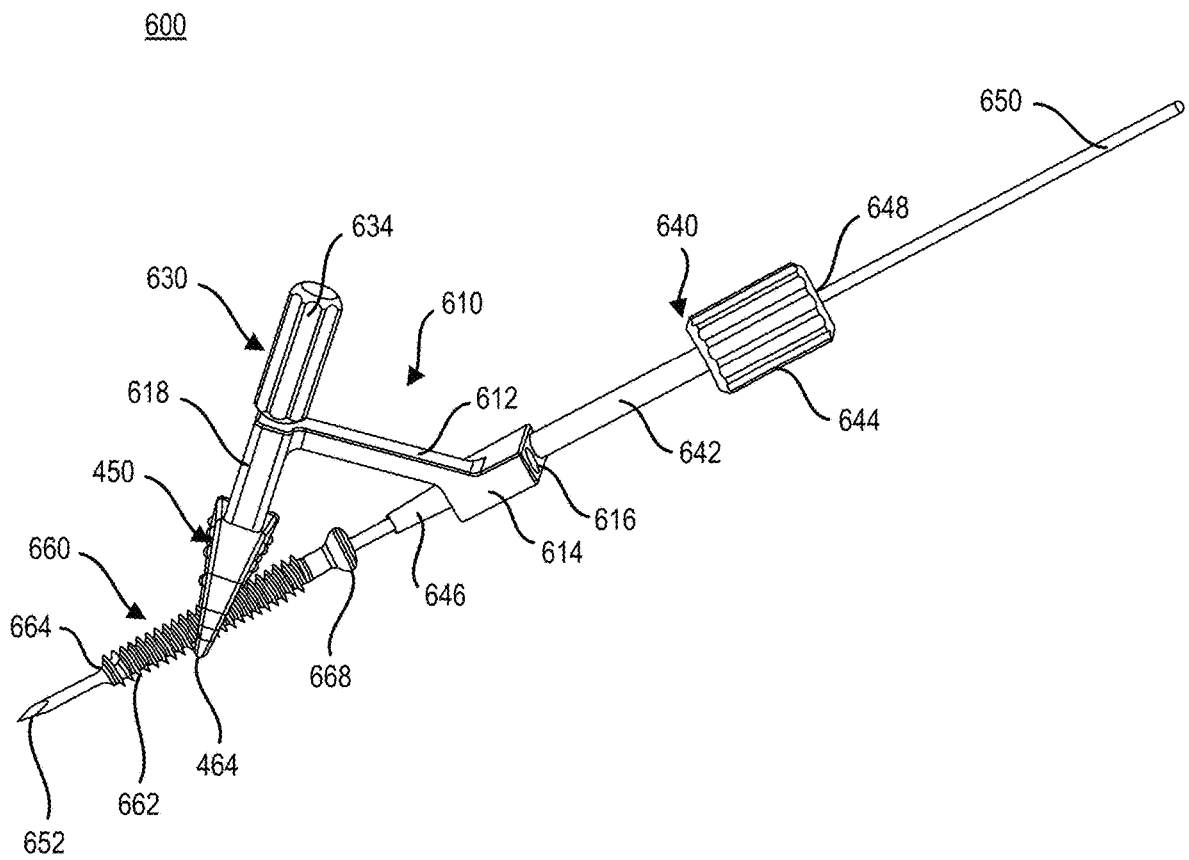
FIG. 47 is a side perspective view of another embodiment of a fastener guide, a fastener, and the implant of FIG. 37, in accordance with an aspect of the present invention.

The opening 620 of the second arm 618 is configured or sized and shaped to receive the fixation member 630, as shown in FIG. 47. The fixation member 630 includes a shaft 632 with a handle 634 at a first end and a threaded member 636 at a second end. The shaft 632 may be positioned within the opening 620 with the threaded member 636 extending out the bottom of the opening 620 to couple to the implant 400, 450. The threaded member 636 includes threads (not shown) to couple to corresponding threads in the securement opening 426, 476, as shown in FIGS. 31, 36, 37, and 42, of the implant 400, 450 during insertion of the k-wire 650 across the osteotomy site.

Referring now to FIGS. 51-53, an embodiment of the fastener guide system 600 is shown with respect to a portion of a patient's foot 690. FIGS. 51-53 show only one implant, implant 450 for brevity purposes, but the below description includes reference to use of both implants 400, 450 with the fastener guide system 600. The implant 400, 450 has been inserted within the osteotomy site in the patient's calcaneus 692, as shown in FIGS. 51-53. The alignment arm 610 of the fastener guide system 600 is coupled to the implant 400, 450 by the fixation member 630. The insertion guide 640 is inserted through one of the openings 616 in the first arm 614 of the alignment arm 610 and contacts the patient's foot 690. Next, the temporary fixator 650 is inserted through the opening 648 in the insertion guide 640 and into the bone 692, as shown in FIGS. 51-53. The temporary fixator 650 passes through the osteotomy site and between the legs 412, 462, 414, 464 of the implant 400, 450. After the k-wire 650 is positioned in the desired orientation in the patient's foot 690, the fixation member 630 may be removed from the implant 400, 450 and the alignment arm 610. Then the insertion guide 640 and alignment arm 610 may be removed and a fastener 660, such as, a cannulated screw or cannulated bone screw, may be inserted over the k-wire 650 and into the patient's foot 690, as shown in FIG. 53. The fastener 660 will be inserted through the channel 422, 472 of the implant 400, 450 between the legs 412, 462, 414, 464 and across the osteotomy site in the calcaneus 692.

Figure 61:
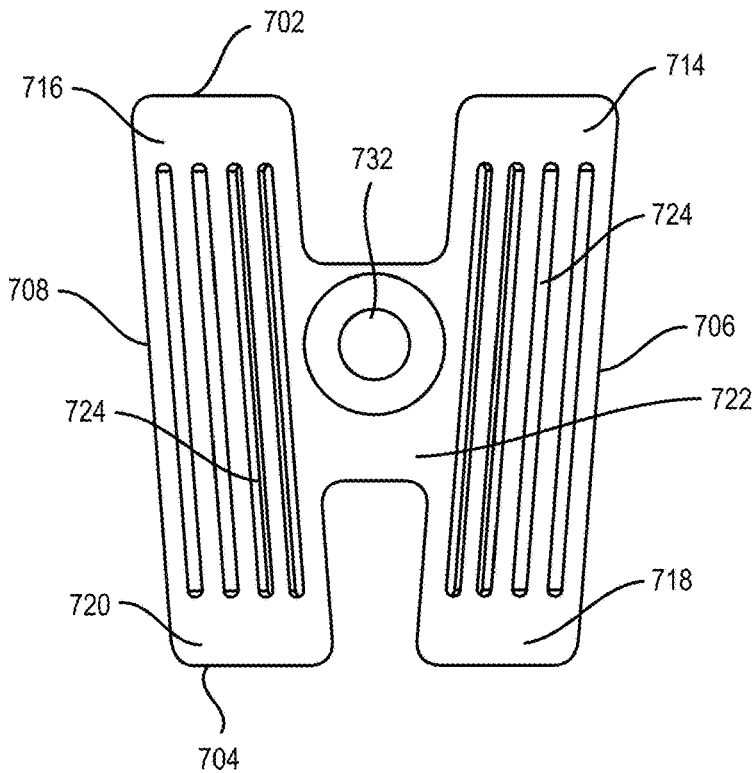
FIG. 61 is a top view of the resection guide of FIG. 54, in accordance with an aspect of the present invention.
Figure 62:
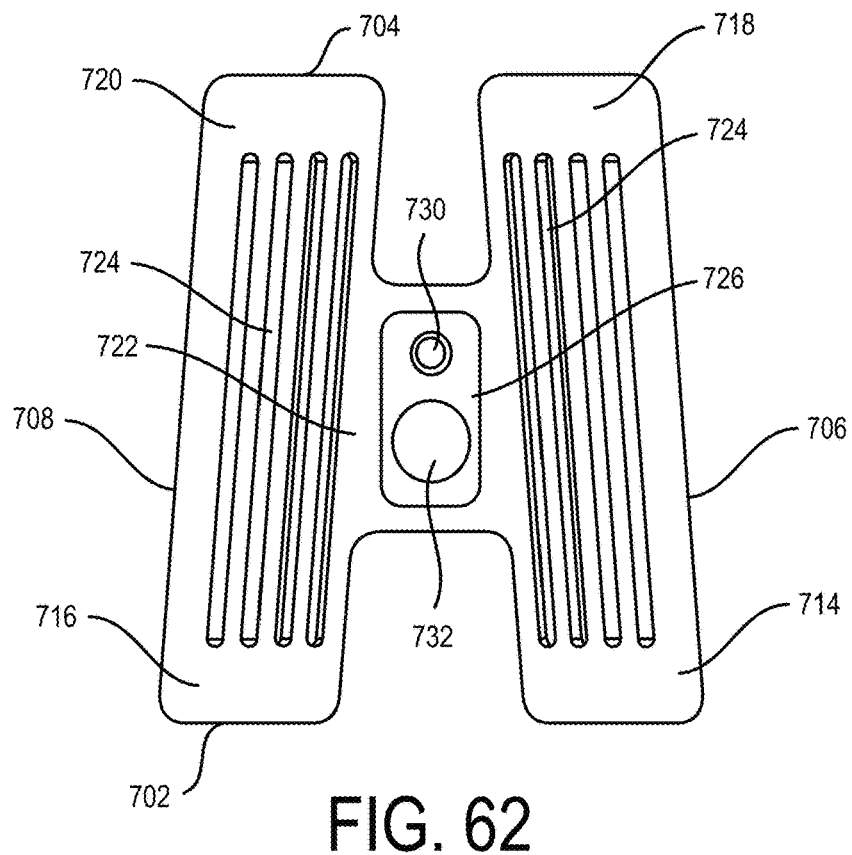
FIG. 62 is a bottom view of the resection guide of FIG. 54, in accordance with an aspect of the present invention.
Figure 63:
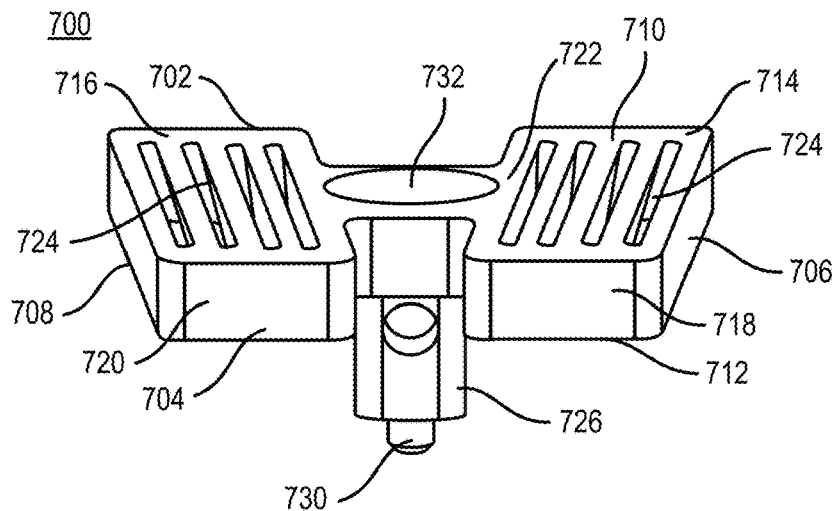
FIG. 63 is a first end perspective view of the resection guide of FIG. 54, in accordance with an aspect of the present invention.
Figure 64:
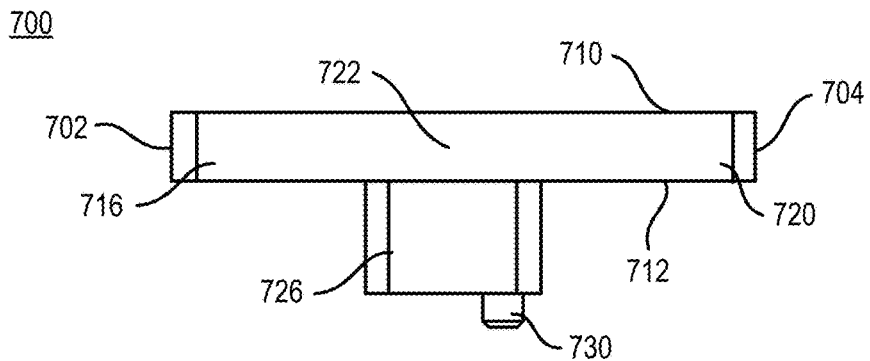
FIG. 64 is a side view of the resection guide of FIG. 54, in accordance with an aspect of the present invention.
Figure 65:
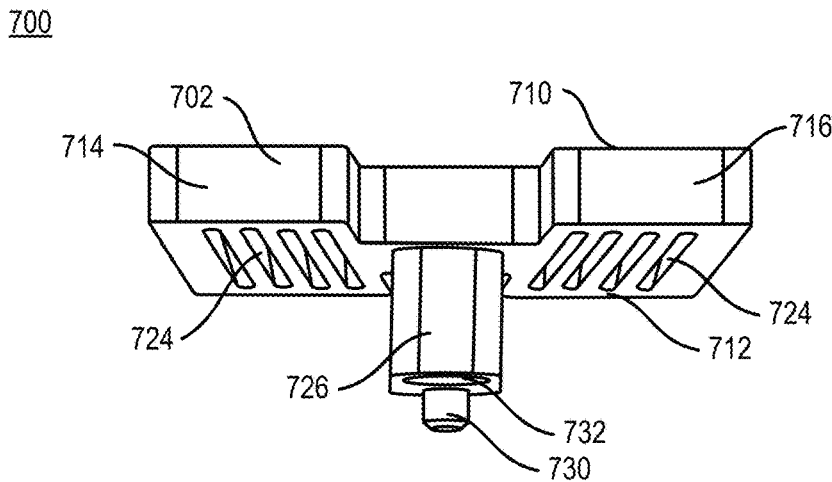
FIG. 65 is a second end perspective view of the resection guide of FIG. 54, in accordance with an aspect of the present invention.

Referring now to FIGS. 54-65, a resection guide 700 is shown. The resection guide 700 may have a first end 702 opposite a second end 704, a first side 706 opposite a second side 708, and a top surface 710 opposite a bottom surface 712. The resection guide 700 may also have a first arm 714, a second arm 716, a first leg 718 and a second leg 720. The arms 714, 716 may extend out from the first end 702 of the resection guide 700. The first arm 714 is positioned on the first side 706 of the resection guide 700 and the second arm 716 is positioned on the second side 708 of the resection guide 700. The first and second arms 714, 716 are spaced apart to form a passage between the arms 714, 716. As shown in FIGS. 61-62, the arms 714, 716 are positioned angled with respect to each other and diverge away from a center or the longitudinal axis of the resection guide 700.

As shown in FIGS. 54-65, the legs 718, 720 may extend out from the second end 704 of the resection guide 700. The first leg 718 is positioned on the first side 706 of the resection guide 700 and the second leg 720 is positioned on the second side 708 of the resection guide 700. The first and second legs 718, 720 are spaced apart to form a passage between the legs 718, 720. As shown in FIGS. 61 and 62, the legs 718, 720 are positioned angled with respect to each other and converge towards a center or the longitudinal axis of the resection guide 700.

The resection guide 700 may also include at least two slots 724, as shown in FIGS. 54, 57-63 and 65. The slots 724 may be sized and shaped to receive a saw blade (not shown) to cut the patient's bone 792 and remove the implant 400, 450. At least one first slot 724 may extend along the first side 706 and through at least a portion of the first arm 714, the central portion 722, and at least a portion of the first leg 718. In the depicted embodiment, the at least one first slot 724 is four slots 724. At least one second slot 724 may extend along the second side 708 and through at least a portion of the second arm 716, the central portion 722 and at least a portion of the second leg 720. In the depicted embodiment, the at least one second slot 724 is four slots 724. The slots 724 may be angled as they extend from the top surface 710 to the bottom surface 712 of the resection guide 700. The slots 724 may be angled toward the center or a longitudinal axis of the resection guide 700. The angle of the slots 724 may correspond to the angle of the proximal side and distal side of the implant 400, 450.

Figure 54:
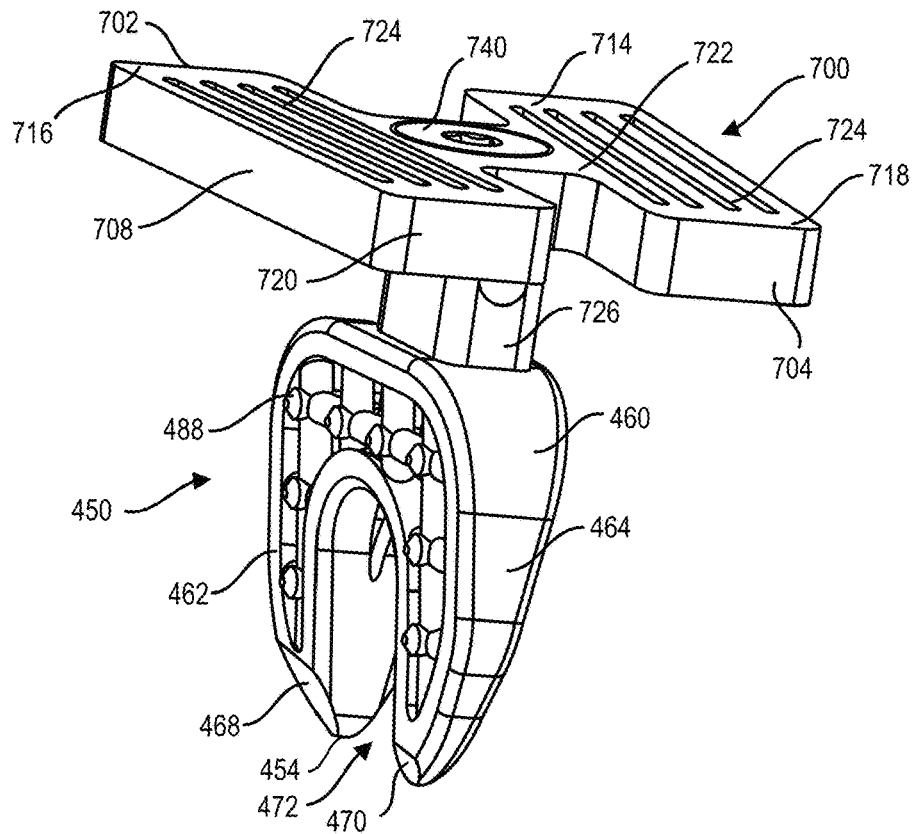
FIG. 54 is a perspective view of another embodiment of a resection guide and the implant of FIG. 37, in accordance with an aspect of the present invention.
Figure 55:
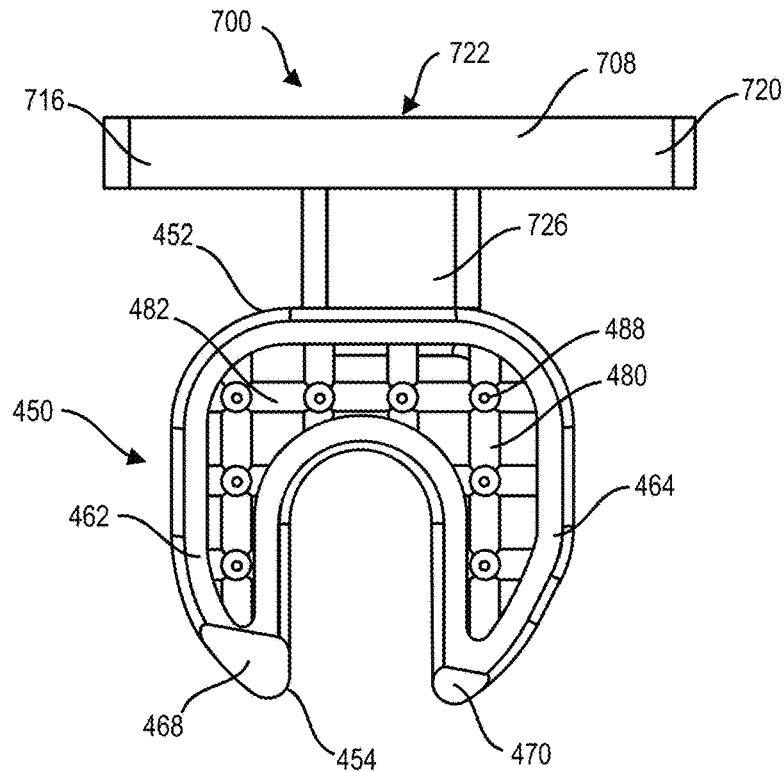
FIG. 55 is a front view of the resection guide and implant of FIG. 54, in accordance with an aspect of the present invention.
Figure 56:
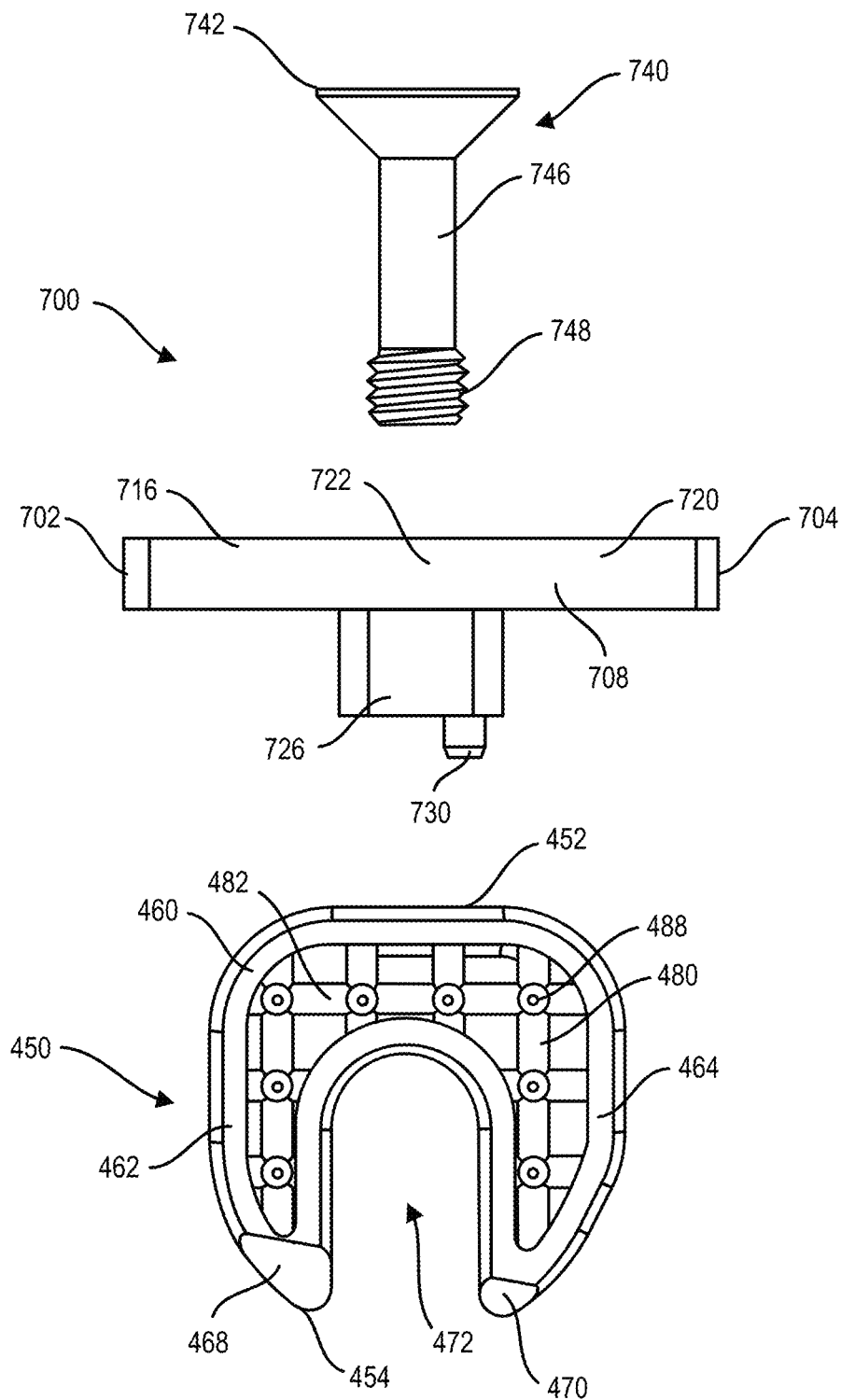
FIG. 56 is an exploded front view of the resection guide and implant of FIG. 54, in accordance with an aspect of the present invention.
Figure 58:
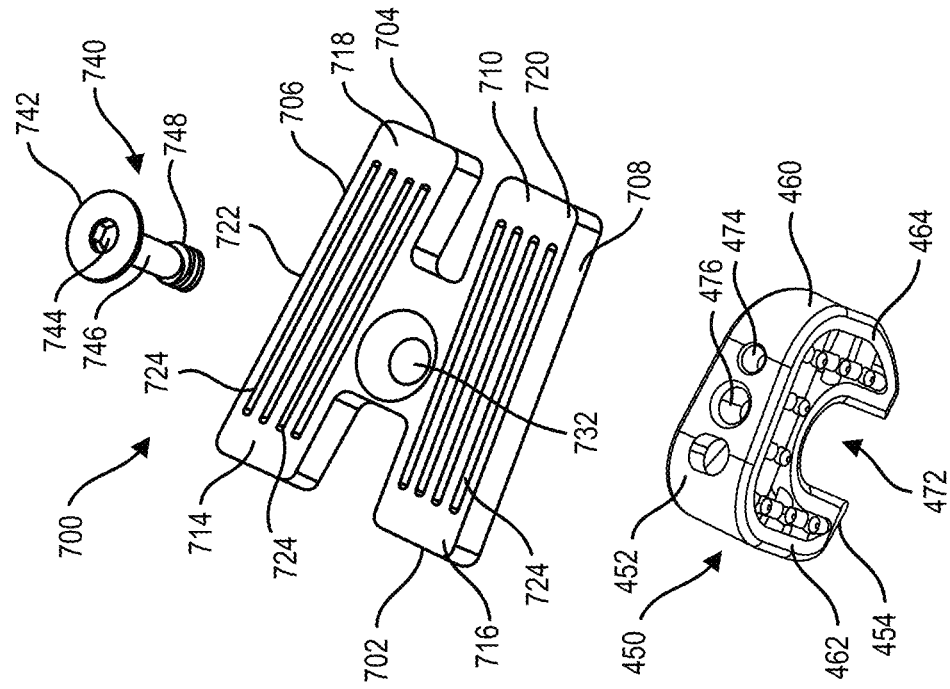
FIG. 58 is an exploded second side perspective view of the resection guide and implant of FIG. 54, in accordance with an aspect of the present invention.
Figure 57:
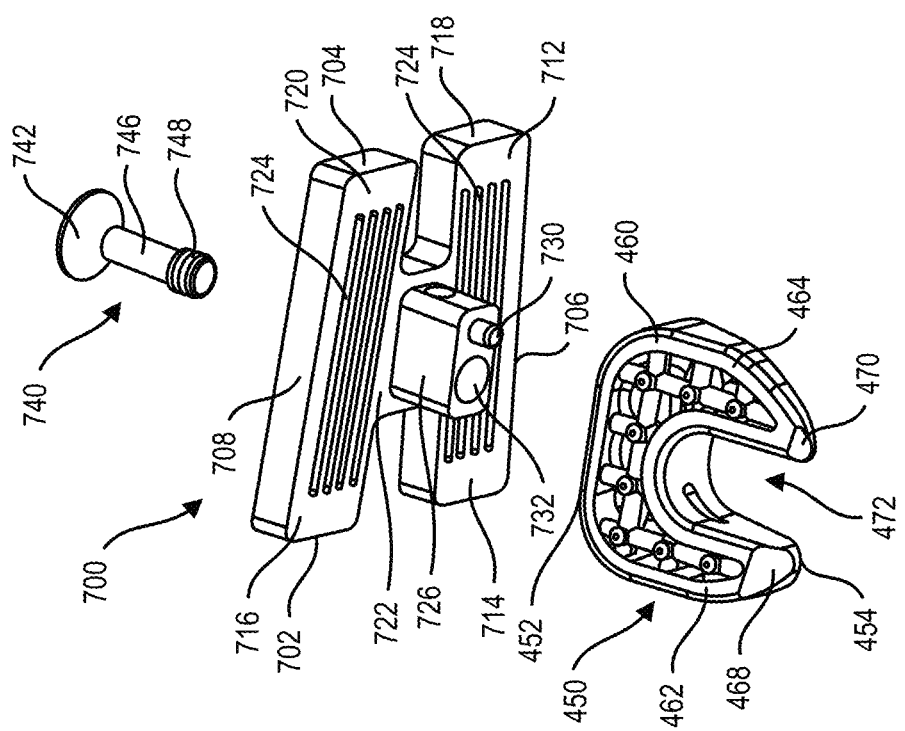
FIG. 57 is an exploded first side perspective view of the resection guide and implant of FIG. 54, in accordance with an aspect of the present invention.
Figure 59:
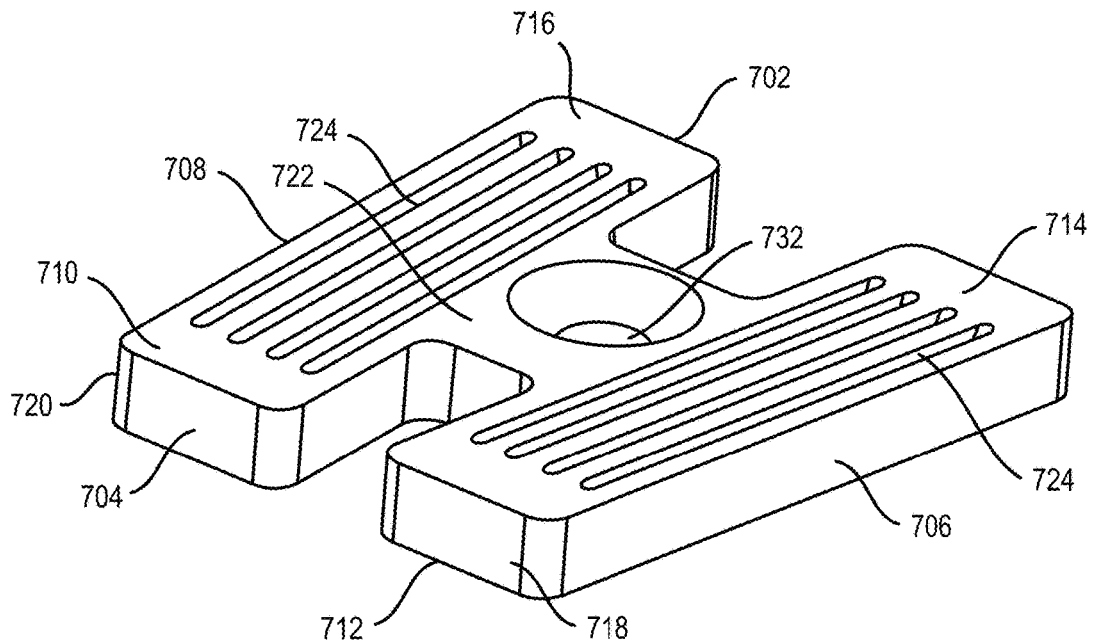
FIG. 59 is a perspective view of the resection guide of FIG. 54, in accordance with an aspect of the present invention.
Figure 60:
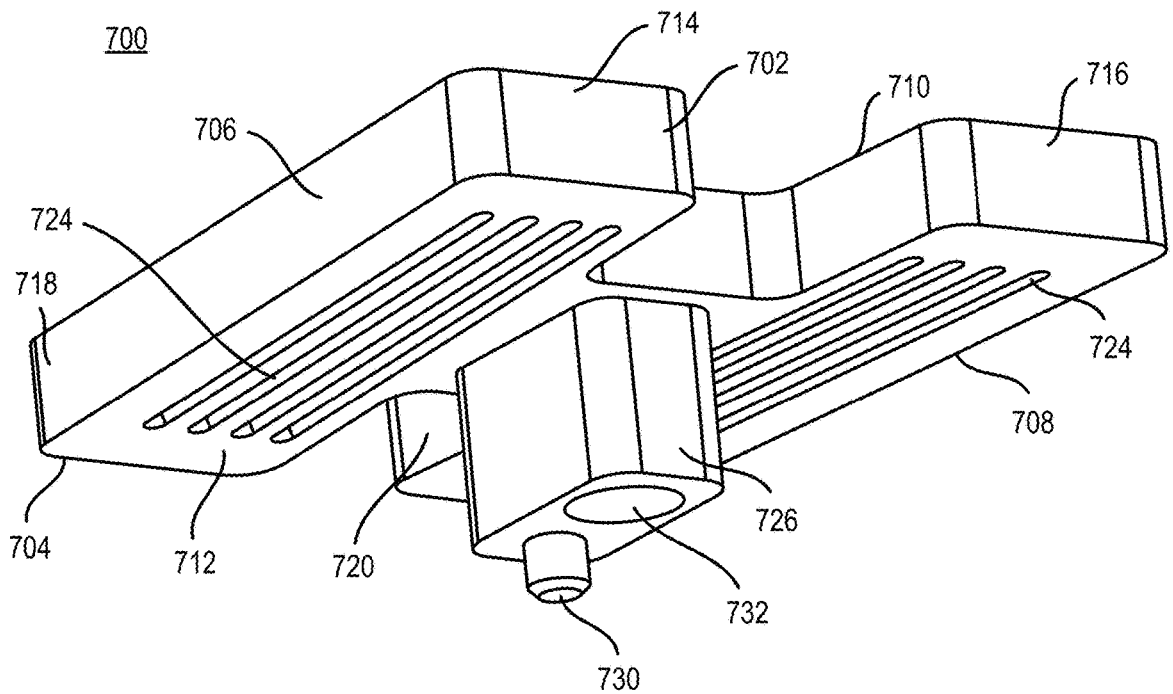
FIG. 60 is a perspective view of the resection guide of FIG. 54, in accordance with an aspect of the present invention.

As shown in FIGS. 56-58, the resection guide 700 may also include a fastener 740 for securing the resection guide 700 to the implant 400, 450. The fastener 740 may include a head portion 742 at a first end and a shaft 746 at a second end. The head portion 742 may include, for example, a driver opening 744 for receiving a tool to rotate the fastener 740 to engage the securement opening 426, 476 of the implant 400, 450. The shaft 746 may include a threaded end 748 with threads that correspond to the threads in the securement opening 426, 476. As the fastener 740 is inserted through the opening 732 in the resection guide 700, the threaded end 748 may engage the securement opening 426, 476 in the implant 400, 450. The opening 732 may include a retaining member or mechanism (not shown). The retaining member allows the threaded end 748 of the fastener 740 to pass through the opening 732 for coupling to the implant 400, 450, but prevents the fastener 740 from accidentally disengaging from the opening 732 in the resection guide 700. The retaining member may be, for example, an internal thread (not shown) to allow for the threaded end 748 to be threaded through the opening 732 for engagement with the implant 400, 450. A threaded retaining member would also allow for the fastener 740 to be removed and replaced if, for example, the threads on the threaded end 748 started wear away. Once the fastener 740 is completely tightened into the implant 400, 450, the head portion 742 of the fastener 740 will be, for example, flush with a top surface 710 of the resection guide 700 or recessed into the center portion 722 of the resection guide 700, as shown in FIG. 54.

Figure 66:
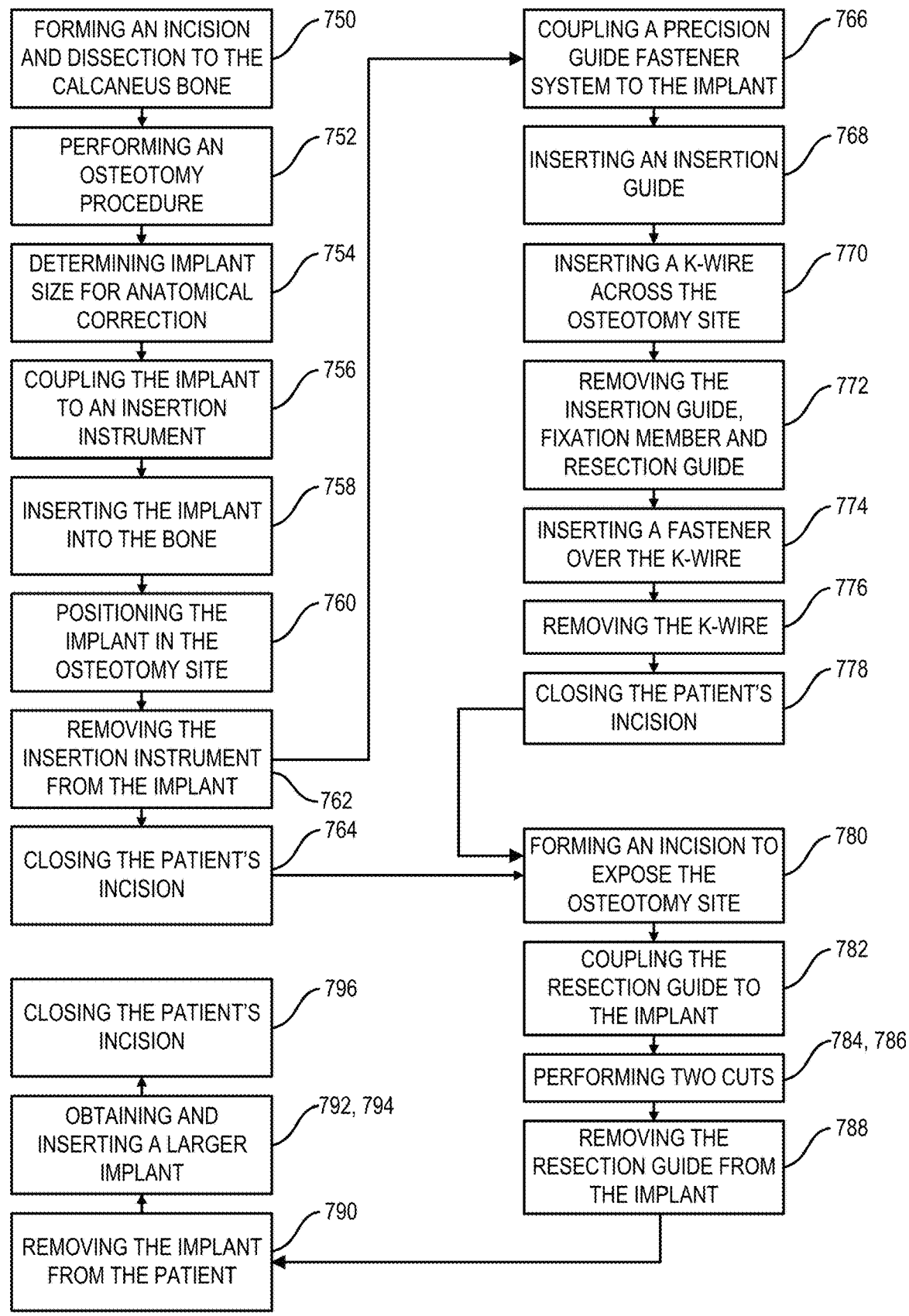
FIG. 66 depicts one embodiment of a surgical method for performing an Evans osteotomy, in accordance with an aspect of the present invention.

A surgical method of correcting bone deformities is shown in FIG. 66. The method includes, for example, performing an Evans osteotomy on the lateral side of the foot 690, as shown in FIGS. 51-53. An Evans osteotomy is performed to correct a valgus deformity of the foot commonly associated with a flatfoot deformity. The Evans osteotomy is performed by creating a cut in the calcaneus 692 approximately 1 cm proximal and parallel to the calcaneal-cuboid joint to allow for a graft or implant to be inserted, forming an opening wedge to correct the flatfoot deformity. Once the osteotomy is made, an implant 400, 450 is inserted into the calcaneus to extend the length of the bone 692, specifically the lateral column.

In an embodiment, the method may include making a skin incision and dissection down to the calcaneus bone 750. Next, the method may include locating the osteotomy site, approximately 1 cm from the cuboid bone, and using a saw, for example, a sagittal saw, to cut through the bone 752. The cut may be made on the lateral side, i.e. outside, of the calcaneus bone. Once the cut is made, trial sizers may be inserted into the cut to determine the appropriate sized implant for the desired anatomical correction 754. The trial sizers may match the geometry of the available implants to allow for selection of the implant that provides the required correction. After the implant size is selected, the implant is coupled to the insertion instrument 756. The implant may be coupled to the insertion instrument as described in greater detail above with reference to FIGS. 43-46. The implant 400, 450 may then be placed into the calcaneal osteotomy site 758 and, if necessary, the end of the insertion instrument may be impacted to correctly position the implant into the osteotomy site 760. Once the implant is inserted, the inserter instrument is removed from the implant 762, and if no additional procedures are to be performed, the patient's incision may be closed 764.

Optionally, the method may also include inserting a fastener across the osteotomy site and through the implant to strengthen the bone-implant construct. The fastener may be inserted by first coupling a guide fastener system to the implant using a fixation member 766, as described in greater detail above with reference to FIGS. 47-52. Next, an insertion guide is inserted through the guide fastener system at the desired fastener trajectory 768. A k-wire is then inserted through the insertion guide and advanced across the osteotomy site 770. After the k-wire is inserted, the insertion guide, fixation member, and guide fastener system are removed from the implant 772. Then, a fastener, such as a cannulated bone screw, is inserted over the k-wire and advanced across the osteotomy site through the implant 774. Once the fastener reaches the desired position, the k-wire is removed 776. Finally, the patient's incision may be closed 778.

The method may also optionally include a resection procedure if the implant needs to be removed for a revision surgery. The removal method may include, exposing the osteotomy site via a normal skin incision and soft tissue dissection 780. If a cannulated screw was inserted across the osteotomy site, the screw will be removed prior to making the cuts to remove the implant. The removal method may also include, obtaining a resection guide and attaching the resection guide to the implant 782, as described above with reference to FIGS. 54-65. Next, a saw blade is inserted through the selected first slot based on the size of the implant and the bone surrounding the implant is cut 784. After the first cut is made, the saw blade is inserted through the selected second slot corresponding to the selected first slot 786. After the two cuts are made, the resection guide may be detached from the implant 788 and the implant is removed from the osteotomy site in the patient's foot 790. Alternatively, the coupled resection guide and implant may be removed from the osteotomy site in the patient's foot and then the implant may be removed from the resection guide. Once the old implant is removed, a larger implant, for example, an implant one size larger than the original implant, may be selected 792 and the new implant is then inserted into the osteotomy site 794. After the osteotomy procedure is complete, the incision may be closed 796.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

Having thus described the preferred embodiments, the invention is now claimed to be:

1. A surgical method, comprising:
   performing an osteotomy procedure to form an opening in a bone, wherein the bone is a calcaneus;
   selecting an implant for insertion into the opening;
   coupling the implant to an insertion instrument;
   inserting the implant into the opening;
   removing the insertion instrument from the implant; and
   completing the osteotomy procedure, wherein the implant comprises:
      a body having a first end and a second end, with an opening extending through the body from a proximal surface to a distal surface, wherein the implant further comprises a three-dimensional matrix positioned in the opening and comprises:
         at least one linear member extending across the opening and coupled to the body; and
         at least one spike coupled to the at least one linear member and extending out from the body;
      a first leg extending from a first side of the body, wherein the first leg includes an exterior surface, wherein the exterior surface is curved as the first leg extends between the first end and the second end; and
      a second leg extending from a second side of the body, wherein the second leg is wider than the first leg, wherein the second leg includes an exterior surface, wherein the exterior surface is angled as the second leg extends between the first end and the second end.

2. The surgical method of claim 1, further comprising inserting one or more trial sizers into the opening in the bone to determine an approximate size of the implant for a desired anatomical correction.

3. The surgical method of claim 2, wherein the one or more trial sizers comprise a geometry that corresponds to the geometry of the implant.

4. The surgical method of claim 1, wherein the insertion instrument comprises:
   a body having a first end and a second end, wherein an impact portion is positioned at the first end;
   a nose portion, wherein the nose portion is positioned at the second end and comprises:
      a contact surface shaped to match a shape of a first end of the implant;
      an alignment pin extending from the contact surface to mate with an alignment opening in the implant; and
      a securement opening; and
   a securement member extending through the securement opening and projecting past the contact surface to couple to a securement opening in the implant.

5. The surgical method of claim 1, further comprising coupling a fastener guide system with the implant, wherein the fastener guide system comprises;
   an alignment arm with a first end and a second end, the alignment arm comprising:
      a base member; and
      a first arm coupled to the base member at the second end;
   an insertion guide removably coupled to the first end of the alignment arm; and
   a fixation member removably coupled to the second end of the alignment arm and extending through the alignment arm to engage the implant.

6. The surgical method of claim 5, further comprising inserting the insertion guide through the fastener guide system at a desired trajectory.

7. The surgical method of claim 6, further comprising inserting a k-wire through the insertion guide and advancing the k-wire across the osteotomy site.

8. The surgical method of claim 7, further comprising removing the insertion guide and the fastener guide system.

9. The surgical method of claim 8, further comprising inserting a cannulated fastener over the k-wire and advancing the fastener across the osteotomy site through the implant.

10. The surgical method of claim 9, further comprising removing the k-wire from the osteotomy site.

11. The surgical method of claim 10, further comprising performing an incision to expose the osteotomy site.

12. The surgical method of claim 11, further comprising obtaining a resection guide and coupling the resection guide to the implant, wherein the resection guide comprises:
   the resection guide comprises:
      a central portion with a first side opposite a second side and a first end opposite a second end;
      at least one first slot positioned on the first side of the central portion;
      at least one second slot positioned on the second side of the central portion;
      a first arm extending away from the first end on a first side and angled with respect to the central portion;
      a second arm extending away from the first end on a second side and angled with respect to the central portion;
      a first leg extending from the second end on the first side and angled with respect to the central portion; and
      a second leg extending from the second end on the second side and angled with respect to the central portion;
   wherein the at least one first slot and at least one second slot extend along the entire length of the central portion and into at least a portion of the at least one of the first leg and the second leg.

13. The surgical method of claim 12, further comprising inserting a cutting instrument through the at least one first slot of the resection guide based on a side of the implant and cutting a first portion of the bone surrounding the implant.

14. The surgical method of claim 13, further comprising inserting the cutting instrument through the at least one second slot of the resection guide that corresponds to the at least one first slot of the resection guide and cutting a second portion of the bone surrounding the implant.

15. The surgical method of claim 14, further comprising decoupling the resection guide from the implant and removing the implant from the osteotomy site.

16. The surgical method of claim 15, wherein the implant is a first implant, and wherein the method further comprises obtaining a second implant, wherein the second implant is of a different size than the first implant.

17. The surgical method of claim 12, wherein the at least one first slot and the at least one second slot of the resection guide form bi-angled openings, and wherein the angle of the at least one first slot matches an angle of the proximal surface of the implant and the angle of the at least one second slot matches an angle of the distal surface of the implant.

18. The surgical method of claim 1, wherein the body of the implant includes a dorsal to plantar taper and a medial to lateral taper.

* * * * *